(12) United States Patent
Melnick et al.

(10) Patent No.: US 10,689,366 B2
(45) Date of Patent: Jun. 23, 2020

(54) COMPOUNDS FOR MALT1 DEGREDATION

(71) Applicants: Cornell University, Ithaca, NY (US); Dana-Farber Cancer Institute, Inc., Boston, MA (US)

(72) Inventors: Ari M. Melnick, New York, NY (US); Lorena Fontan Gabas, New York, NY (US); Nathanael S. Gray, Boston, MA (US); David A. Scott, Newton, MA (US); John Hatcher, Marlborough, MA (US); Guangyan Du, Jamaica Plain, MA (US)

(73) Assignees: Cornell University, Ithaca, NY (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/346,483

(22) PCT Filed: Oct. 31, 2017

(86) PCT No.: PCT/US2017/059234
§ 371 (c)(1),
(2) Date: Apr. 30, 2019

(87) PCT Pub. No.: WO2018/085247
PCT Pub. Date: May 11, 2018

(65) Prior Publication Data
US 2019/0263785 A1    Aug. 29, 2019

Related U.S. Application Data

(60) Provisional application No. 62/416,066, filed on Nov. 1, 2016.

(51) Int. Cl.
| *C07D 401/14* | (2006.01) |
| *A61P 35/00* | (2006.01) |
| *A61K 31/4439* | (2006.01) |
| *A61K 31/519* | (2006.01) |
| *C07D 417/14* | (2006.01) |
| *C07D 471/04* | (2006.01) |
| *C07D 487/04* | (2006.01) |

(52) U.S. Cl.
CPC ........ *C07D 401/14* (2013.01); *A61K 31/4439* (2013.01); *A61K 31/519* (2013.01); *A61P 35/00* (2018.01); *C07D 417/14* (2013.01); *C07D 471/04* (2013.01); *C07D 487/04* (2013.01)

(58) Field of Classification Search
CPC .. C07D 401/14; C07D 417/14; C07D 471/04; C07D 487/04; A61P 35/00; A61K 31/4439; A61K 31/519
USPC ......................................... 544/281
See application file for complete search history.

(56) References Cited

U.S. PATENT DOCUMENTS

| 6,806,274 B1 * | 10/2004 | Crawley ............... C07D 215/54 514/266.2 |
| 2015/0291562 A1 | 10/2015 | Crew et al. |
| 2018/0256586 A1 * | 9/2018 | Crew ................... C07D 405/14 |

FOREIGN PATENT DOCUMENTS

| WO | WO 2009/060835 A1 | 11/2008 |
| WO | WO 2012/071414 A2 | 5/2012 |
| WO | WO 2015/181747 A1 | 12/2015 |

OTHER PUBLICATIONS

Afonina; FEBS Journal 2015, 282, 3286-3297. DOI: 10.1111/febs.13325 (Year: 2015).*
Caputo et al., Synthesis of benzothiazole derivatives and their biological evaluation as anticancer agents. Med Chem Res. 2012; 21(9):2644-2651.

* cited by examiner

*Primary Examiner* — Daniel R Carcanague
(74) *Attorney, Agent, or Firm* — Wolf, Greenfield & Sacks, P.C.

(57) ABSTRACT

Provided herein are bifunctional compounds that inhibit MALT1 and/or promote targeted ubiquitination for the degradation of MALT1. In particular, provided are compounds that can bind MALT1, a protein whose activity is responsible for constitutive NF-KB signaling in certain cancers (e.g., activated B-cell diffuse large B-cell lymphoma (ABC-DLBCL)), and can assist in its degradation by recruiting an E3 ubiquitin ligase (e.g., Cereblon, VHL), which can ubiquitinate MALT1, marking it for proteasome degradation. Also provided are pharmaceutical compositions comprising the bifunctional compounds, methods of treating cancer with the bifunctional compounds, methods of promoting the degradation of MALT1, and methods of binding E3 ubiquitin ligase activity in a subject by administering a compound or composition described herein.

19 Claims, 2 Drawing Sheets

COMPOUNDS FOR MALT1 DEGREDATION

RELATED APPLICATIONS

This application is a national stage filing under 35 U.S.C. § 371 of international PCT application, PCT/US2017/059234, filed Oct. 31, 2017, which claims priority under 35 U.S.C. § 119(e) to U.S. Provisional Application, U.S. Ser. No. 62/416,066, filed Nov. 1, 2016, the entire content of each is incorporated herein by reference.

STATEMENT OF GOVERNMENT INTEREST

This invention was made with government support under grant number CA182736 awarded by the National Institutes of Health. The government has certain rights in the invention.

FIELD OF THE INVENTION

The present invention relates generally to bifunctional compounds that inhibit MALT1 and promote its degradation via recruitment of an E3 ubiquitin ligase, and use of the compounds in the treatment of cancer.

BACKGROUND OF THE INVENTION

Diffuse large B-cell lymphoma (DLBCL) is a cancer of B cells and is the most common type of non-Hodgkin's lymphoma among adults. DLBCL is an aggressive tumor which can arise in almost any part of the body. Typically, DLBCL arises from normal B cells, but it can also represent a malignant transformation of other types of lymphoma or leukemia with underlying immunodeficiency being a significant risk factor. Despite advances in treatment, one third of DLBCL patients either do not respond or relapse within a short time. There are two major biologically distinct molecular subtypes of DLBCL: germinal center B-cell (GCB) and activated B-cell (ABC). ABC-DLBCL is derived from B cells that are in the process of differentiating from germinal center B cells to plasma cells. Typically, patients diagnosed with the ABC sybtype have poorer outcomes than GCB patients.

Mucosa-associated lymphoid tissue lymphoma translocation protein 1 (MALT1) is part of the paracaspase family and possesses proteolytic activity. It has an important role in the activation of the transcription factor NF-κB, in the production of interleukin-2 (IL-2), and in the proliferation of T and B lymphocytes. For example, the survival of several known ABC-DLBCL cell lines depends on a trio of signaling adapters: CARD11, MALT1, and BCL10. These proteins form the CBM complex that is involved in the antigen-dependent activation of NF-κB. In addition to acting as a scaffold protein within the CBM complex, MALT1 also contains a proteolytic activity that is constitutively activated in ABC-DLBCL. MALT1 inhibitors are known to inhibit NF-κB target gene expression and ABC-DLBCL viability, making MALT1 inhibition an attractive therapeutic target for the treatment of ABC-DLBCL.

E3 ubiquitin ligases are proteins that, in combination with an E2 ubiquitin-conjugating enzyme, promote the attachment of ubiquitin to a lysine on a target protein via an isopeptide bond (e.g., an amide bond that is not present on the main chain of a protein). The ubiquitination of the protein commonly results in degradation of the target protein by the proteasome.

The von Hippel-Lindau tumor suppressor (VHL) is an E3 ubiquitin ligase. VHL comprises the substrate recognition subunit/E3 ubiquitin ligase complex VCB, which includes elongins B and C, and a complex including Cullin-2 and Rbx1. The primary substrate of VHL is Hypoxia Inducible Factor 1α (HIF-1α), a transcription factor that upregulates genes, such as the pro-angiogenic growth factor VEGF and the red blood cell-inducing cytokine, erythropoietin, in response to low oxygen levels. VCB is a known target in cancer, chronic anemia, and ischemia.

Cereblon (CRBN) is another E3 ubiquitin ligase, and it forms an E3 ubiquitin ligase complex with damaged DNA binding protein 1 (DDB 1), Cullin-4A (CUL4A), and regulator of cullins 1 (ROC 1). This complex ubiquitinates a number of other proteins. Through a mechanism which has not been completely elucidated, Cereblon ubiquitination of target proteins results in increased levels of fibroblast growth factor 8 (FGF8) and fibroblast growth factor 10 (FGF10). FGF8, in turn, regulates a number of developmental processes, such as limb and auditory vesicle formation. In addition, studies suggest that small molecules that bind and inhibit Cereblon (e.g., lenalidomide) have direct antitumor activity against DLBCL cells, preferentially ABC-DLBCL cells.

An ongoing need exists to identify drugs that effectively treat cancers, such as DLBCL. In particular, drugs that can take advantage of cellular machinery involved in protein homeostasis (e.g., ubiquitination) may find particular use as therapeutic agents.

SUMMARY OF THE INVENTION

Both inhibition of the protease activity of MALT1 and modulation of certain E3 ubiquitin ligases (e.g., Cereblon) have been shown to have anti-proliferative effects on ABC-DLBCL cells. Furthermore, as part of the CBM complex, MALT1 has a scaffolding function, and disruption of the complex by MALT1 degradation may be useful in imparting additional therapeutic effects beyond those achieved by protease inhibition. Accordingly, the present disclosure stems from the recognition that, by targeting both MALT1 proteolytic activity and recruiting an E3 ubiquitin ligase (e.g., Cereblon, VHL) to ubiquitinate MALT1 and mark it for proteasome degradation, a single bifunctional compound can promote the inactivation and/or degradation of MALT1, thus providing new compounds, compostions, and methods useful for the treatment of cancer (e.g., hematological cancers such as DLBCL).

The present invention provides bifunctional compounds that are inhibitors of MALT1 and recruit certain E3 ligases (e.g., Cereblon, VHL) to promote the degradation of MALT1. As inhibitors of MALT1, the compounds of the invention act to bind MALT1, and inhibit its constitutive proteolytic activity common in some cancers, thereby conferring anti-proliferative activity. The compounds can also provide anti-cancer activity through recruitment and binding of E3 ubiquitin ligases by a linked moiety (e.g., lenalidomide), which can further promote the labeling of MALT1 with ubiquitin, marking it for proteasome degradation, and thus disrupting the CBM complex, which is vital to constitutive activation of NF-κB signaling in certain cancers (e.g., DLBCL). The present invention also provides methods of treating cancer with the compounds, and compositions thereof. Thus, the present invention represents an important advance in the treatment of cancer, particularly DLBCL.

In one aspect, provided are compounds of Formula I:

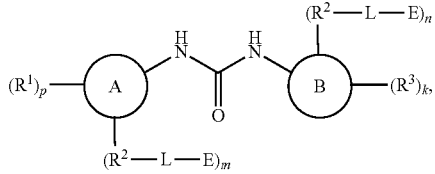

or pharmaceutically acceptable salts, co-crystals, tautomers, stereoisomers, solvates, hydrates, polymorphs, isotopically enriched derivatives, or prodrugs thereof, wherein:

A is a fused bicyclic heteroaryl ring;
B is phenyl or pyridinyl;
each occurrence of $R^1$ and $R^3$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —$C(=NR^A)R^A$, —$C(=NR^A)OR^A$, —$C(=NR^A)N(R^A)_2$, —$C(=O)R^A$, —$C(=O)OR^A$, —$C(=O)N(R^A)_2$, —$NO_2$, —$NR^AC(=O)R^A$, —$NR^AC(=O)OR^A$, —$NR^AC(=O)N(R^A)_2$, —$OC(=O)R^A$, —$OC(=O)OR^A$, —$OC(=O)N(R^A)_2$, or a nitrogen protecting group when attached to a nitrogen atom;

$R^2$ is substituted or unsubstituted alkylene, substituted or unsubstituted heterocyclylene, substituted or unsubstituted arylene, substituted or unsubstituted heteroarylene, substituted or unsubstituted heteroalkylene, substituted or unsubstituted alkylheteroarylene, substituted or unsubstituted heteroarylalkylene, —O—, —$N(R^A)$—, —S—, —$C(=O)$—, —$C(=O)O$—, —$C(=O)NR^A$—, —$NR^AC(=O)$—, —$NR^AC(=O)O$—, —$NR^AC(=O)N(R^A)$—, —$OC(=O)$—, —$OC(=O)O$—, or —$OC(=O)N(R^A)$—;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring;

L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, —O—, —$N(R^A)$—, —S—, —$C(=O)$—, —$C(=O)O$—, —$C(=O)NR^A$—, —$NR^AC(=O)$—, —$NR^AC(=O)R^A$—, —$C(=O)R^A$—, —$NR^AC(=O)O$—, —$NR^AC(=O)N(R^A)$—, —$OC(=O)$—, —$OC(=O)O$—, or —$OC(=O)N(R^A)$—, or a combination thereof; E is an E3 ubiquitin ligase binding moiety;

m and n are each independently 0 or 1, provided that m+n=1;
k is 0, 1, 2, 3, or 4; and
p is 0, 1, 2, 3, or 4.

Exemplary compounds of Formula I include, but are not limited to:

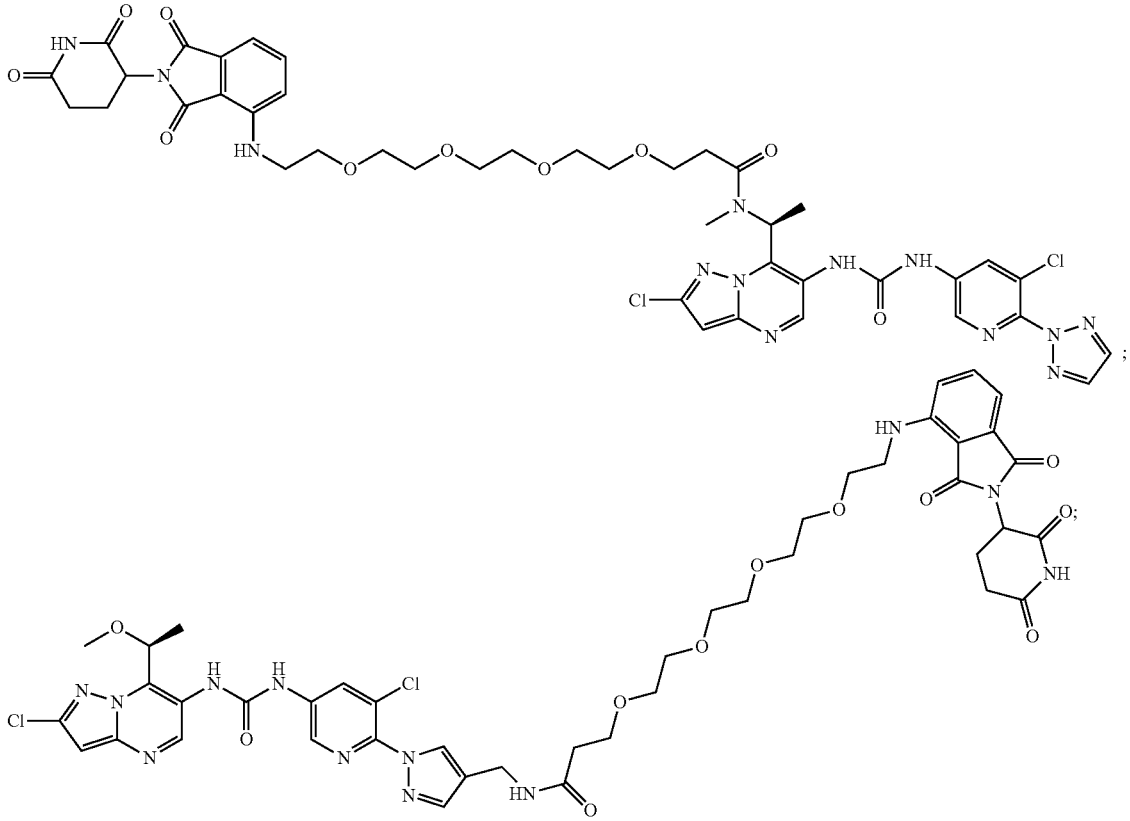

-continued
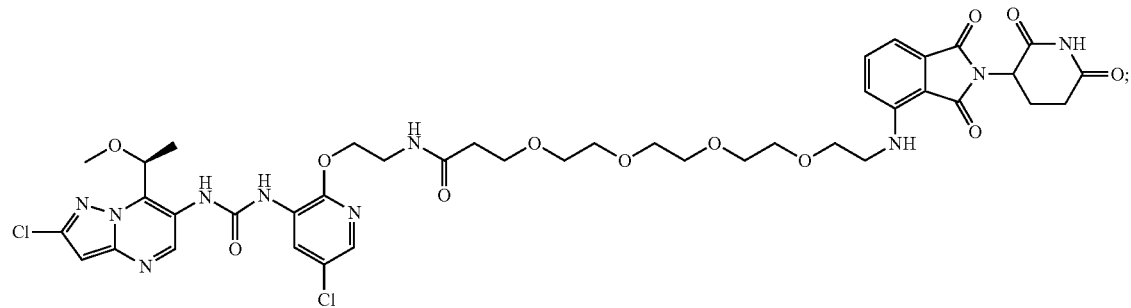
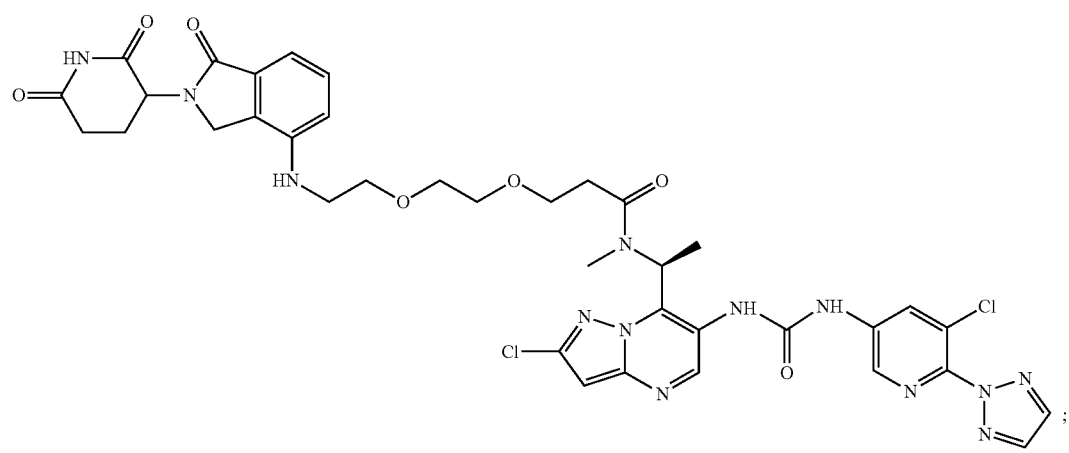
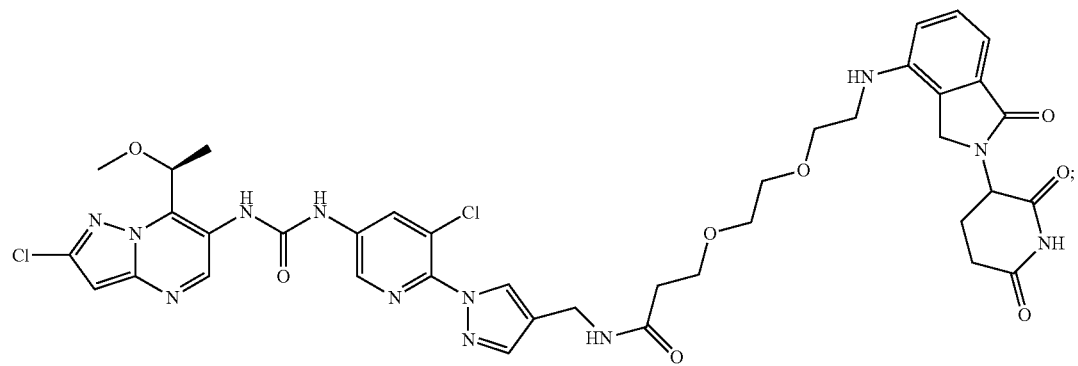
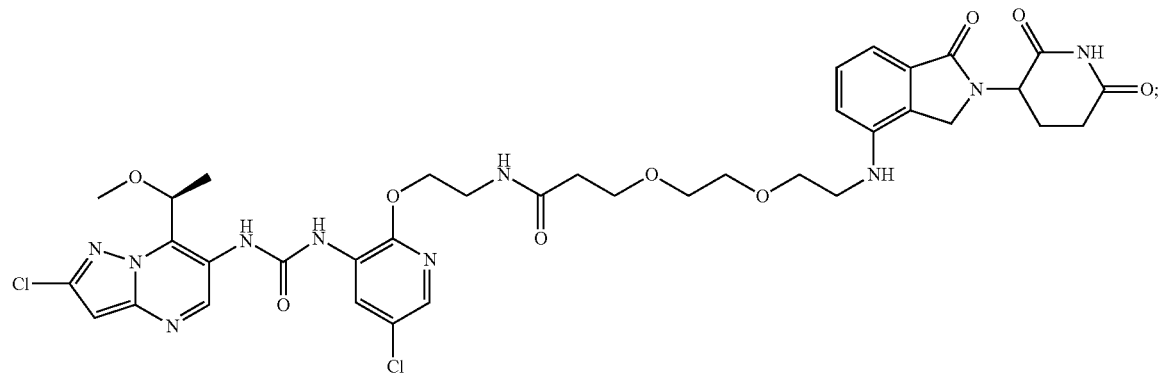

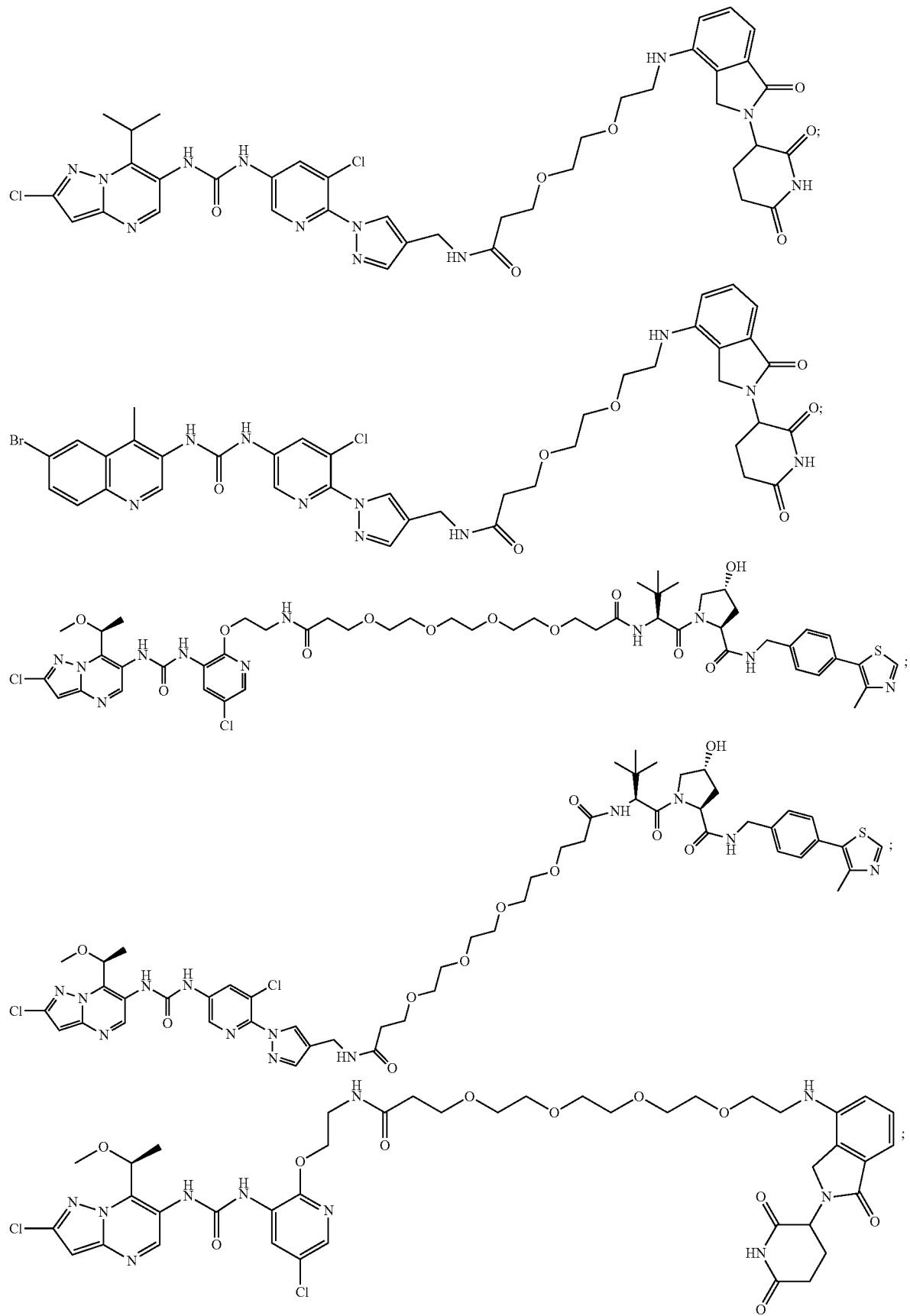

-continued
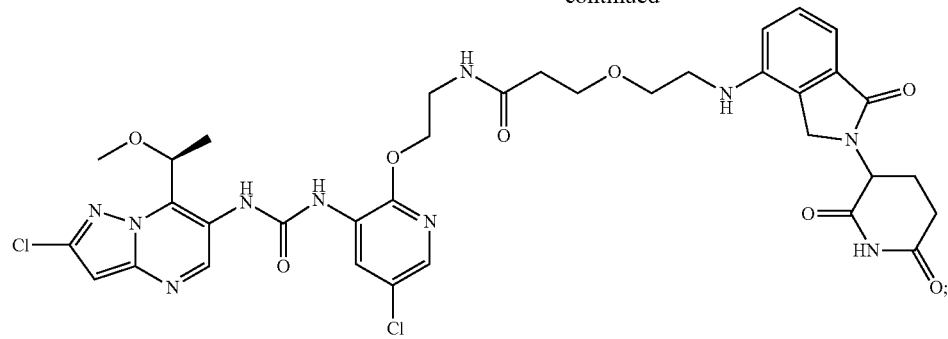
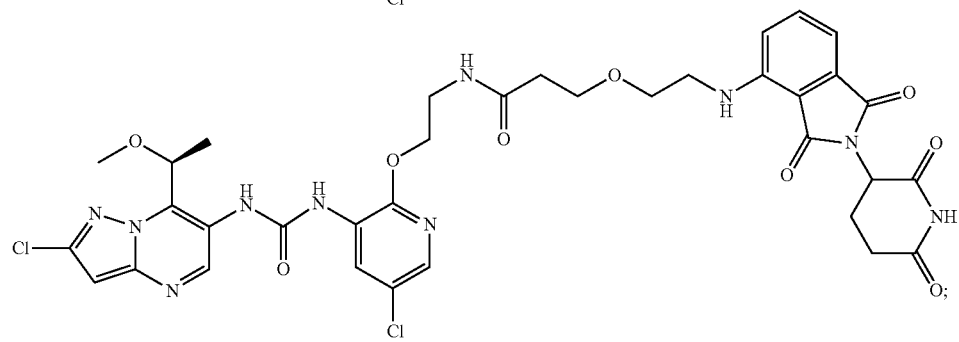
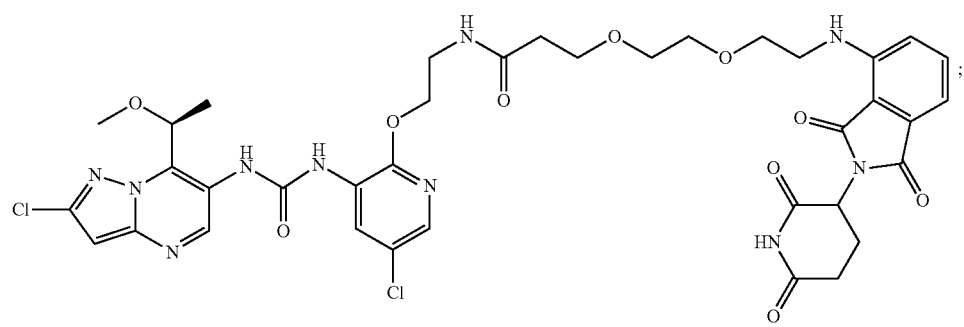
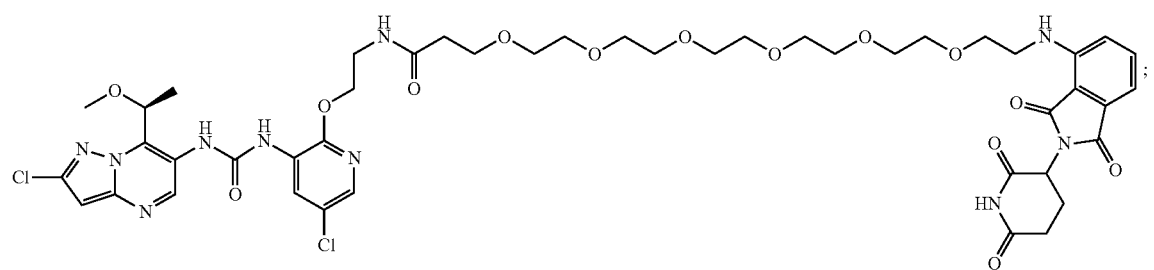
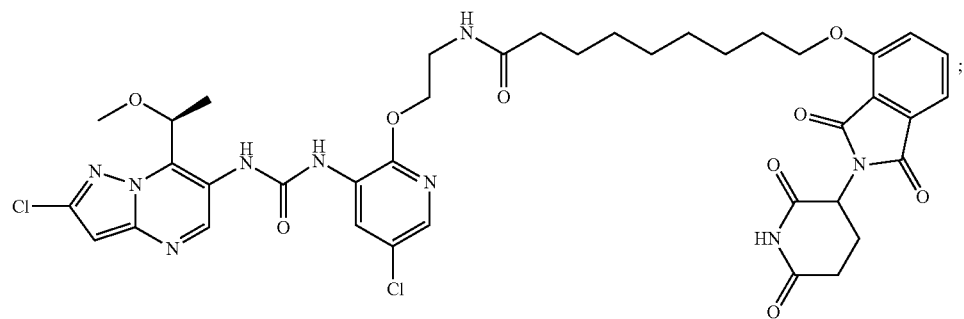

-continued

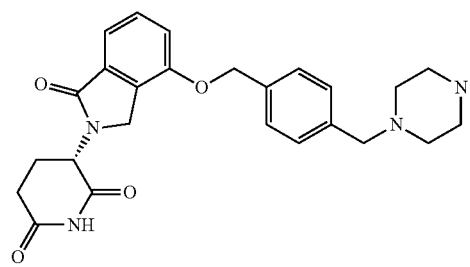
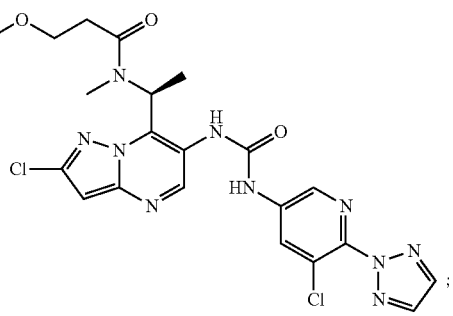
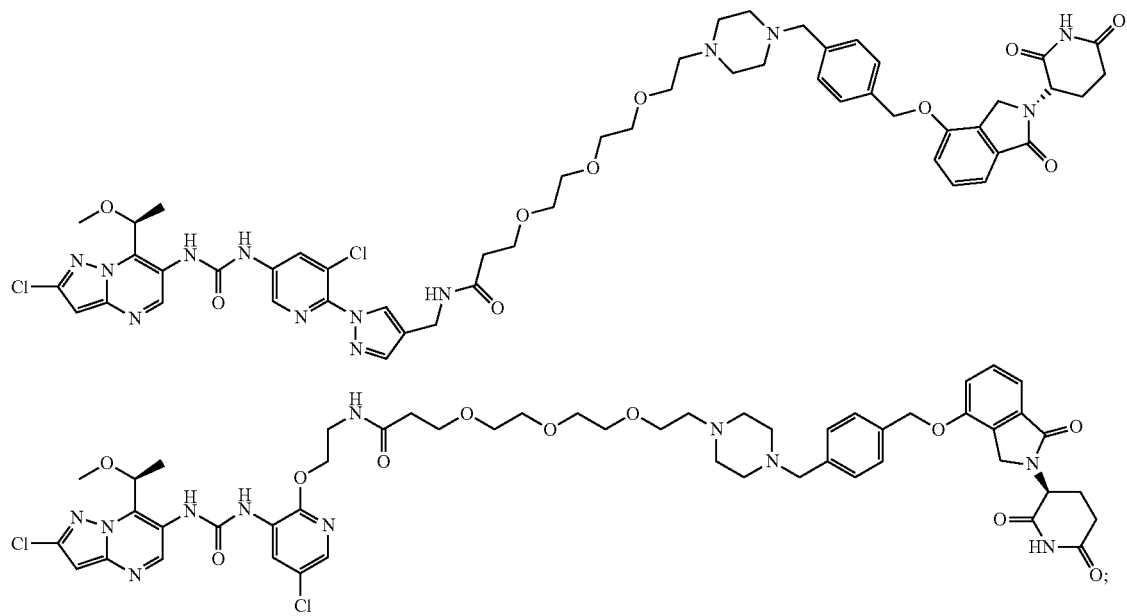

or pharmaceutically acceptable salts thereof.

In another aspect, provided are pharmaceutical compositions comprising a compound of Formula I, or a pharmaceutically acceptable salt thereof, and a pharmaceutically acceptable excipient.

In another aspect, provided are methods of treating cancer in a subject in need thereof, the method comprising administering a compound of Formula I, or a pharmaceutically acceptable salt thereof, or a pharmaceutical composition comprising a compound of Formula I to the subject. In certain embodiments, the cancer is a hematological cancer. In certain embodiments, the cancer is a lymphoid malignancy. In certain embodiments, the hematological cancer is a leukemia, lymphoma, or multiple myeloma. In certain embodiments, the cancer is a diffuse large B-cell lymphoma (e.g. ABC-DLBCL).

In another aspect, provided are methods of promoting the degradation of MALT1 in a subject in need thereof, the method comprising administering a compound of Formula I, or a pharmaceutically acceptable salt thereof, or a pharmaceutical composition comprising a compound of Formula I to the subject.

In another aspect, provided are methods of promoting the degradation of MALT1 and binding an E3 ubiquitin ligase in a subject in need thereof, the method comprising administering a compound of Formula I, or a pharmaceutically acceptable salt thereof, or a pharmaceutical composition comprising a compound of Formula I to the subject. In certain embodiments, the E3 ubiquitin ligase is Cereblon or VHL.

In another aspect, provided are compounds of Formula I, or pharmaceutically acceptable salts thereof, or pharmaceutical compositions comprising a compound of Formula I for use in treating cancer in a subject in need thereof; promoting the degradation of MALT1; and promoting the degradation of MALT1 and binding an E3 ubiquitin ligase (e.g., Cereblon, VHL).

In another aspect, provided are kits comprising a compound of Formula I, or a pharmaceutically acceptable salt thereof, or a pharmaceutical composition comprising a compound of Formula I. In certain embodiments, the kits further comprise instructions for administration (e.g., human administration).

The details of certain embodiments of the invention are set forth in the Detailed Description of Certain Embodiments, as described below. Other features, objects, and advantages of the invention will be apparent from the Definitions, Examples, Figures, and Claims.

DEFINITIONS

Chemical Definitions

Figure 1:
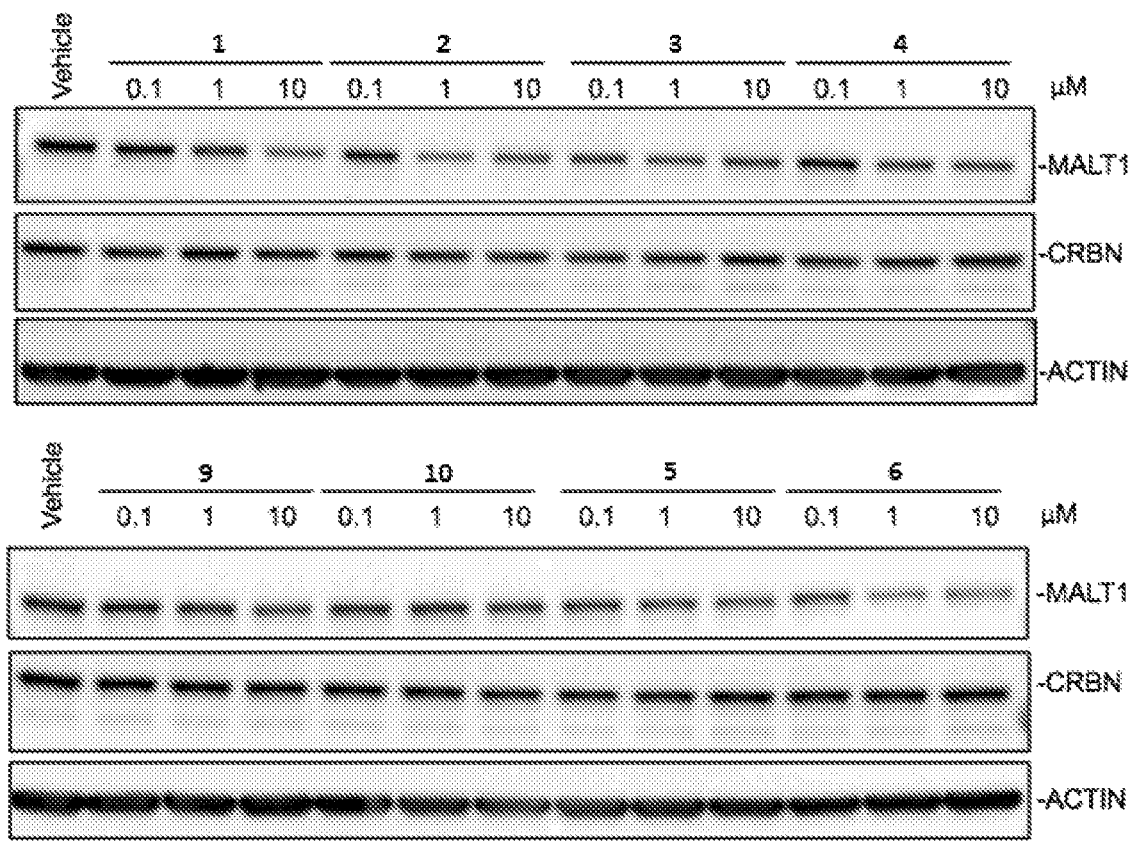
FIG. 1 shows images of Western blots demonstrating the promotion of MALT1 degradation by Examples 1-6, 9, and 10 in OCI-Ly3 cells. In the experiments, OCI-Ly3 cells were grown for 6 hours in the presence of the indicated concentrations of Examples 1-6, 9, and 10. Proteins were extracted, analyzed by Western blot, and membranes were immunoblotted for MALT1, CRBN, and Actin.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March, March's Advanced Organic Chemistry, 5$^{th}$ Edition, John Wiley & Sons, Inc., New York, 2001; Larock, Comprehensive Organic Transformations, VCH Publishers, Inc., New York, 1989; and Carruthers, Some Modern Methods of Organic Synthesis, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, E. L. Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ~~~ is a single bond where the stereochemistry of the moieties immediately attached thereto is not specified, - - - is absent or a single bond, and === or ≡≡≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —CHF$_2$, —CH$_2$F, —CF$_3$, —CH$_2$CF$_3$, —CF$_2$CF$_3$, —CF$_2$CF$_2$CF$_3$, —CCl$_3$, —CFCl$_2$, —CF$_2$Cl, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 20 carbon atoms and 1 or more heteroatoms within the parent chain ("heteroC$_{1-20}$ alkyl"). In some embodiments, a heteroalkyl group is a saturated group having 1 to 18 carbon atoms and 1 or more heteroatoms within the parent chain ("heteroC$_{1-18}$ alkyl"). In some embodiments, a heteroalkyl group is a saturated group having 1 to 16 carbon atoms and 1 or more heteroatoms within the parent chain ("heteroC$_{1-6}$ alkyl"). In some embodiments, a heteroalkyl group is a saturated group having 1 to 14 carbon atoms and 1 or more heteroatoms within the parent chain ("heteroC$_{1-14}$ alkyl"). In some embodiments, a heteroalkyl group is a saturated group having 1 to 12 carbon atoms and 1 or more heteroatoms within the parent chain ("heteroC$_{1-10}$ alkyl"). In some embodiments, a heteroalkyl group is a saturated group having 1 to 10 carbon atoms and 1 or more heteroatoms within the parent chain ("heteroC$_{1-10}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, the heteroalkyl group defined herein is a partially unsaturated group having 1 or more heteroatoms within the parent chain and at least one unsaturated carbon, such as a carbonyl group. For example, a heteroalkyl group may comprise an amide or ester functionality in its parent chain such that one or more carbon atoms are unsaturated carbonyl groups. Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-20}$ alkyl. In certain embodiments, the heteroalkyl group is an unsubstituted heteroC$_{1-10}$ alkyl. In certain embodiments, the heteroalkyl group is a substituted heteroC$_{1-20}$ alkyl. In certain embodiments, the heteroalkyl group is an unsubstituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

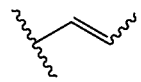

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and 1 or 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl").

Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4] diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl, and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_3$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)

$OR^{aa}$, $-OC(=NR^{bb})R^{aa}$, $-OC(=NR^{bb})OR^{aa}$, $-C(=NR^{bb})N(R^{bb})_2$, $-OC(=NR^{bb})N(R^{bb})_2$, $-NR^{bb}C(=NR^{bb})N(R^{bb})_2$, $-C(=O)NR^{bb}SO_2R^{aa}$, $-NR^{bb}SO_2R^{aa}$, $-SO_2N(R^{bb})_2$, $-SO_2R^{aa}$, $-SO_2OR^{aa}$, $-OSO_2R^{aa}$, $-S(=O)R^{aa}$, $-OS(=O)R^{aa}$, $-Si(R^{aa})_3$, $-OSi(R^{aa})_3$ $-C(=S)N(R^{bb})_2$, $-C(=O)SR^{aa}$, $-C(=S)SR^{aa}$, $-SC(=S)SR^{aa}$, $-SC(=O)SR^{aa}$, $-OC(=O)SR^{aa}$, $-SC(=O)OR^{aa}$, $-SC(=O)R^{aa}$, $-P(=O)(R^{aa})_2$, $-P(=O)(OR^{cc})_2$, $-OP(=O)(R^{aa})_2$, $-OP(=O)(OR^{cc})_2$, $-P(=O)(N(R^{bb})_2)_2$, $-OP(=O)(N(R^{bb})_2)_2$, $-NR^{bb}P(=O)(R^{aa})_2$, $-NR^{bb}P(=O)(OR^{cc})_2$, $-NR^{bb}P(=O)(N(R^{bb})_2)_2$, $-P(R^{cc})_2$, $-P(OR^{cc})_2$, $-P(R^{cc})_3^+X^-$, $-P(OR^{cc})_3^+X^-$, $-P(R^{cc})_4$, $-P(OR^{cc})_4$, $-OP(R^{cc})_2$, $-OP(R^{cc})_3^+X^-$, $-OP(OR^{cc})_2$, $-OP(OR^{cc})_3^+X^-$, $-OP(R^{cc})_4$, $-OP(OR^{cc})_4$, $-B(R^{aa})_2$, $-B(OR^{cc})_2$, $-BR^{aa}(OR^{cc})$, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group $=O$, $=S$, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)(R^{aa})_2$, $-P(=O)(OR^{cc})_2$, $-P(=O)(N(R^{cc})_2)_2$, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R^{ff})_2$, $-NR^{ff}C(=O)R^{ee}$, $-NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR^{ff})N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{ff})_2$, $-C(=O)SR^{ee}$, $-C(=S)SR^{ee}$, $-SC(=S)SR^{ee}$, $-P(=O)(OR^{ee})_2$, $-P(=O)(R^{ee})_2$, $-OP(=O)(R^{ee})_2$, $-OP(=O)(OR^{ee})_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form $=O$ or $=S$; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl$)_2$, $-N(C_{1-6}$ alkyl$)_2$, $-N(C_{1-6}$ alkyl$)_3^+X^-$, $-NH(C_{1-6}$ alkyl$)_2^+X^-$, $-NH_2(C_{1-6}$ alkyl$)^+X^-$, $-NH_3^+X^-$, $-N(OC_{1-6}$ alkyl$)(C_{1-6}$ alkyl$)$, $-N(OH)(C_{1-6}$ alkyl$)$, $-NH(OH)$, $-SH$, $-SC_{1-6}$ alkyl, $-SS(C_{1-6}$ alkyl$)$, $-C(=O)(C_{1-6}$ alkyl$)$, $-CO_2H$, $-CO_2(C_{1-6}$ alkyl$)$, $-OC(=O)(C_{1-6}$ alkyl$)$, $-OCO_2(C_{1-6}$ alkyl$)$, $-C(=O)NH_2$, $-C(=O)N(C_{1-6}$ alkyl$)_2$, $-OC(=O)NH(C_{1-6}$ alkyl$)$, $-NHC(=O)(C_{1-6}$ alkyl$)$, $-N(C_{1-6}$ alkyl$)C(=O)(C_{1-6}$ alkyl$)$, $-NHCO_2(C_{1-6}$ alkyl$)$, $-NHC(=O)N(C_{1-6}$ alkyl$)_2$, $-NHC(=O)NH(C_{1-6}$ alkyl$)$, $-NHC(=O)NH_2$, $-C(=NH)O(C_{1-6}$ alkyl$)$, $-OC(=NH)(C_{1-6}$ alkyl$)$, $-OC(=NH)OC_{1-6}$ alkyl, $-C(=NH)N(C_{1-6}$ alkyl$)_2$, $-C(=NH)NH(C_{1-6}$ alkyl$)$, $-C(=NH)NH_2$, $-OC(=NH)N(C_{1-6}$ alkyl$)_2$, $-OC(=NH)NH(C_{1-6}$ alkyl$)$, $-OC(=NH)NH_2$, $-NHC(=NH)N(C_{1-6}$ alkyl$)_2$, $-NHC(=NH)NH_2$, $-NHSO_2(C_{1-6}$ alkyl$)$, $-SO_2N(C_{1-6}$ alkyl$)_2$, $-SO_2NH(C_{1-6}$ alkyl$)$, $-SO_2NH_2$, $-SO_2(C_{1-6}$ alkyl$)$, $-SO_2O(C_{1-6}$ alkyl$)$, $-OSO_2(C_{1-6}$ alkyl$)$, $-SO(C_{1-6}$ alkyl$)$, $-Si(C_{1-6}$ alkyl$)_3$, $-OSi(C_{1-6}$ alkyl$)_3$-$C(=S)N(C_{1-6}$ alkyl$)_2$, $C(=S)NH(C_{1-6}$ alkyl$)$, $C(=S)NH_2$, $-C(=O)S(C_{1-6}$ alkyl$)$, $-C(=S)SC_{1-6}$ alkyl, $-SC(=S)SC_{1-6}$ alkyl, $-P(=O)(OC_{1-6}$ alkyl$)_2$, $-P(=O)(C_{1-6}$ alkyl$)_2$, $-OP(=O)(C_{1-6}$ alkyl$)_2$, $-OP(=O)(OC_{1-6}$ alkyl$)_2$, $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$ alkenyl, heteroC$_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form $=O$ or $=S$; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(=O)(R$^{aa}$)$_2$, —OP(=O)(OR$^{cc}$)$_2$, and —OP(=O)(N(R$^{bb}$)$_2$)$_2$, wherein X$^-$, R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NH$^{bb}$P(=O)(OR$^{cc}$)$_2$, and —NH$^{bb}$P(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)Rx, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, —C(=S)O(R$^{X1}$), —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (e.g., —C(=O)R$^{aa}$), carboxylic acids (e.g., —CO$_2$H), aldehydes (—CHO), esters (e.g., —CO$_2$R$^{aa}$, —C(=O)SR$^{aa}$, —C(=S)SR$^{aa}$), amides (e.g., —C(=O)N(R$^{bb}$)$_2$, —C(=O)NR$^{bb}$SO$_2$R$^{aa}$, —C(=S)N(R$^{bb}$)$_2$), and imines (e.g., —C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "boronyl" refers to boranes, boronic acids, boronic esters, borinic acids, and borinic esters, e.g., boronyl groups of the formula —B(R$^{aa}$)$_2$, —B(OR$^{cc}$)$_2$, and —BR$^{aa}$(OR$^{cc}$), wherein R$^{aa}$ and R$^{cc}$ are as defined herein.

The term "phosphino" refers to the group —P(R$^{cc}$)$_3$, wherein R$^{cc}$ is as defined herein.

An exemplary phosphino group is triphenylphosphine.

The term "phosphono" refers to the group —O(P=O)(OR$^{cc}$)R$^{aa}$, wherein R$^{aa}$ and R$^{cc}$ are as defined herein.

The term "phosphoramido" refers to the group —O(P=O)(N(R$^{bb}$)$_2$)$_2$, wherein each R$^{bb}$ is as defined herein.

The term "stannyl" refers to the group —Sn(R$^{cc}$)$_3$, wherein R$^{cc}$ is as defined herein.

The term "germyl" refers to the group —Ge(R$^{cc}$)$_3$, wherein R$^{cc}$ is as defined herein.

The term "arsenyl" refers to the group —As(R$^{cc}$)$_3$, wherein R$^{cc}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, heteroC$_{1-10}$alkyl, heteroC$_{2-10}$alkenyl, heteroC$_{2-10}$alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3rd edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group is benzyl (Bn), tert-butyloxycarbonyl (BOC), carbobenzyloxy (Cbz), 9-flurenylmethyloxycarbonyl (Fmoc), trifluoroacetyl, triphenylmethyl, acetyl (Ac), benzoyl (Bz), p-methoxybenzyl (PMB), 3,4-dimethoxybenzyl (DMPM), p-methoxyphenyl (PMP), 2,2,2-trichloroethyloxycarbonyl (Troc), triphenylmethyl (Tr), tosyl (Ts), brosyl (Bs), nosyl (Ns), mesyl (Ms), triflyl (Tf), or dansyl (Ds).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group is silyl. In certain embodiments, an oxygen protecting group is t-butyldiphenylsilyl (TBDPS), t-butyldimethylsilyl (TBDMS), triisoproylsilyl (TIPS), triphenylsilyl (TPS), triethylsilyl (TES), trimethylsilyl (TMS), triisopropylsiloxymethyl (TOM), acetyl (Ac), benzoyl (Bz), allyl carbonate, 2,2,2-trichloroethyl carbonate (Troc), 2-trimethylsilylethyl carbonate, methoxymethyl (MOM), 1-ethoxyethyl (EE), 2-methyoxy-2-propyl (MOP), 2,2,2-trichloroethoxyethyl, 2-methoxyethoxymethyl (MEM), 2-trimethylsilylethoxymethyl (SEM), methylthiomethyl (MTM), tetrahydropyranyl (THP), tetrahydrofuranyl (THF), p-methoxyphenyl (PMP), triphenylmethyl (Tr), methoxytrityl (MMT), dimethoxytrityl (DMT), allyl, p-methoxybenzyl (PMB), t-butyl, benzyl (Bn), allyl, or pivaloyl (Piv).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —P(OR$^{cc}$)$_2$, —P(OR$^{cc}$)$_3$$^+$X$^-$, —P(=O)(R$^{aa}$)$_2$, —P(=O)(OR$^{cc}$)$_2$, and —P(=O)(N(R$^{bb}$)$_2$)$_2$, wherein R$^{aa}$, R$^{bb}$, and R$^{cc}$ are as defined herein. Sulfur protecting groups are well known in the art and include those described in detail in Protecting Groups in Organic Synthesis, T. W. Greene and P. G. M. Wuts, 3rd edition, John Wiley & Sons, 1999, incorporated herein by reference. In certain embodiments, a sulfur protecting group is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F, Cl Br, F), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$$^-$, B(C$_6$F$_5$)$_4$$^-$, BPh$_4$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "leaving group" is given its ordinary meaning in the art of synthetic organic chemistry and refers to an atom or a group capable of being displaced by a nucleophile. See, for example, Smith, *March's Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties. Further exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The term "carbohydrate" or "saccharide" refers to an aldehydic or ketonic derivative of polyhydric alcohols. Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula C$_y$H$_{2y}$O$_y$ (e.g., C$_6$H$_{12}$O$_6$ (a hexose such as glucose)), wherein y is an integer equal to or greater than 3. Certain polyhydric alcohols not represented by the general formula described above may also be considered monosaccharides. For example, deoxyribose is of the formula C$_5$H$_{10}$O$_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula C$_6$H$_{12}$O$_6$, of which all but two of its six carbons atoms are stereogenic, making D-glucose one of the 16 (i.e., 2$^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an α anomer, the —OH substituent on the anomeric carbon rests on the opposite side (trans) of the ring from the —CH$_2$OH side branch. The alternative form, in which the —CH$_2$OH substituent and the anomeric hydroxyl are on the same side (cis) of the plane of the ring, is called a β anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x H$_2$O, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5H$_2$O)), and polyhydrates (x is a number greater than 1, e.g., dihydrates (R.2H$_2$O) and hexahydrates (R.6H$_2$O)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_{1-8}$ alkyl, $C_{2-8}$ alkenyl, $C_{2-8}$ alkynyl, aryl, $C_7$-12 substituted aryl, and $C_{7-12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. The term "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "target tissue" refers to any biological tissue of a subject (including a group of cells, a body part, or an organ) or a part thereof, including blood and/or lymph vessels, which is the object to which a compound, particle, and/or composition of the invention is delivered. A target tissue may be an abnormal or unhealthy tissue, which may need to be treated. A target tissue may also be a normal or healthy tissue that is under a higher than normal risk of becoming abnormal or unhealthy, which may need to be prevented. In certain embodiments, the target tissue is the liver. In certain embodiments, the target tissue is the lung. A "non-target tissue" is any biological tissue of a subject (including a group of cells, a body part, or an organ) or a part thereof, including blood and/or lymph vessels, which is not a target tissue.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for MALT1 inhibition and/or promoting the degradation of MALT1. In certain embodiments, a therapeutically effective amount is an amount sufficient for treating cancer (e.g., DLBCL). In certain embodiments, a therapeutically effective amount is an amount sufficient for MALT1 inhibition and/or promoting the degradation of MALT1 and treating cancer (e.g., DLBCL).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for MALT1 inhibition and/or promoting the degradation of MALT1. In certain embodiments, a prophylactically effective amount is an amount sufficient for treating cancer (e.g., DLBCL). n certain embodiments, a prophylactically effective amount is an amount sufficient for MALT1 inhibition and/or promoting the degradation of MALT1 and treating cancer (e.g., DLBCL).

As used herein, the term "inhibit" or "inhibition" in the context of enzymes, for example, in the context of MALT1, refers to a reduction in the activity of the enzyme. In some embodiments, the term refers to a reduction of the level of enzyme activity, e.g., MALT1 activity, to a level that is statistically significantly lower than an initial level, which may, for example, be a baseline level of enzyme activity. In some embodiments, the term refers to a reduction of the level of enzyme activity, e.g., MALT1 activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematological cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "immunotherapy" refers to a therapeutic agent that promotes the treatment of disease by inducing, enhancing, or suppressing an immune response. Immunotherapies designed to elicit or amplify an immune response are classified as activation immunotherapies, while immunotherapies that reduce or suppress are classified as suppression immunotherapies. Immunotherapies are typically, but not always, biotherapeutic agents. Numerous immunotherapies are used to treat cancer. These include, but are not limited to, monoclonal antibodies, adoptive cell transfer, cytokines, chemokines, vaccines, and small molecule inhibitors.

The terms "biologic," "biologic drug," and "biological product" refer to a wide range of products such as vaccines, blood and blood components, allergenics, somatic cells, gene therapy, tissues, nucleic acids, and proteins. Biologics may include sugars, proteins, or nucleic acids, or complex combinations of these substances, or may be living entities, such as cells and tissues. Biologics may be isolated from a variety of natural sources (e.g., human, animal, microorganism) and may be produced by biotechnological methods and other technologies.

The term "small molecule" or "small molecule therapeutic" refers to molecules, whether naturally occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "chemotherapeutic agent" refers to a therapeutic agent known to be of use in chemotherapy for cancer.

A "hematological cancer" includes a cancer which affects a hematopoietic cell or tissue. Hematological cancers include cancers associated with aberrant hematological content and/or function. Examples of hematological cancers include, but are nor limited to, leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), chronic lymphocytic leukemia (CLL) (e.g., B-cell CLL, T-cell CLL)), lymphoma such as Hodgkin lymphoma (HL) (e.g., B-cell HL, T-cell HL), non-Hodgkin lymphoma (NHL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma, primary central nervous system (CNS) lymphoma, T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma), a mixture of one or more leukemia/lymphoma as described above, multiple myeloma, heavy chain disease (e.g., alpha chain disease, gamma chain disease, mu chain disease) acute non-lymphocytic leukemia (ANLL), acute promyelocytic leukemia (APL), acute myelomonocytic leukemia (AMMoL), polycythemia vera, Wilm's tumor, and Ewing's sarcoma.

The term "E3 ubiquitin ligase" or "E3 ligase" refers to any protein that recruits an E2 ubiquitin-conjugating enzyme that has been loaded with ubiquitin, recognizes a protein substrate, and assists or directly catalyzes the transfer of ubiquitin from the E2 protein to the protein substrate.

DETAILED DESCRIPTION OF CERTAIN EMBODIMENTS

Provided herein are bifunctional compounds that are inhibitors of MALT1 and recruit certain E3 ligases (e.g., Cereblon, VHL) to promote the degradation of MALT1. In one aspect, the disclosure provides compounds of Formula I, and pharmaceutically acceptable salts, solvates, hydrates, polymorphs, co-crystals, tautomers, stereoisomers, isotopically labeled derivatives, prodrugs, and pharmaceutical compositions thereof. The compounds are useful for the treatment and/or prevention of diseases associated with MALT1 activity (e.g., autoimmune disease, inflammatory disease, cancer (e.g., DLBCL)) in a subject in need thereof.

Compounds

The compounds described herein interact with MALT1 and an E3 ubiquitin ligase (e.g., Cereblon, VHL). As described herein, the therapeutic effect may be a result of inhibition, degradation, modulation, binding, or modification of MALT1 by a compound. The therapeutic effect may be a result of inhibition, modulation, binding, or modification of an E3 ubiquitin ligase (e.g., Cereblon, VHL), by a compound. The therapeutic effect may be a result of recruitment of an E3 ubiquitin ligase (e.g., Cereblon, VHL) by inhibition, modulation, binding, or modification of the E3 ubiquitin ligase to ubiquitinate MALT1 and mark it for proteasome degradation, by a compound. A compound may be provided for use in any composition, kit, or method described herein as a pharmaceutically acceptable salt, co-crystal, tautomer, stereoisomer, solvate, hydrate, polymorph, isotopically enriched derivative, or prodrug thereof.

In one aspect, disclosed is a compound of Formula I:

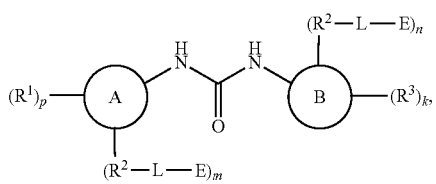

I or a pharmaceutically acceptable salt, co-crystal, tautomer, stereoisomer, solvate, hydrate, polymorph, isotopically enriched derivative, or prodrug thereof, wherein:

A is a fused bicyclic heteroaryl ring;

B is phenyl or pyridinyl;

each occurrence of $R^1$ and $R^3$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —$NO_2$, —$NR^A$C(=O)$R^A$, —$NR^A$C(=O)$OR^A$, —$NR^A$C(=O)N($R^A$)$_2$, —OC(=O)$R^A$, —OC(=O)$OR^A$, —OC(=O)N($R^A$)$_2$, or a nitrogen protecting group when attached to a nitrogen atom;

$R^2$ is substituted or unsubstituted alkylene, substituted or unsubstituted heterocyclylene, substituted or unsubstituted arylene, substituted or unsubstituted heteroarylene, substituted or unsubstituted heteroalkylene, substituted or unsubstituted alkylheteroarylene, substituted or unsubstituted heteroarylalkylene, —O—, —N($R^A$)—, —S—, —C(=O)—, —C(=O)O—, —C(=O)N$R^A$—, —$NR^A$C(=O)—, —$NR^A$C(=O)O—, —$NR^A$C(=O)N($R^A$)—, —OC(=O)—, —OC(=O)O—, or —OC(=O)N($R^A$)—;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring;

L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, —O—, —N($R^A$)—, —S—, —C(=O)—, —C(=O)O—, —C(=O)N$R^A$—, —$NR^A$C(=O)—, —$NR^A$C(=O)$R^A$—, —C(=O)$R^A$—, —$NR^A$C(=O)O—, —$NR^A$C(=O)N($R^A$)—, —OC(=O)—, —OC(=O)O—, or —OC(=O)N($R^A$)—, or a combination thereof; E is an E3 ubiquitin ligase binding moiety;

m and n are each independently 0 or 1, provided that m+n=1;

k is 0, 1, 2, 3, or 4; and p is 0, 1, 2, 3, or 4.

In certain embodiments of the compound of Formula I, A is a fused bicyclic heteroaryl ring;

B is phenyl or pyridinyl;

each occurrence of $R^1$ and $R^3$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —$NO_2$, —$NR^A$C(=O)$R^A$, —$NR^A$C(=O)$OR^A$, —$NR^A$C(=O)N($R^A$)$_2$, —OC(=O)$R^A$, —OC(=O)$OR^A$, —OC(=O)N($R^A$)$_2$, or a nitrogen protecting group when attached to a nitrogen atom;

$R^2$ is substituted or unsubstituted alkylene, substituted or unsubstituted heterocyclylene, substituted or unsubstituted arylene, substituted or unsubstituted heteroarylene, substituted or unsubstituted heteroalkylene, substituted or unsubstituted alkylheteroarylene, substituted or unsubstituted heteroarylalkylene, —O—, —N($R^A$)—, —S—, —C(=O)—, —C(=O)O—, —C(=O)N$R^A$—, —$NR^A$C(=O)—, —$NR^A$C(=O)O—, —$NR^A$C(=O)N($R^A$)—, —OC(=O)—, —OC(=O)O—, or —OC(=O)N($R^A$)—;

each occurrence of $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring;

L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, —O—, —N($R^A$)—, —S—, —C(=O)—, —C(=O)O—, —C(=O) N$R^A$—, —$NR^A$C(=O)—, —$NR^A$C(=O)$R^A$—, —C(=O)$R^A$—, —$NR^A$C(=O)O—, —$NR^A$C(=O)N($R^A$)—, —OC(=O)—, —OC(=O)O—, or —OC(=O)N($R^A$)—; E is an E3 ubiquitin ligase binding moiety;

m and n are each independently 0 or 1, provided that m+n=1;

k is 0, 1, 2, 3, or 4; and p is 0, 1, 2, 3, or 4.

In certain embodiments, A is a fused bicyclic heteroaryl ring. In certain embodiments, A is a fused bicyclic heteroaryl ring, wherein at least one atom in the ring is a heteroatom independently selected from nitrogen, oxygen, and sulfur. In certain embodiments, A is a fused bicyclic heteroaryl ring comprising at least one nitrogen atom. In certain embodiments, A is a fused bicyclic heteroaryl ring comprising at least two nitrogen atoms. In certain embodiments, A is a fused bicyclic heteroaryl ring comprising at least three nitrogen atoms. In certain embodiments, A is a monocyclic heteroaryl ring fused with phenyl. In certain embodiments, A is a 5-membered monocyclic heteroaryl ring fused with phenyl. In certain embodiments, A is a 6-membered monocyclic heteroaryl ring fused with phenyl. In certain embodiments, A is a monocyclic heteroaryl ring fused with another monocyclic heteroaryl. In certain embodiments, A is a 5-membered monocyclic heteroaryl ring fused with another 5-membered monocyclic heteroaryl. In certain embodiments, A is a 5-membered monocyclic heteroaryl ring fused with a 6-membered monocyclic heteroaryl. In certain embodiments, A is a 6-membered monocyclic heteroaryl ring fused with another 6-membered monocyclic heteroaryl. In certain embodiments, A is a 9-membered, fused bicyclic heteroaryl ring, wherein at least one atom in the ring is a heteroatom selected from nitrogen, oxygen, and sulfur. In certain embodiments, A is a 9-membered, fused bicyclic heteroaryl ring, wherein at least two atoms in the ring are heteroatoms independently selected from nitrogen, oxygen, and sulfur. In certain embodiments, A is a 9-membered, fused bicyclic heteroaryl ring, wherein at least three atoms in the ring are heteroatoms independently selected from nitrogen, oxygen, and sulfur. In certain embodiments, A is a 10-membered, fused bicyclic heteroaryl ring, wherein at least one atom in the ring is a heteroatom independently selected from nitrogen, oxygen, and sulfur. In certain embodiments, A is a 10-membered, fused bicyclic heteroaryl ring, wherein at least two atoms in the ring are heteroatoms independently selected from nitrogen, oxygen, and sulfur. In certain embodiments, A is a 10-membered, fused bicyclic heteroaryl ring, wherein at least three atoms in the ring are heteroatoms independently selected from nitrogen, oxygen, and sulfur.

In certain embodiments, A is of the formula:

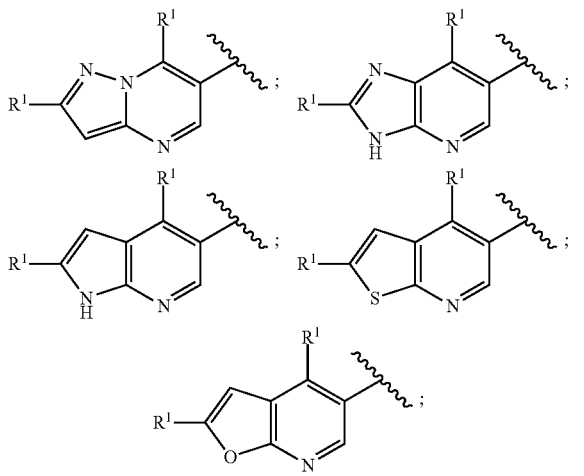

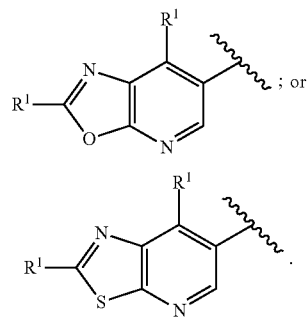

In certain embodiments, A is of the formula:

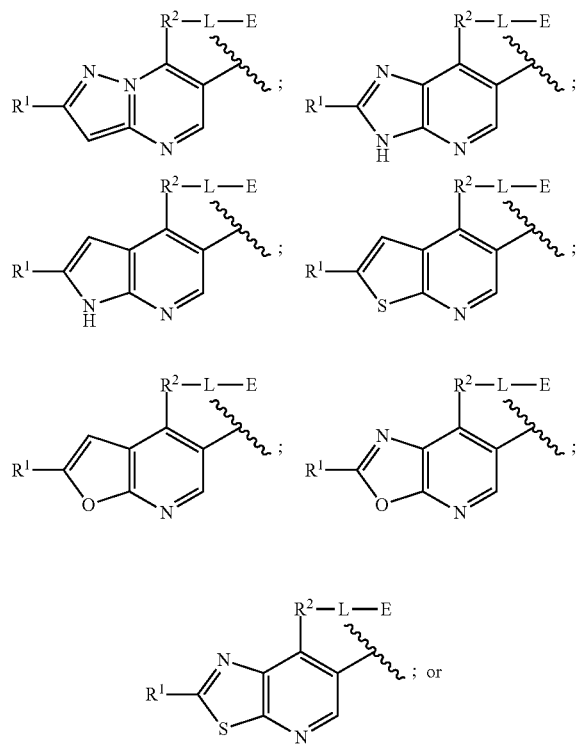

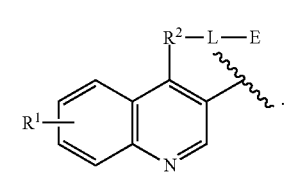

In certain embodiments, A is of the formula:

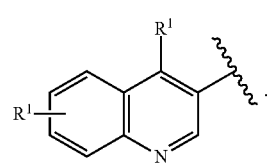

In certain embodiments, A is of the formula:

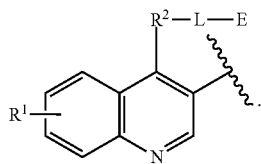

In certain embodiments, A is of the formula:

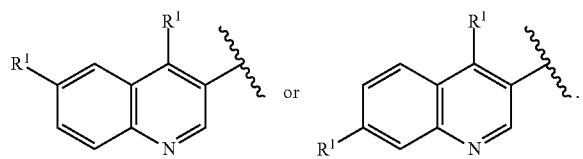

In certain embodiments, A is of the formula:

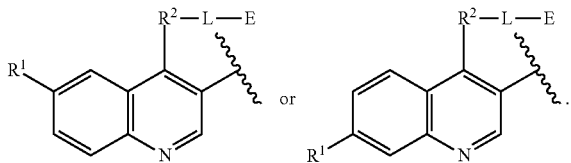

In certain embodiments, B is phenyl or pyridinyl. In certain embodiments, B is phenyl. In certain embodiments, B is pyridinyl.

In certain embodiments, B is of the formula:

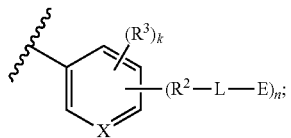

wherein X is N, CH, or $CR^3$.

In certain embodiments, B is of the formula:

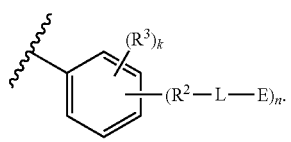

In certain embodiments, B is of the formula:

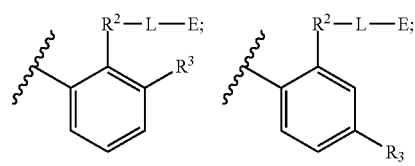

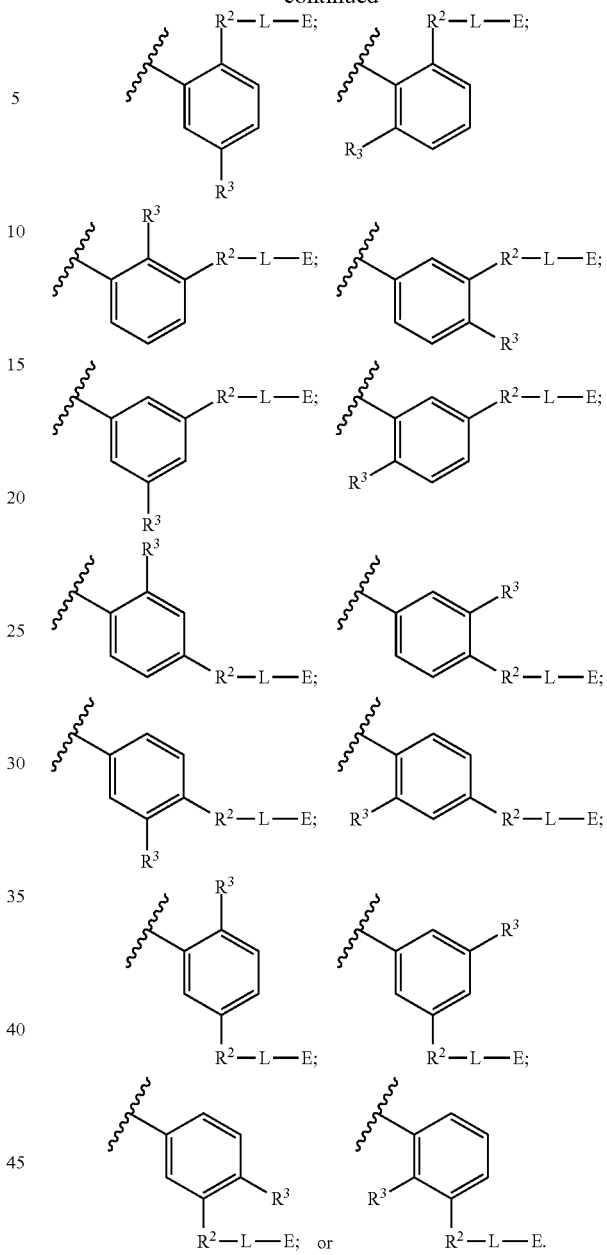

In certain embodiments, B is of the formula:

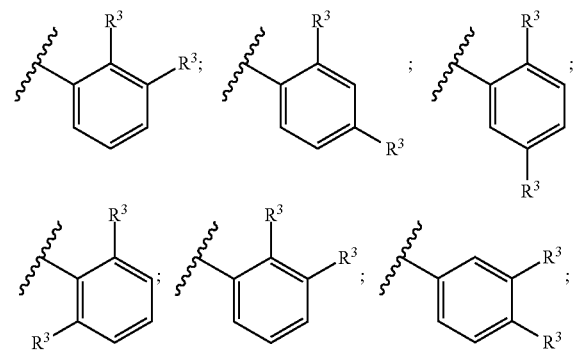

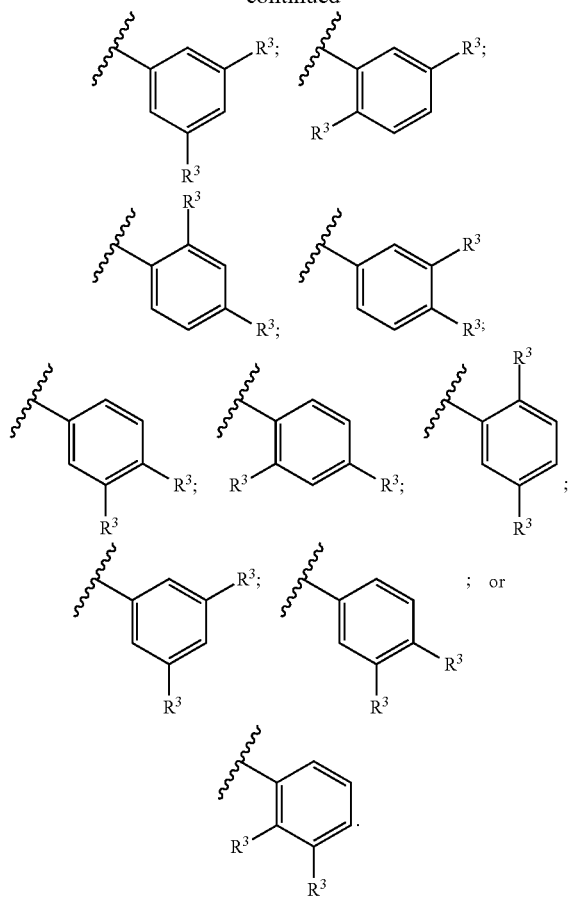

In certain embodiments, B is of the formula:

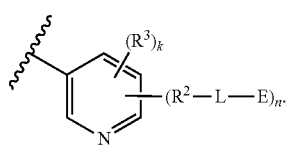

In certain embodiments, B is of the formula:

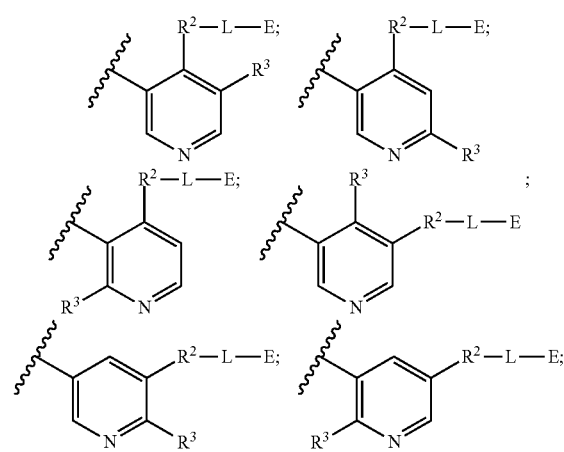

In certain embodiments, B is of the formula:

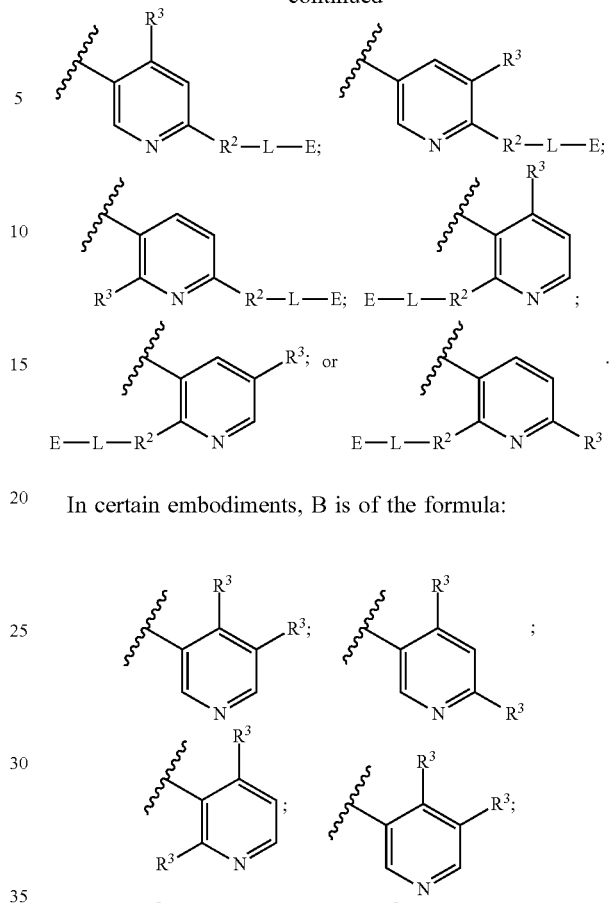

In certain embodiments, B is of the formula:

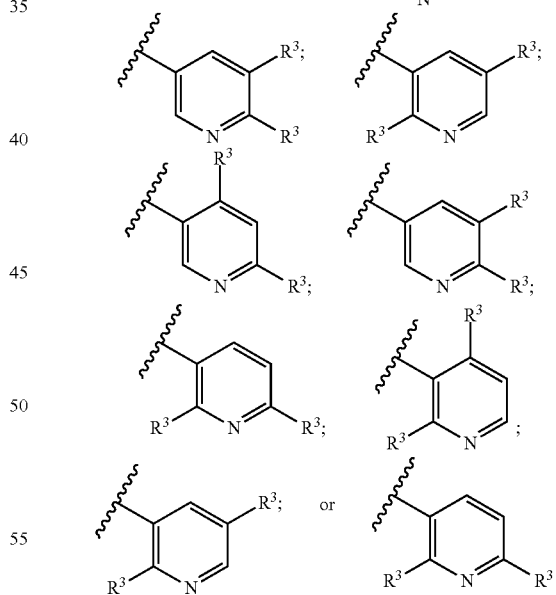

In certain embodiments, each occurrence of $R^1$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —C(=$NR^A$)$R^A$, —C(=$NR^A$)$OR^A$, —C(=$NR^A$)N $(R^A)_2$, —C(=O)$R^A$, —C(=O)O$R^A$, —C(=O)N$(R^A)_2$, —NO$_2$, —NR$^A$C(=O)$R^A$, —NR$^A$C(=O)O$R^A$, —NR$^A$C(=O)N$(R^A)_2$, —OC(=O)$R^A$, —OC(=O)O$R^A$, —OC(=O)N$(R^A)_2$, or a nitrogen protecting group when attached to a nitrogen atom.

In certain embodiments, each occurrence of $R^1$ is, independently, halogen, substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, or substituted or unsubstituted heteroalkyl. In certain embodiments, each occurrence of $R^1$ is, independently, halogen, substituted or unsubstituted alkyl, substituted or unsubstituted heteroaryl, or substituted or unsubstituted heteroalkyl.

In certain embodiments, each occurrence of $R^1$ is, independently, halogen or substituted or unsubstituted heteroaryl. In certain embodiments, each occurrence of $R^1$ is, independently, halogen or substituted or unsubstituted alkyl. In certain embodiments, each occurrence of $R^1$ is, independently, halogen or substituted or unsubstituted heteroalkyl. In certain embodiments, each occurrence of $R^1$ is, independently, substituted or unsubstituted alkyl, or substituted or unsubstituted heteroaryl. In certain embodiments, each occurrence of $R^1$ is, independently, substituted or unsubstituted heteroaryl or substituted or unsubstituted heteroalkyl.

In certain embodiments, each occurrence of $R^1$ is, independently, halogen or substituted or unsubstituted 5-membered heteroaryl. In certain embodiments, each occurrence of $R^1$ is, independently, halogen or substituted or unsubstituted $C_{1-6}$ alkyl. In certain embodiments, each occurrence of $R^1$ is, independently, halogen or substituted or unsubstituted $C_{1-6}$ heteroalkyl. In certain embodiments, each occurrence of $R^1$ is, independently, substituted or unsubstituted $C_{1-6}$ alkyl, or substituted or unsubstituted 5-membered heteroaryl. In certain embodiments, each occurrence of $R^1$ is, independently, substituted or unsubstituted 5-membered heteroaryl or substituted or unsubstituted $C_{1-6}$ heteroalkyl.

In certain embodiments, each occurrence of $R^1$ is, independently, Cl, Br, or unsubstituted 5-membered heteroaryl. In certain embodiments, each occurrence of $R^1$ is, independently, Cl or substituted $C_{1-6}$ alkyl. In certain embodiments, each occurrence of $R^1$ is, independently, Cl or substituted $C_{1-6}$ heteroalkyl. In certain embodiments, each occurrence of $R^1$ is, independently, substituted $C_{1-6}$ alkyl, or unsubstituted 5-membered heteroaryl. In certain embodiments, each occurrence of $R^1$ is, independently, unsubstituted 5-membered heteroaryl or substituted $C_{1-6}$ heteroalkyl. In certain embodiments, each occurrence of $R^1$ is, independently, Cl, Br, methyl, ethyl, isopropyl

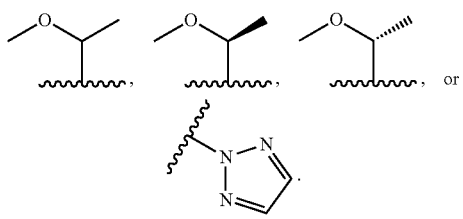

In certain embodiments, each occurrence of $R^1$ is, independently, Cl, Br, methyl, isopropyl,

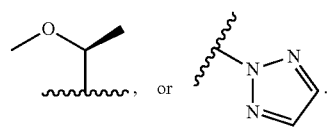

In certain embodiments, each occurrence of $R^1$ is, independently, Cl,

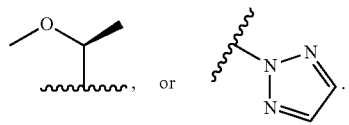

In certain embodiments, each occurrence of $R^1$ is, independently, Cl or

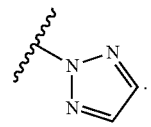

In certain embodiment, each occurrence of $R^1$ is, independently, Cl or

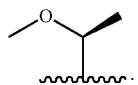 [SMILES: *[C@H](C)OC]

In certain embodiments, each occurrence of $R^1$ is, independently, Cl or isopropyl. In certain embodiments, each occurrence of $R^1$ is, independently, Cl, Br, or methyl.

In certain embodiments, each occurrence of $R^3$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —O$R^A$, —N$(R^A)_2$, —S$R^A$, —CN, —SCN, —C(=N$R^A$)$R^A$, —C(=N$R^A$)O$R^A$, —C(=N$R^A$)N$(R^A)_2$, —C(=O)$R^A$, —C(=O)O$R^A$, —C(=O)N$(R^A)_2$, —NO$_2$, —NR$^A$C(=O)$R^A$, —NR$^A$C(=O)O$R^A$, —NR$^A$C(=O)N$(R^A)_2$, —OC(=O)$R^A$, —OC(=O)O$R^A$, —OC(=O)N$(R^A)_2$, or a nitrogen protecting group when attached to a nitrogen atom.

In certain embodiments, each occurrence of $R^3$ is, independently, halogen, substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, or substituted or unsubstituted heteroalkyl. In certain embodiments, each occurrence of $R^3$ is, independently, halogen, substituted or unsubstituted alkyl, substituted or unsubstituted heteroaryl, or substituted or unsubstituted heteroalkyl.

In certain embodiments, each occurrence of $R^3$ is, independently, halogen or substituted or unsubstituted heteroaryl. In certain embodiments, each occurrence of $R^3$ is, independently, halogen or substituted or unsubstituted alkyl.

In certain embodiments, each occurrence of $R^3$ is, independently, halogen or substituted or unsubstituted heteroalkyl. In certain embodiments, each occurrence of $R^3$ is, independently, substituted or unsubstituted alkyl, or substituted or unsubstituted heteroaryl. In certain embodiments, each occurrence of $R^3$ is, independently, substituted or unsubstituted heteroaryl or substituted or unsubstituted heteroalkyl.

In certain embodiments, each occurrence of $R^3$ is, independently, halogen or substituted or unsubstituted 5-membered heteroaryl. In certain embodiments, each occurrence of $R^3$ is, independently, halogen or substituted or unsubstituted $C_{1-6}$ alkyl. In certain embodiments, each occurrence of $R^3$ is, independently, halogen or substituted or unsubstituted $C_{1-6}$ heteroalkyl. In certain embodiments, each occurrence of $R^3$ is, independently, substituted or unsubstituted $C_{1-6}$ alkyl, or substituted or unsubstituted 5-membered heteroaryl. In certain embodiments, each occurrence of $R^3$ is, independently, substituted or unsubstituted 5-membered heteroaryl or substituted or unsubstituted $C_{1-6}$ heteroalkyl.

In certain embodiments, each occurrence of $R^3$ is, independently, Cl, Br, or unsubstituted 5-membered heteroaryl. In certain embodiments, each occurrence of $R^3$ is, independently, Cl or substituted $C_{1-6}$ alkyl. In certain embodiments, each occurrence of $R^3$ is, independently, Cl or substituted $C_{1-6}$ heteroalkyl. In certain embodiments, each occurrence of $R^3$ is, independently, substituted $C_{1-6}$ alkyl, or unsubstituted 5-membered heteroaryl. In certain embodiments, each occurrence of $R^3$ is, independently, unsubstituted 5-membered heteroaryl or substituted $C_{1-6}$ heteroalkyl. In certain embodiments, each occurrence of $R^3$ is, independently, Cl, Br, methyl, ethyl, isopropyl

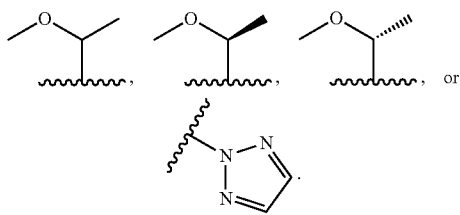

In certain embodiments, each occurrence of $R^3$ is, independently, Cl, Br, methyl, isopropyl,

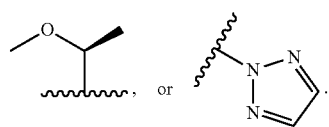

In certain embodiments, each occurrence of $R^3$ is, independently, Cl,

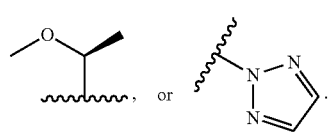

In certain embodiments, each occurrence of $R^3$ is, independently, Cl or

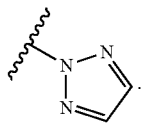

In certain embodiments, each occurrence of $R^3$ is, independently, Cl or

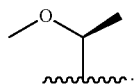

In certain embodiments, each occurrence of $R^3$ is, independently, Cl or isopropyl. In certain embodiments, each occurrence of $R^3$ is, independently, Cl, Br, or methyl.

In certain embodiments, each occurrence of $R^1$ is Cl; and each occurrence of $R^3$ is, independently, Cl or

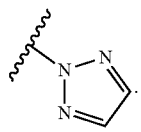 [SMILES: *n1nccn1]

In certain embodiments, each occurrence of $R^1$ is, independently, Cl or

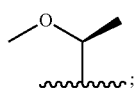 [SMILES: *[C@H](C)OC]

and each occurrence of $R^3$ is Cl. In certain embodiments, each occurrence of $R^1$ is, independently, Cl or isopropyl; and each occurrence of $R^3$ is Cl. In certain embodiments, each occurrence of $R^1$ is, independently, Cl or methyl; and each occurrence of $R^3$ is Cl.

$R^2$ is a divalent moiety linking A to L or linking B to L. In certain embodiments, $R^2$ is substituted or unsubstituted alkylene, substituted or unsubstituted heterocyclylene, substituted or unsubstituted arylene, substituted or unsubstituted heteroarylene, substituted or unsubstituted heteroalkylene, substituted or unsubstituted alkylheteroarylene, substituted or unsubstituted heteroarylalkylene, —O—, —N($R^4$)—, —S—, —C(=O)—, —C(=O)O—, —C(=O)N$R^4$—, —N$R^4$C(=O)—, —N$R^4$C(=O)O—, —N$R^4$C(=O)N($R^4$)—, —OC(=O)—, —OC(=O)O—, or —OC(=O)N($R^4$)—.

In certain embodiments, $R^2$ is substituted or unsubstituted alkylene, substituted or unsubstituted heterocyclylene, substituted or unsubstituted heteroarylene, substituted or unsubstituted heteroalkylene, substituted or unsubstituted alkylheteroarylene, or —O—. In certain embodiments, $R^2$ is substituted or unsubstituted $C_{1-6}$ alkylene, substituted or unsubstituted 6-membered heterocyclylene, substituted or unsubstituted 5-membered heteroarylene, substituted or unsubstituted $C_{1-6}$ heteroalkylene, substituted or unsubstituted $C_{1-6}$ alkylheteroarylene, or —O—.

In certain embodiments, $R^2$ is substituted or unsubstituted $C_{1-4}$ alkylene. In certain embodiments, $R^2$ is unsubstituted $C_{1-4}$ alkylene. In certain embodiments, $R^2$ is

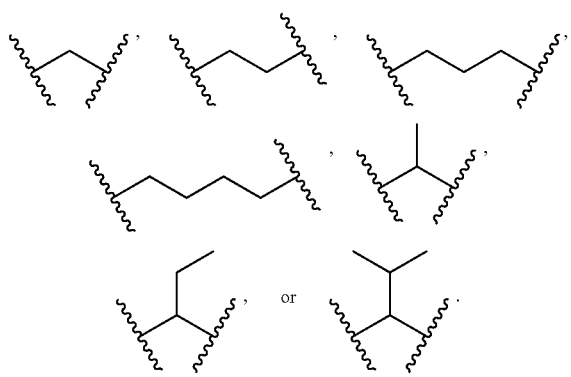

In certain embodiments, $R^2$ is

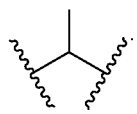

In certain embodiments, $R^2$ is

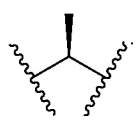

In certain embodiments, $R^2$ is

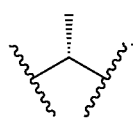

In certain embodiments, $R^2$ is substituted or unsubstituted $C_{1-4}$ alkylheteroarylene, wherein the heteroarylene is a 5-membered ring comprising at least one nitrogen. In certain embodiments, $R^2$ is substituted or unsubstituted $C_{1-4}$ alkylheteroarylene, wherein the heteroarylene is a 5-membered ring comprising at least two nitrogen. In certain embodiments, $R^2$ is

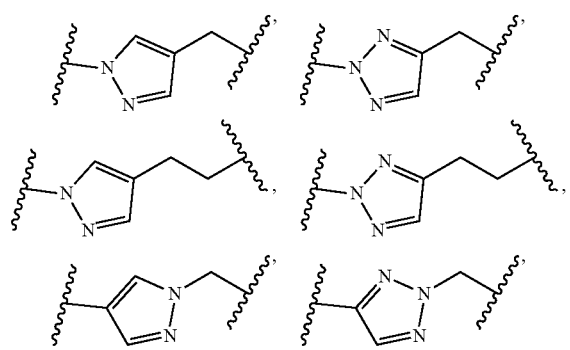

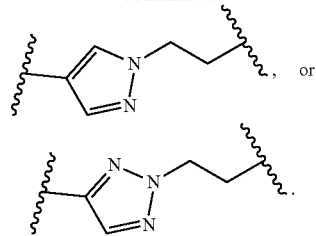

In certain embodiments, $R^2$ is

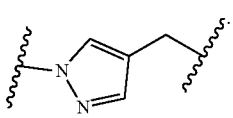 [SMILES: *Cc1cnn(*)c1]

In certain embodiments, $R^2$ is substituted or unsubstituted heteroalkylene. In certain embodiments, $R^2$ is substituted or unsubstituted $C_{1-6}$ heteroalkylene. In certain embodiments, $R^2$ is substituted or unsubstituted $C_{1-4}$ heteroalkylene. In certain embodiments, $R^2$ is

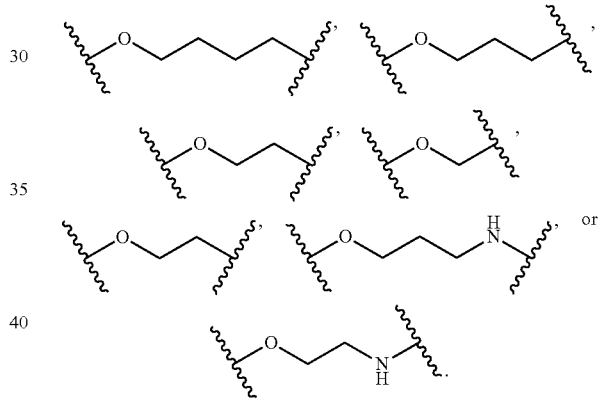

In certain embodiments, $R^2$ is

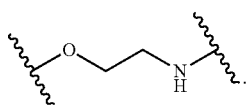 [SMILES: *NCCO*]

In certain embodiments, $R^2$ is

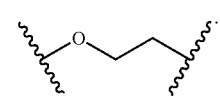

In certain embodiments, $R^2$ is substituted or unsubstituted heterocyclylene. In certain embodiments, $R^2$ is substituted or unsubstituted 6-membered heterocyclylene. In certain embodiments, $R^2$ is substituted or unsubstituted 6-membered heterocyclylene comprising 1 or 2 nitrogen atoms in the ring. In certain embodiments, $R^2$ is

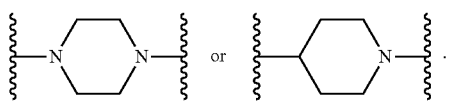

In certain embodiments, R² is

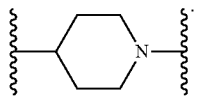

In certain embodiments, R² is

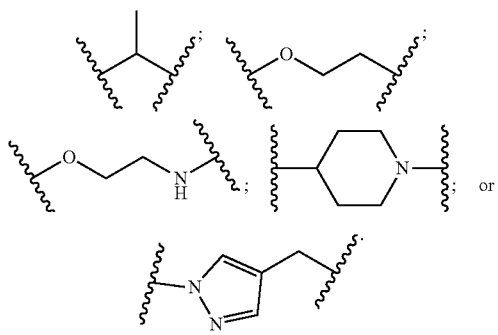

In certain embodiments, R² is

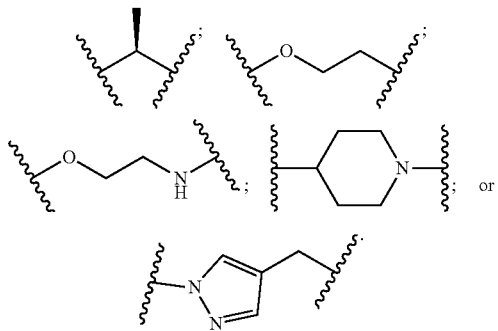

In certain embodiments, R² is

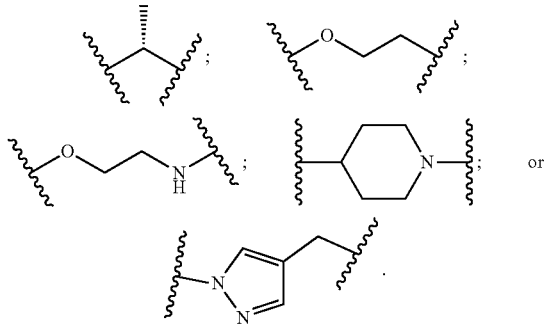

L is a divalent moiety linking R and E. In certain embodiments, L is any "L" group recited in U.S. patent application U.S. Ser. No. 14/792,414, filed Jul. 6, 2015, which is incorporated herein by reference. In certain embodiments, L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, —O—, —N(R$^A$)—, —S—, —C(=O)—, —C(=O)O—, —NR$^A$C(=O)R$^A$—, —C(=O)R$^A$—, —C(=O)NR$^A$—, —NR$^A$C(=O)—, —NR$^A$C(=O)O—, —NR$^A$C(=O)N(R$^A$)—, —OC(=O)—, —OC(=O)O—, or —OC(=O)N(R$^A$)—, or a combination thereof.

In certain embodiments, L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, —O—, —N(R$^A$)—, —S—, —C(=O)—, —C(=O)O—, —NR$^A$C(=O)R$^A$—, —C(=O)R$^A$—, —C(=O)NR$^A$—, —NR$^A$C(=O)—, —NR$^A$C(=O)O—, —NR$^A$C(=O)N(R$^A$)—, —OC(=O)—, —OC(=O)O—, or —OC(=O)N(R$^A$)—.

In certain embodiments, L is substituted or unsubstituted alkylene, substituted or unsubstituted alkenylene, substituted or unsubstituted heterocyclylene, substituted or unsubstituted heteroarylene, substituted or unsubstituted heteroalkylene, —O—, —N(R$^A$)—, —S—, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, or —OC(=O)N(R$^A$)—.

In certain embodiments, L is substituted or unsubstituted alkylene, substituted or unsubstituted heteroalkylene, —O—, —C(=O)NR$^A$—, —NR$^A$C(=O)R$^A$—, —C(=O)R$^A$—, or —NR$^A$C(=O)—. In certain embodiments, L is a substituted or unsubstituted C$_{1-30}$ heteroalkylene. In certain embodiments, L is a substituted or unsubstituted C$_{1-20}$ heteroalkylene. In certain embodiments, L is —NR$^A$C(=O)R$^A$— or —C(=O)R$^A$—; wherein R$^A$ is independently hydrogen, substituted or unsubstituted alkylene, or substituted or unsubstituted heteroalkylene.

In certain embodiments, L is

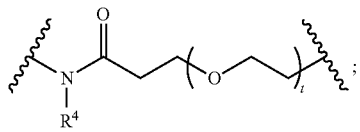

R$^4$ is hydrogen or C$_{1-6}$ alkyl; and t is 0, 1, 2, 3, 4, 5, or 6. In certain embodiments, R$^4$ is hydrogen or C$_{1-4}$ alkyl; and t is 0, 1, 2, 3, 4, 5, or 6. In certain embodiments, R$^4$ is hydrogen or C$_{1-2}$ alkyl; and t is 0, 1, 2, 3, 4, 5, or 6. In certain embodiments, R$^4$ is hydrogen or methyl; and t is 0, 1, 2, 3, 4, 5, or 6. In certain embodiments, R$^4$ is hydrogen or methyl; and t is 2 or 4. In certain embodiments, R$^4$ is hydrogen; and t is 2. In certain embodiments, R$^4$ is hydrogen; and t is 4. In certain embodiments, R$^4$ is methyl; and t is 2. In certain embodiments, R$^4$ is methyl; and t is 4.

In certain embodiments, L is

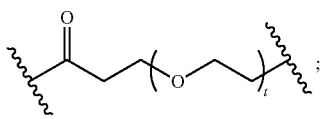

and t is 0, 1, 2, 3, 4, 5, or 6. In certain embodiments, t is 2 or 4.

In certain embodiments, L is

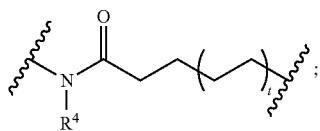

$R^4$ is hydrogen or $C_{1-6}$ alkyl; and t is 0, 1, 2, 3, 4, 5, or 6. In certain embodiments, $R^4$ is hydrogen or $C_{1-4}$ alkyl; and t is 0, 1, 2, 3, 4, 5, or 6. In certain embodiments, $R^4$ is hydrogen or $C_{1-2}$ alkyl; and t is 0, 1, 2, 3, 4, 5, or 6. In certain embodiments, $R^4$ is hydrogen or methyl; and t is 0, 1, 2, 3, 4, 5, or 6. In certain embodiments, $R^4$ is hydrogen; and t is 3. In certain embodiments, $R^4$ is methyl; and t is 3.

In certain embodiments, L comprises one or more group selected from the group consisting of substituted or unsubstituted heterocyclylene, substituted or unsubstituted arylene, substituted or unsubstituted heteroalkylene, —O—, —N($R^A$)—, —S—, —C(=O)—, —C(=O)O—, —$NR^A$C(=O)$R^A$—, —C(=O)$R^A$—, —C(=O)$NR^A$—, —$NR^A$C(=O)—, —$NR^A$C(=O)O—, —$NR^A$C(=O)N($R^A$)—, —OC(=O)—, —OC(=O)O—, and —OC(=O)N($R^A$)—. In certain embodiments, L comprises one or more group selected from the group consisting of substituted or unsubstituted heterocyclylene, substituted or unsubstituted arylene, substituted or unsubstituted heteroalkylene, —$NR^A$C(=O)$R^A$—, —C(=O)$R^A$—, —C(=O)$NR^A$—, —$NR^A$C(=O)—, —$NR^A$C(=O)O—, and —$NR^A$C(=O)N($R^A$).

In certain embodiments, L is

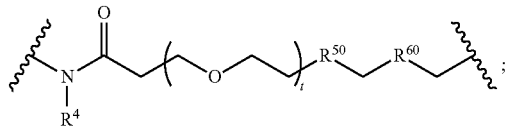

wherein $R^4$ is hydrogen or $C_{1-6}$ alkyl; t is 0, 1, 2, 3, 4, 5, or 6; $R^{50}$ is substituted or unsubstituted heterocyclylene, or substituted or unsubstituted arylene; and $R^{60}$ is substituted or unsubstituted heterocyclylene, or substituted or unsubstituted arylene. In certain embodiments, $R^4$ is hydrogen or $C_{1-4}$ alkyl; t is 0, 1, 2, 3, 4, 5, or 6; $R^{50}$ is substituted or unsubstituted heterocyclylene; and $R^{60}$ is substituted or unsubstituted arylene. In certain embodiments, $R^4$ is hydrogen or $C_{1-2}$ alkyl; t is 0, 1, 2, 3, 4, 5, or 6; $R^{50}$ is substituted or unsubstituted heterocyclylene; and $R^{60}$ is substituted or unsubstituted arylene. In certain embodiments, $R^4$ is hydrogen or methyl; t is 0, 1, 2, 3, 4, 5, or 6; $R^{50}$ is unsubstituted heterocyclylene; and $R^{60}$ is unsubstituted arylene. In certain embodiments, $R^4$ is hydrogen; t is 3; $R^{50}$ is unsubstituted heterocyclylene; and $R^{60}$ is unsubstituted arylene. In certain embodiments, $R^4$ is methyl; t is 3; $R^{50}$ is unsubstituted heterocyclylene; and $R^{60}$ is unsubstituted arylene.

In certain embodiments, L is

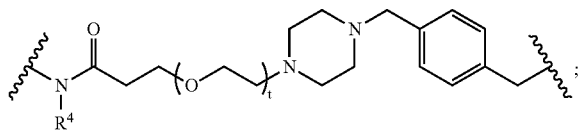

wherein $R^4$ is hydrogen or $C_{1-6}$ alkyl; and t is 0, 1, 2, 3, 4, 5, or 6. In certain embodiments, t is 2 or 4.

In certain embodiments, L is:

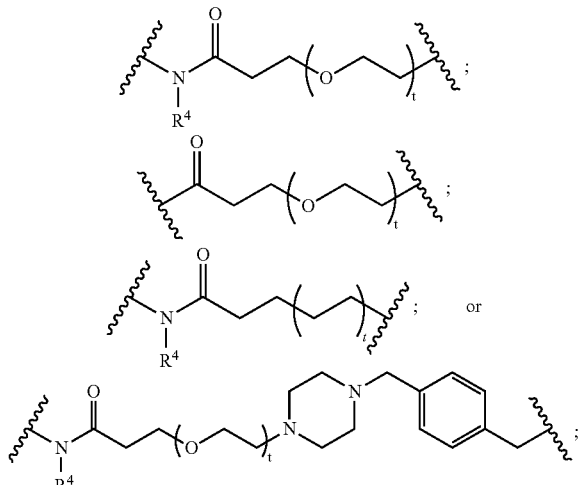

$R^4$ is hydrogen or $C_{1-6}$ alkyl; and t is 0, 1, 2, 3, 4, 5, or 6.

In certain embodiments, —$R^2$-L- is:

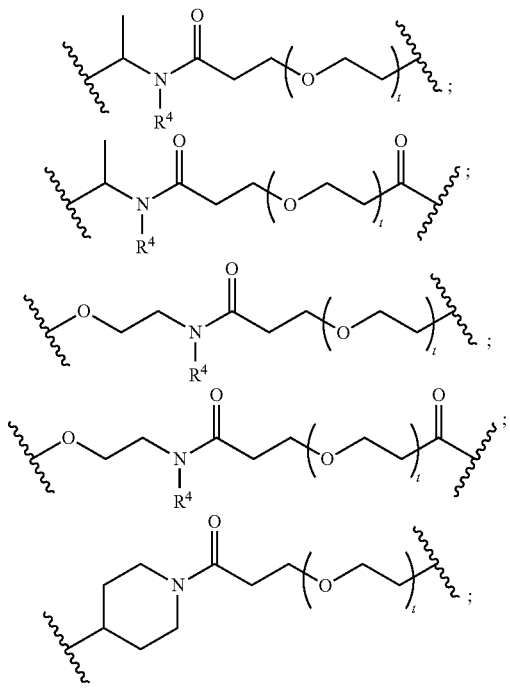

-continued
$R^4$ is hydrogen or $C_{1-6}$ alkyl; and t is 0, 1, 2, 3, 4, 5, or 6.
In certain embodiments, —$R^2$-L- is:
In certain embodiments, —$R^2$-L- is
$R^4$ is hydrogen or $C_{1-6}$ alkyl; and t is 0, 1, 2, 3, 4, 5, or 6.

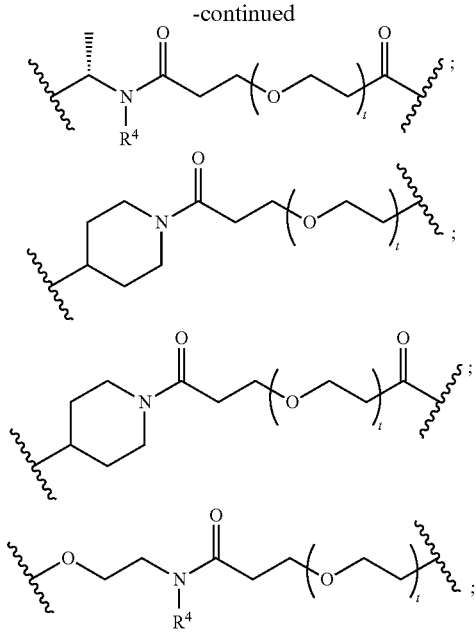
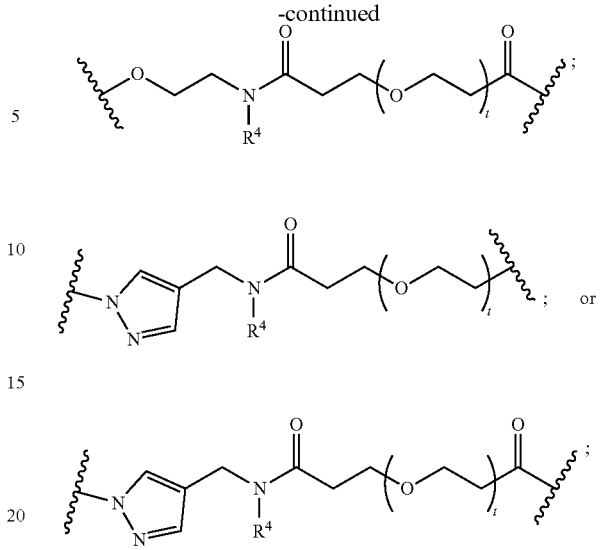
$R^4$ is hydrogen or $C_{1-6}$ alkyl; and t is 0, 1, 2, 3, 4, 5, or 6.
In certain embodiments, —$R^2$-L- is
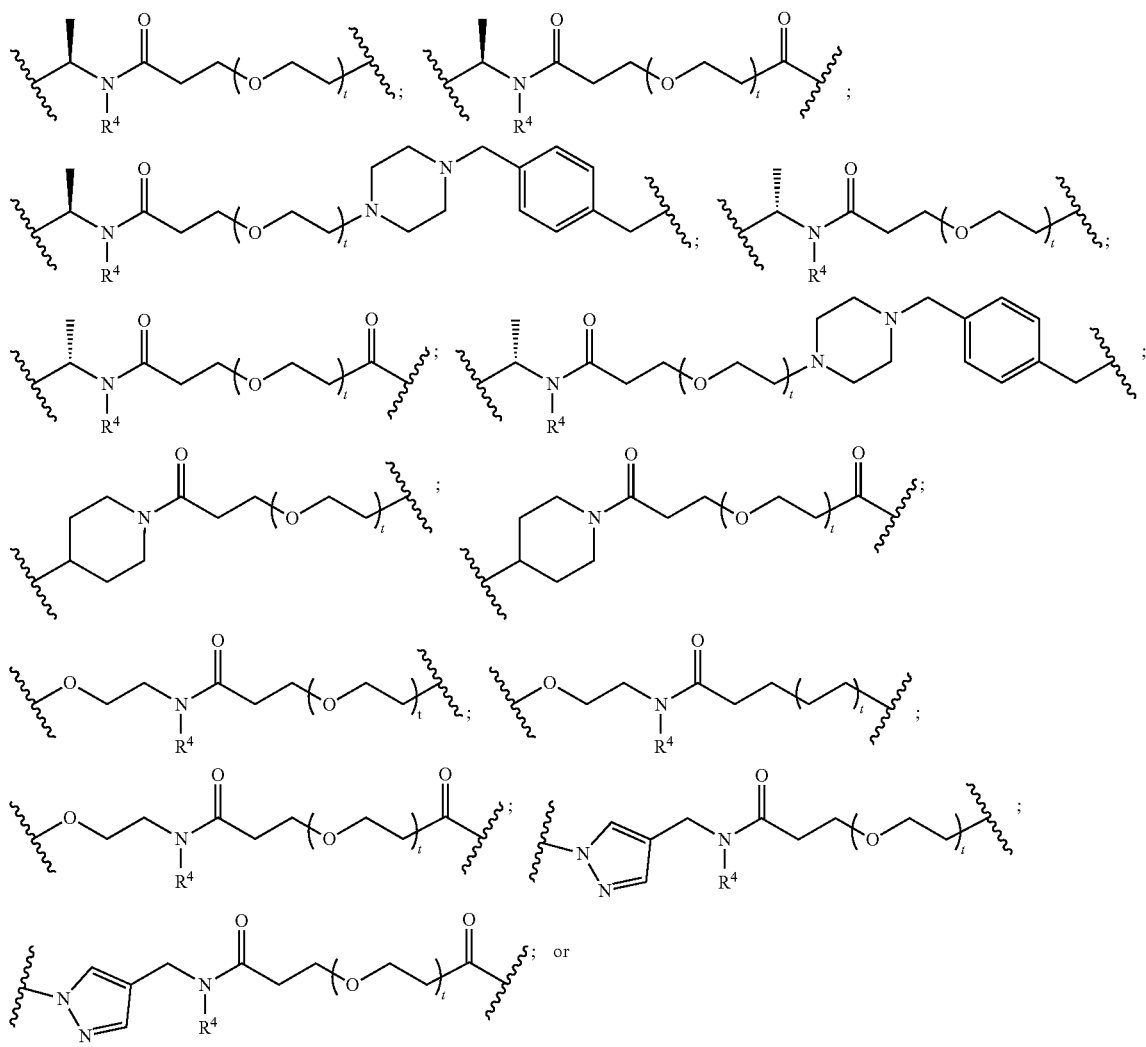

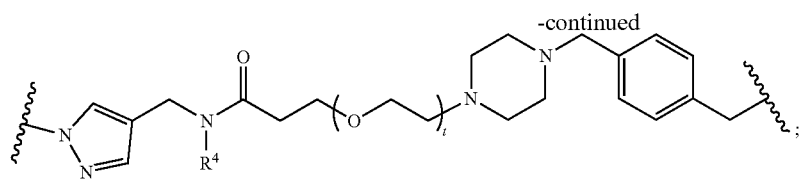

$R^4$ is hydrogen or $C_{1-6}$ alkyl; and t is 0, 1, 2, 3, 4, 5, or 6.

In certain embodiments, —$R^2$-L- is

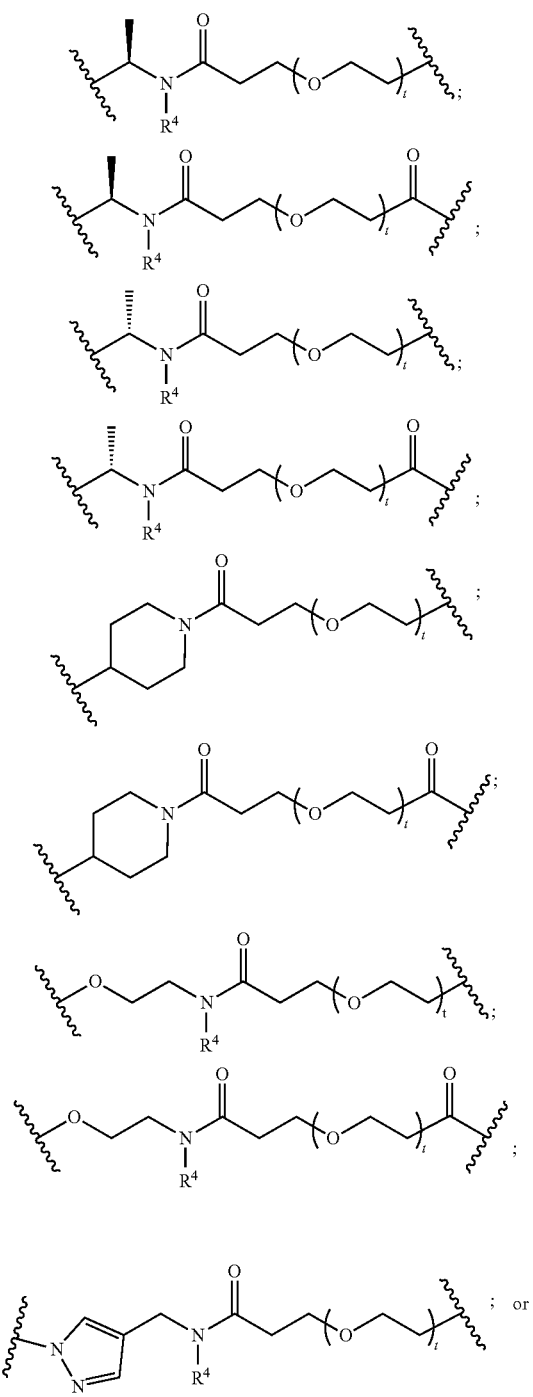

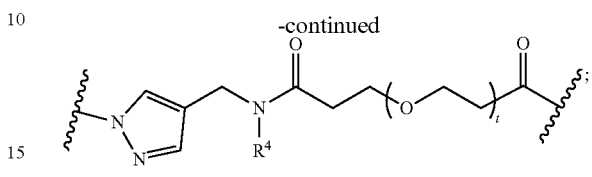

$R^4$ is hydrogen or $C_{1-2}$ alkyl; and t is 2 or 4.

In certain embodiments, $R^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^A$ groups are joined to form a substituted or unsubstituted heterocyclic ring. In certain embodiments, $R^A$ is, independently, hydrogen, substituted or unsubstituted alkyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or two $R^A$ groups are joined to form a substituted or unsubstituted heterocyclic ring. In certain embodiments, $R^A$ is, independently, hydrogen, substituted or unsubstituted alkyl, substituted or unsubstituted heteroalkyl, substituted or unsubstituted heterocyclyl, substituted or unsubstituted aryl, substituted or unsubstituted heteroaryl, or two $R^A$ groups are joined to form a substituted or unsubstituted heterocyclic ring. In certain embodiments, $R^A$ is, independently, hydrogen, substituted or unsubstituted $C_{1-6}$ alkyl, substituted or unsubstituted heteroalkyl, substituted or unsubstituted 5-6 membered heterocyclyl, substituted or unsubstituted phenyl, substituted or unsubstituted 5-6 membered heteroaryl, or two $R^A$ groups are joined to form a substituted or unsubstituted heterocyclic ring. In certain embodiments, $R^A$ is, independently, hydrogen, substituted or unsubstituted $C_{1-6}$ alkyl, substituted or unsubstituted $C_{1-30}$ heteroalkyl, substituted or unsubstituted 5-6 membered heterocyclyl, substituted or unsubstituted phenyl, substituted or unsubstituted 5-6 membered heteroaryl, or two $R^A$ groups are joined to form a substituted or unsubstituted heterocyclic ring. In certain embodiments, $R^A$ is, independently, hydrogen, substituted or unsubstituted $C_{1-6}$ alkyl, or substituted or unsubstituted $C_{1-30}$ heteroalkyl. In certain embodiments, $R^A$ is, independently, hydrogen, substituted or unsubstituted $C_{1-6}$ alkyl, or substituted or unsubstituted $C_{1-20}$ heteroalkyl.

In certain embodiments, k is 0, 1, 2, 3, or 4. In certain embodiments, k is 0, 1, 2, or 3. In certain embodiments, k is 0, 1, or 2. In certain embodiments, k is 0 or 1. In certain embodiments, k is 1 or 2.

In certain embodiments, p is 0, 1, 2, 3, or 4. In certain embodiments, p is 0, 1, 2, or 3. In certain embodiments, p is 0, 1, or 2. In certain embodiments, p is 0 or 1. In certain embodiments, p is 1 or 2.

In certain embodiments, k is 0, 1, or 2; and p is 0, 1, or 2. In certain embodiments, k is 1 or 2; and p is 0 or 1. In certain embodiments, k is 0 or 1; and p is 1 or 2. In certain embodiments, k is 1; and p is 2. In certain embodiments, k is 2; and p is 1.

E is an E3 ubiquitin ligase binding moiety. E is inclusive of all moieties that bind, or can bind, any E3 ubiquitin ligase. For example, in certain embodiments, E is capable of binding an E3 ubiquitin ligase, such as Cereblon; and, in other embodiments, E is capable of binding an E3 ubiquitin ligase, such as VHL. In certain embodiments, E is capable of binding to multiple different E3 ubiquitin ligases. In certain embodiments, E binds to Cereblon. In certain embodiments, E binds to VHL.

Recently, small molecules have been discovered that bind Cereblon. These drugs include the immunomodulatory agents thalidomide, lenalidomide, and pomalidomide, which are useful in the treatment of multiple myeloma and myelodysplastic syndromes, and are currently being clinically evaluated in a variety of lymphoid malignancies, including diffuse large B-cell lymphoma (DLBCL). Studies have confirmed that Cereblon is a target for lenalidomide and pomalidomide in both multiple myeloma and activated B-cell diffuse large B-cell lymphoma (ABC-DLBCL). In DLBCL cell lines, lenalidomide treatment was found to preferentially suppress proliferation of ABC-DLBCL cells in vitro and delay tumor growth in a human tumor xenograft model, with minimal effect on non-ABC-DLBCL cells.

Human Cereblon (CRBN) is a protein of 442 amino acids with an apparent molecular weight of ~51 kDa. (For the CRBN protein sequence see: Higgins et al., *Neurology.* 2004, 63, 1927-31. For additional information related to the CRBN structure see Hartmann et al., *PLoS One.* 2015, 10, e0128342.) Human CRBN contains the N-terminal part (237-amino acids from 81 to 317) of ATP-dependent Lon protease domain without the conserved Walker A and Walker B motifs, 11 casein kinase II phosphorylation sites, 4 protein kinase C phosphorylation sites, 1 N-linked glycosylation site and 2 myristoylation sites. CRBN is widely expressed in testis, spleen, prostate, liver, pancreas, placenta, kidney, lung, skeletal muscle, ovary, small intestine, peripheral blood leukocyte, colon, brain and retina where CRBN is located in cytoplasm, nucleus and peripheral membrane. (Chang et al., *Int. J. Biochem. Mol. Biol.* 2011, 2, 287-94.)

In certain embodiments, E is a modulator, binder, inhibitor, or ligand of Cereblon. In certain embodiments, E is a modulator of Cereblon. In certain embodiments, E is a binder of Cereblon. In certain embodiments, E is an inhibitor of Cereblon. In certain embodiments, E is a ligand of Cereblon. In certain embodiments, E is any modulator, binder, inhibitor, or ligand of Cereblon disclosed in U.S. patent application U.S. Ser. No. 14/792,414, filed Jul. 6, 2015, and International Patent Application, PCT/US2013/054663, filed Aug. 13, 2013, both of which are incorporated herein by reference. In certain embodiments, E is a modulator, binder, inhibitor, or ligand of a Cereblon variant. In certain embodiments, E is a modulator, binder, inhibitor, or ligand of a Cereblon isoform.

In certain embodiments, E comprises a heteroaryl ring. In certain embodiments, E comprises a fused bicyclic heteroaryl ring. In certain embodiments, E comprises a fused bicyclic heteroaryl ring and a heterocyclic ring. In certain embodiments, E comprises a phthalimido group, or an analogue or derivative thereof. In certain embodiments, E comprises a phthalimido-glutarimide group, or an analogue or derivative thereof. In certain embodiments, E is thalidomide, lenalidomide, pomalidomide, CC-885 (Matyskiela et al., *Nature* 2016, 535, 252-257), 3-(5-amino-2-methyl-4-oxoquinazolin-3(4H)-yl)piperidine-2,6-dione, or an analogue or derivative thereof.

In certain embodiments, E is

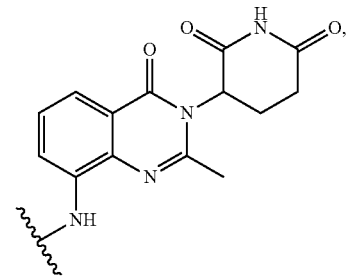

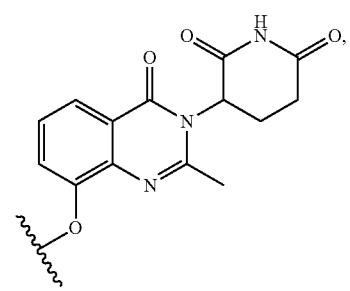

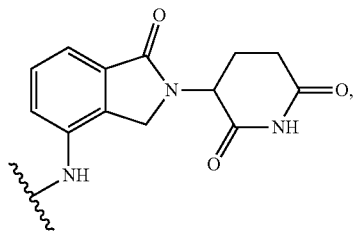

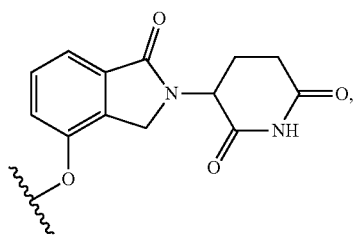

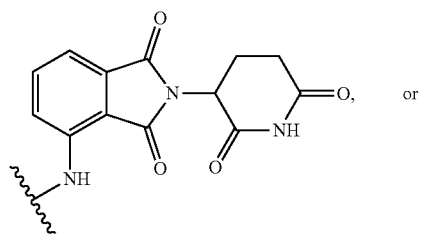

or

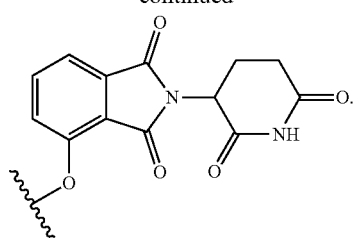
In certain embodiments, E is
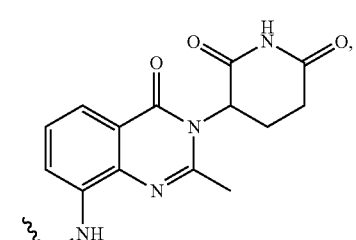
In certain embodiments, E is
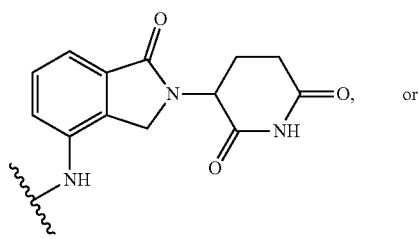
In certain embodiments, E is
In certain embodiments, E is
In certain embodiments, E is In certain embodiments, E is
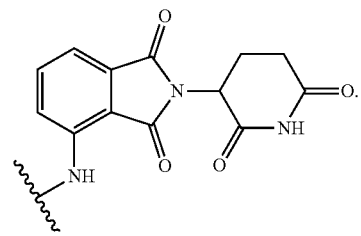 [SMILES: *Nc1cccc2c1C(=O)N(C1CCC(=O)NC1=O)C2=O]
In certain embodiments, E is
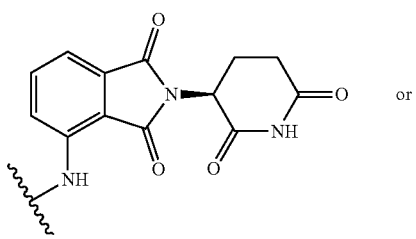 or
In certain embodiments, E is
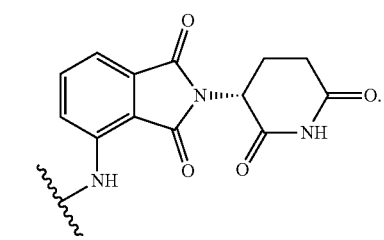
In certain embodiments, E is
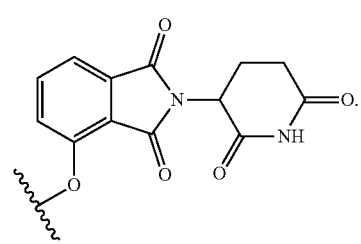 [SMILES: *Oc1cccc2c1C(=O)N(C1CCC(=O)NC1=O)C2=O]
In certain embodiments, E is
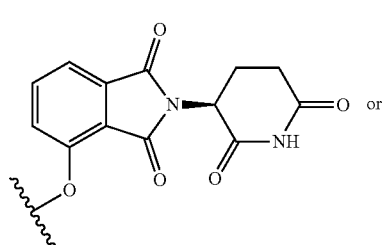 or
In certain embodiments, E is
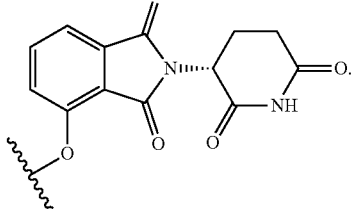
In certain embodiments, E is
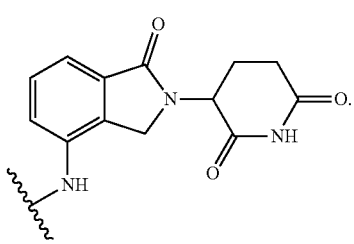 [SMILES: *Nc1cccc2c1CN(C1CCC(=O)NC1=O)C2=O]
In certain embodiments, E is
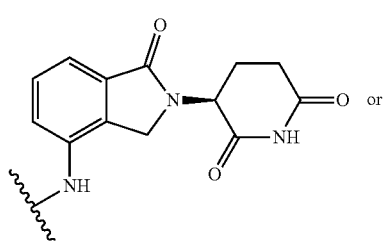 or
In certain embodiments, E is
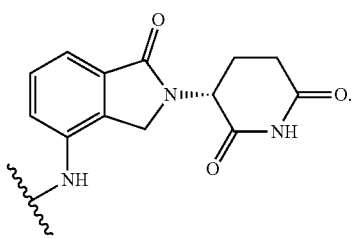
In certain embodiments, E is
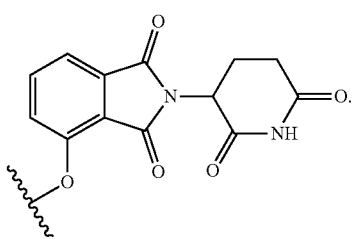 [SMILES: *Oc1cccc2c1C(=O)N(C1CCC(=O)NC1=O)C2=O]

In certain embodiments, E is

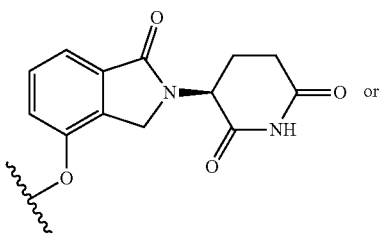

or

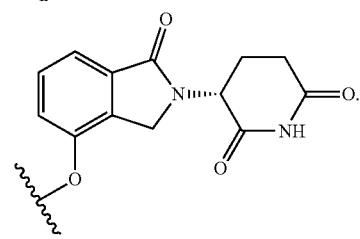

The full-length von Hippel-Lindau tumor suppressor protein (VHL) contains 213 amino acids. (For the VHL protein sequence see: Duan et al., *Proc. Natl. Acad. Sci. U.S.A.* 1995, 92, 6459-63. For additional information related to the VHL structure see Stebbins et al., *Science* 1999, 284, 455-61 and Minervini et al., *Sci. Rep.* 2015, 5, 12605.) A second VHL-gene product arises by internal translation initiation from the codon 54 methionine, producing a 160 amino-acid protein ("pVHL19"). VHL has two main structural domains: an N-terminal domain composed mainly of β-sheets (β-domain) and a smaller C-terminal domain between amino acids 155-192 composed mainly of α helices (α-domain). The α-domain consists of three α helices that combines with a fourth α helix donated by elongin C. The β-domain is on the opposite side of the α domain and is free to contact other protein.

In certain embodiments, E is a modulator, binder, inhibitor, or ligand of VHL. In certain embodiments, E is a modulator of VHL. In certain embodiments, E is a binder of VHL. In certain embodiments, E is an inhibitor of VHL. In certain embodiments, E is a ligand of Cereblon. In certain embodiments, E is any ligand of VHL listed in Galdeano, C. et al. *J. Med. Chem.* 2014, 57, 8657, which is incorporated herein by reference. In certain embodiments, E is a modulator, binder, inhibitor, or ligand of a VHL variant. In certain embodiments, E is a modulator, binder, inhibitor, or ligand of a VHL isoform. In certain embodiments, E is a modulator, binder, inhibitor, or ligand of a VHL gene-product (e.g., pVHL19).

In certain embodiments, E comprises a peptide backbone structure. In certain embodiments, E is of the formula:

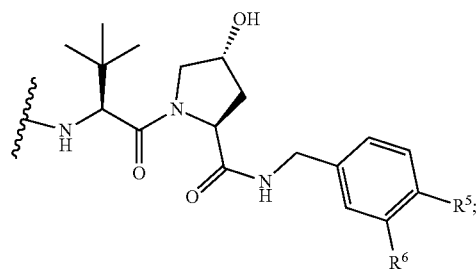

wherein $R^5$ is a heteroaryl ring, and $R^6$ is hydrogen or $C_{1-4}$ alkyl. In certain embodiments, R is a 5-membered heteroaryl ring comprising at least one nitrogen. In certain embodiments, $R^5$ is substituted or unsubstituted oxazolinyl, or substituted or unsubstituted thiazolinyl.

In certain embodiments, E is

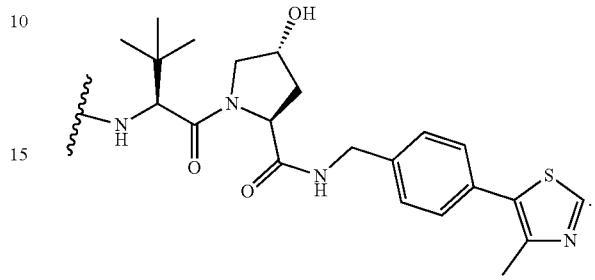

In certain embodiments, E is

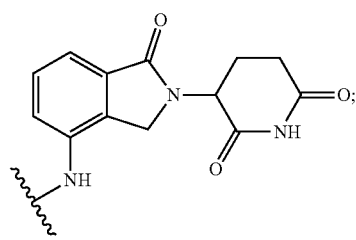

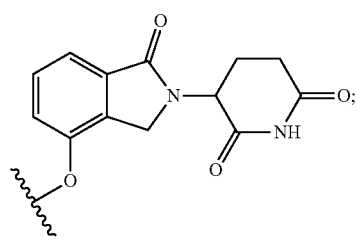

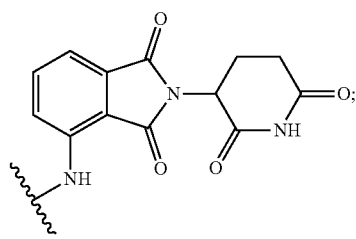

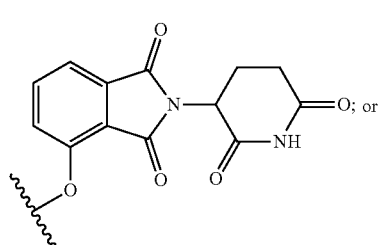

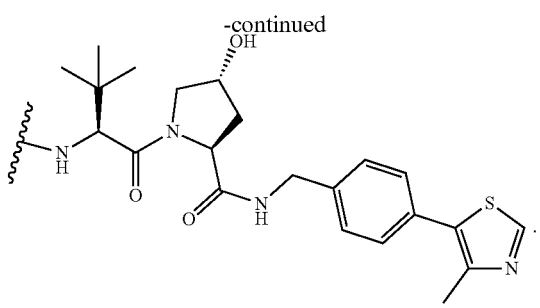

In certain embodiments, E is

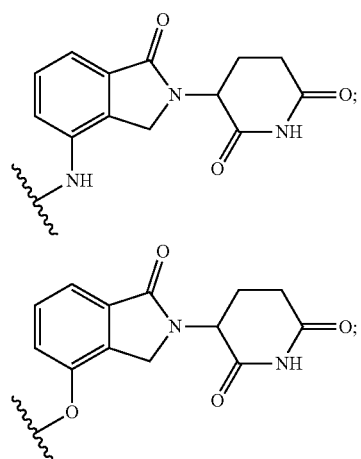

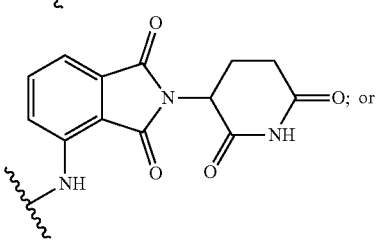

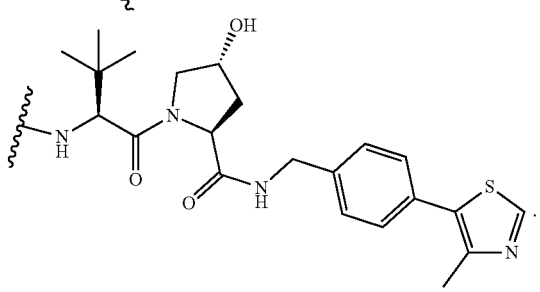

In certain embodiments, E is

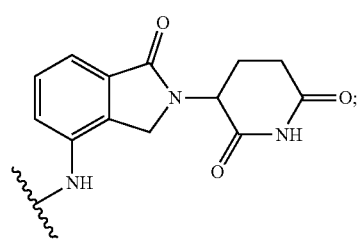

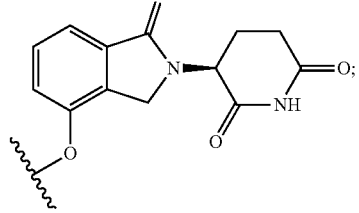

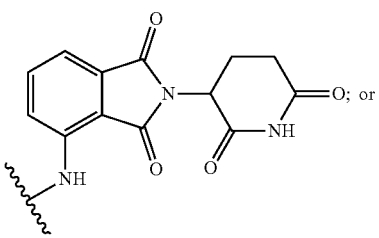

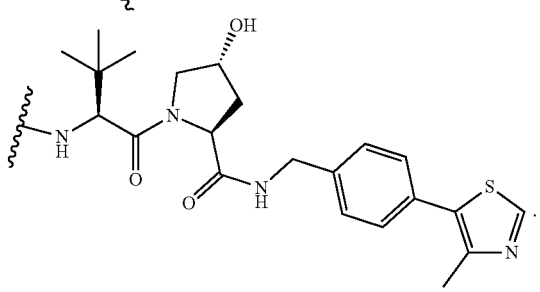

In certain embodiments, the compound of Formula I is a compound of Formula I-a:

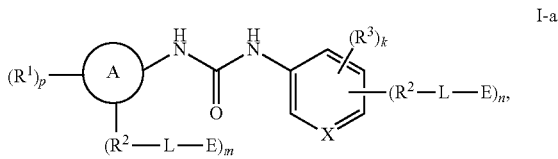

I-a or a pharmaceutically acceptable salt, co-crystal, tautomer, stereoisomer, solvate, hydrate, polymorph, isotopically enriched derivative, or prodrug thereof, wherein X is N, CH, or $CR^3$; and A, $R^1$, $R^2$, $R^3$, L, E, n, m, p, and k are as defined herein.

In certain embodiments, the compound of Formula I is a compound of Formula I-b:

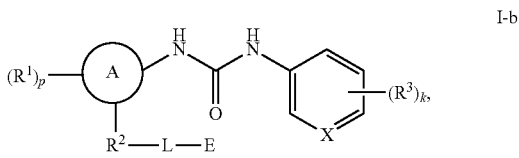

I-b or a pharmaceutically acceptable salt, co-crystal, tautomer, stereoisomer, solvate, hydrate, polymorph, isotopically enriched derivative, or prodrug thereof, wherein A, $R^1$, $R^2$, $R^3$, L, E, p, and k are as defined herein.

In certain embodiments, the compound of Formula I is a compound of Formula I-c:

I-c

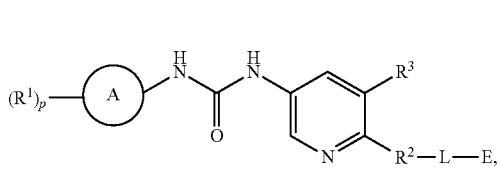

or a pharmaceutically acceptable salt, co-crystal, tautomer, stereoisomer, solvate, hydrate, polymorph, isotopically enriched derivative, or prodrug thereof, wherein A, $R^1$, $R^2$, $R^3$, L, E, and p are as defined herein.

In certain embodiments, the compound of Formula I is a compound of Formula I-d:

I-d

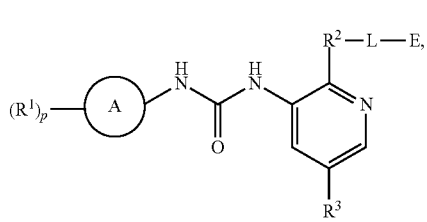

or a pharmaceutically acceptable salt, co-crystal, tautomer, stereoisomer, solvate, hydrate, polymorph, isotopically enriched derivative, or prodrug thereof, wherein A, $R^1$, $R^2$, $R^3$, L, E, and p are as defined herein.

In certain embodiments, the compound of Formula I is a compound of Formula I-e,

I-e

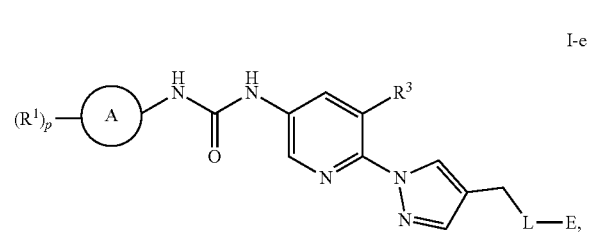

or a pharmaceutically acceptable salt, co-crystal, tautomer, stereoisomer, solvate, hydrate, polymorph, isotopically enriched derivative, or prodrug thereof, wherein A, $R^1$, $R^3$, L, E, and p are as defined herein.

In certain embodiments, the compound of Formula I is a compound of Formula I-f:

I-f

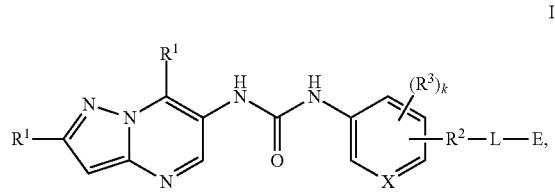

or a pharmaceutically acceptable salt, co-crystal, tautomer, stereoisomer, solvate, hydrate, polymorph, isotopically enriched derivative, or prodrug thereof, wherein X is N, CH, or $CR^3$; and $R^1$, $R^2$, $R^3$, L, E, and k are as defined herein.

In certain embodiments, the compound of Formula I is a compound of Formula I-g:

I-g

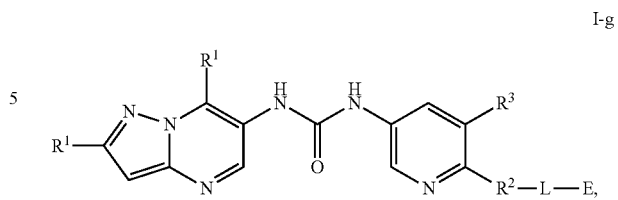

or a pharmaceutically acceptable salt, co-crystal, tautomer, stereoisomer, solvate, hydrate, polymorph, isotopically enriched derivative, or prodrug thereof, wherein $R^1$, $R^2$, $R^3$, L, and E are as defined herein.

In certain embodiments, the compound of Formula I is a compound of Formula I-h:

I-h

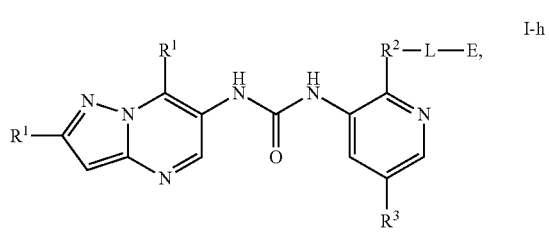

or a pharmaceutically acceptable salt, co-crystal, tautomer, stereoisomer, solvate, hydrate, polymorph, isotopically enriched derivative, or prodrug thereof, wherein A, $R^1$, $R^2$, $R^3$, L, and E are as defined herein.

In certain embodiments, the compound of Formula I is a compound of Formula I-i:

I-i

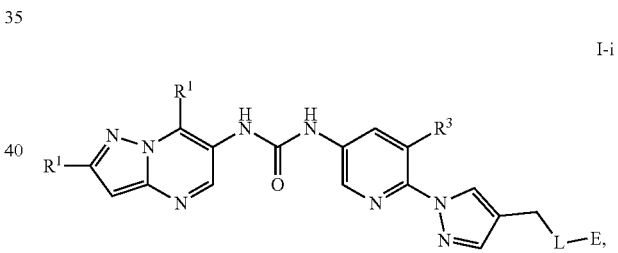

or a pharmaceutically acceptable salt, co-crystal, tautomer, stereoisomer, solvate, hydrate, polymorph, isotopically enriched derivative, or prodrug thereof, wherein $R^1$, $R^3$, L, and E are as defined herein.

In certain embodiments, the compound of Formula I is a compound of Formula I-j:

I-j

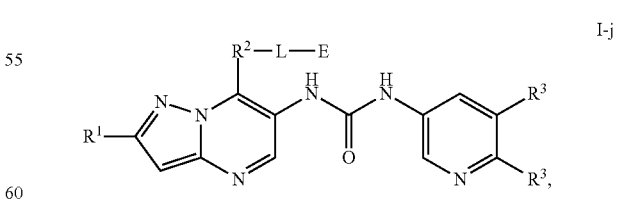

or a pharmaceutically acceptable salt, co-crystal, tautomer, stereoisomer, solvate, hydrate, polymorph, isotopically enriched derivative, or prodrug thereof, wherein $R^1$, $R^2$, $R^3$, L, and E are as defined herein.

In certain embodiments, the compound of Formula I is a compound of Formula I-k:

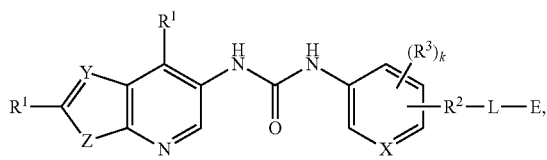

I-k or a pharmaceutically acceptable salt, co-crystal, tautomer, stereoisomer, solvate, hydrate, polymorph, isotopically enriched derivative, or prodrug thereof, wherein X is N, CH, or $CR^3$; Y is CH or N; Z is NH, S, or O; and $R^1$, $R^2$, $R^3$, L, E, and k are as defined herein.

In certain embodiments, the compound of Formula I is a compound of Formula I-l:

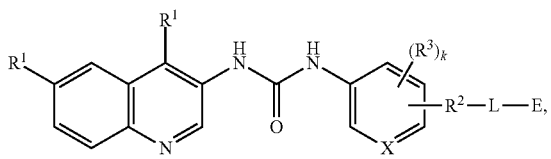

I-l or a pharmaceutically acceptable salt, co-crystal, tautomer, stereoisomer, solvate, hydrate, polymorph, isotopically enriched derivative, or prodrug thereof, wherein X is N, CH, or $CR^3$; and $R^1$, $R^2$, $R^3$, L, E, and k are as defined herein.

In certain embodiments, the compound of Formula I is a compound of Formula I-m,

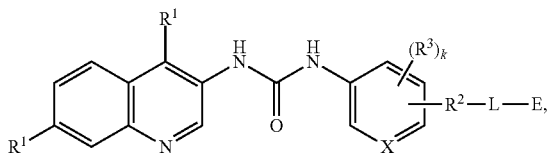

I-m or a pharmaceutically acceptable salt, co-crystal, tautomer, stereoisomer, solvate, hydrate, polymorph, isotopically enriched derivative, or prodrug thereof, wherein X is N, CH, or $CR^3$; and $R^1$, $R^2$, $R^3$, L, E, and k are as defined herein.

In certain embodiments, the compound of Formula I is a compound of Formula I-n:

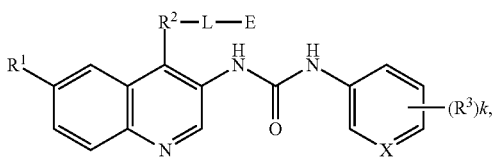

I-n or a pharmaceutically acceptable salt, co-crystal, tautomer, stereoisomer, solvate, hydrate, polymorph, isotopically enriched derivative, or prodrug thereof, wherein X is N, CH, or $CR^3$; and $R^1$, $R^2$, $R^3$, L, E, and k, are as defined herein.

In certain embodiments, the compound of Formula I is a compound of Formula I-o:

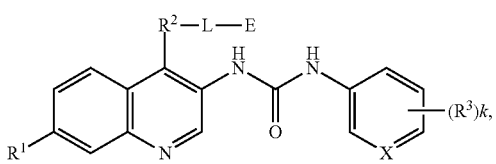

I-o or a pharmaceutically acceptable salt, co-crystal, tautomer, stereoisomer, solvate, hydrate, polymorph, isotopically enriched derivative, or prodrug thereof, wherein X is N, CH, or $CR^3$; and $R^1$, $R^2$, $R^3$, L, E, and k, are as defined herein.

In certain embodiments, the compound of Formula I is a compound of Formula I-p:

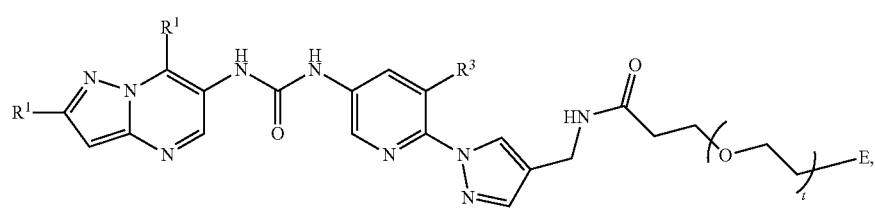

I-p or a pharmaceutically acceptable salt, co-crystal, tautomer, stereoisomer, solvate, hydrate, polymorph, isotopically enriched derivative, or prodrug thereof, wherein t is 2 or 4; and $R^1$, $R^3$, and E are as defined herein.

In certain embodiments, the compound of Formula I is a compound of Formula I-q:

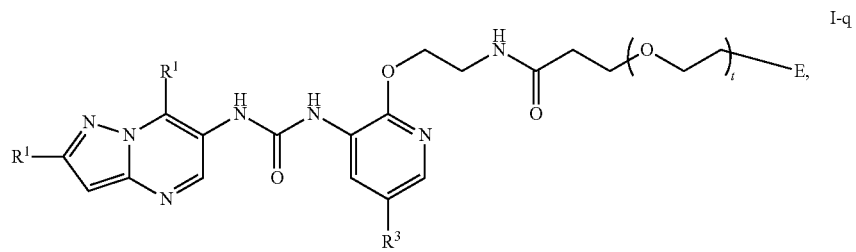

or a pharmaceutically acceptable salt, co-crystal, tautomer, stereoisomer, solvate, hydrate, polymorph, isotopically enriched derivative, or prodrug thereof, wherein t is 0, 1, 2, 3, 4, 5, or 6; and $R^1$, $R^3$, and E are as defined herein.

In certain embodiments of the compound of Formula I-q, t is 2 or 4; and $R^1$, $R^3$, and E are as defined herein.

In certain embodiments, the compound of Formula I is a compound of Formula I-r:

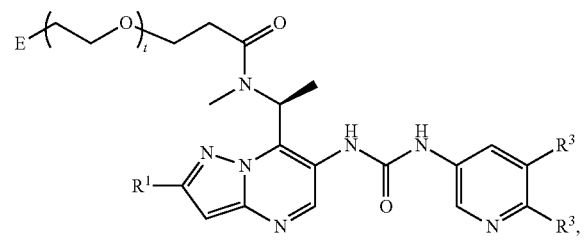

or a pharmaceutically acceptable salt, co-crystal, tautomer, stereoisomer, solvate, hydrate, polymorph, isotopically enriched derivative, or prodrug thereof, wherein t is 2 or 4; and $R^1$, $R^3$, and E are as defined herein.

In certain embodiments, the compound of Formula I is a compound of Formula I-s:

or a pharmaceutically acceptable salt, co-crystal, tautomer, stereoisomer, solvate, hydrate, polymorph, isotopically enriched derivative, or prodrug thereof, wherein t is 0, 1, 2, 3, 4, 5, or 6; and $R^1$, $R^3$, and E are as defined herein.

In certain embodiments of the compound of Formula I-s, t is 2, 3, or 4; and $R^1$, $R^3$, and E are as defined herein.

In certain embodiments, the compound of Formula I is a compound of Formula I-t:

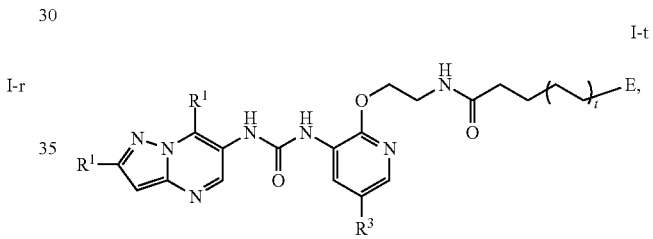

or a pharmaceutically acceptable salt, co-crystal, tautomer, stereoisomer, solvate, hydrate, polymorph, isotopically enriched derivative, or prodrug thereof, wherein t is 0, 1, 2, 3, 4, 5, or 6; and $R^1$, $R^3$, and E are as defined herein.

In certain embodiments of the compound of Formula I-t, t is 2, 3, or 4; and $R^1$, $R^3$, and E are as defined herein.

In certain embodiments, the compound of Formula I is a compound of Formula I-u:

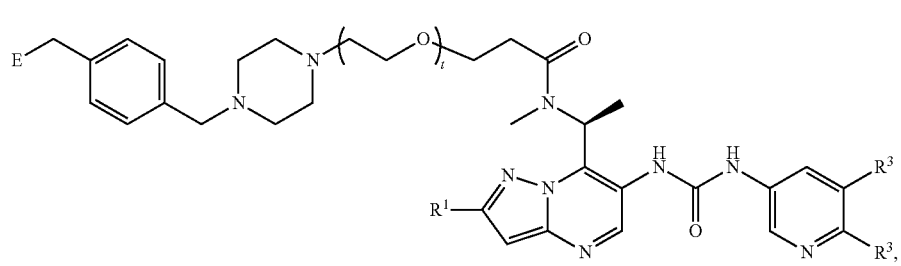

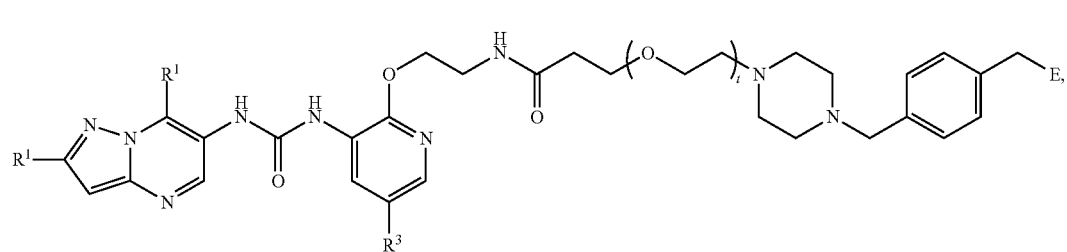

I-u or a pharmaceutically acceptable salt, co-crystal, tautomer, stereoisomer, solvate, hydrate, polymorph, isotopically enriched derivative, or prodrug thereof, wherein t is 0, 1, 2, 3, 4, 5, or 6; and $R^1$, $R^3$, and E are as defined herein.

In certain embodiments of the compound of Formula I-u, t is 2, 3, or 4; and $R^1$, $R^3$, and E are as defined herein.

In certain embodiments, the compound of Formula I is a compound of Formula I-v:

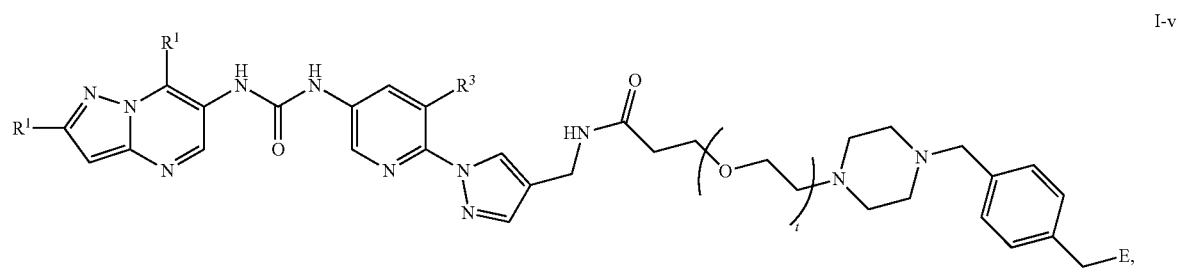

I-v or a pharmaceutically acceptable salt, co-crystal, tautomer, stereoisomer, solvate, hydrate, polymorph, isotopically enriched derivative, or prodrug thereof, wherein t is 0, 1, 2, 3, 4, 5, or 6; and $R^1$, $R^3$, and E are as defined herein.

In certain embodiments of the compound of Formula I-v, t is 2, 3, or 4; and $R^1$, $R^3$, and E are as defined herein.

In certain embodiments, the compound of Formula I is a compound of Table 1, or a pharmaceutically acceptable salt, co-crystal, tautomer, stereoisomer, solvate, hydrate, polymorph, isotopically enriched derivative, or prodrug thereof.

TABLE 1

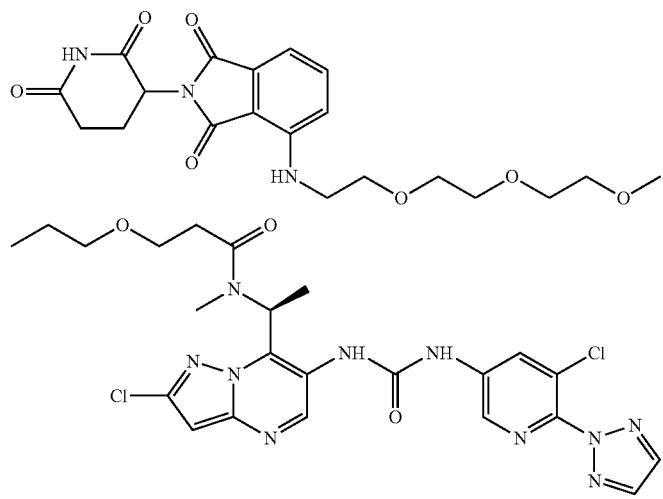

TABLE 1-continued
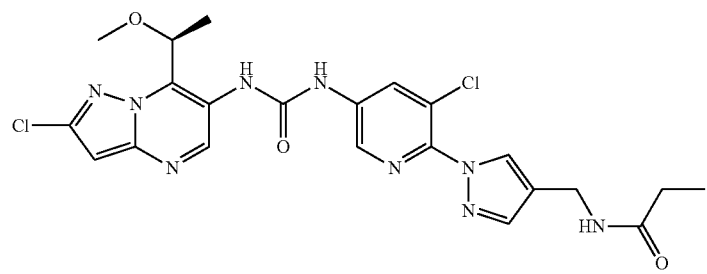
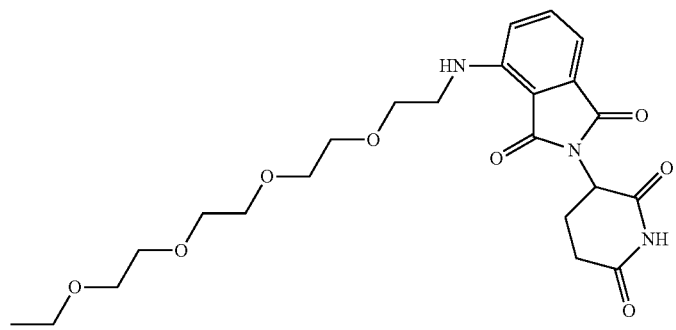
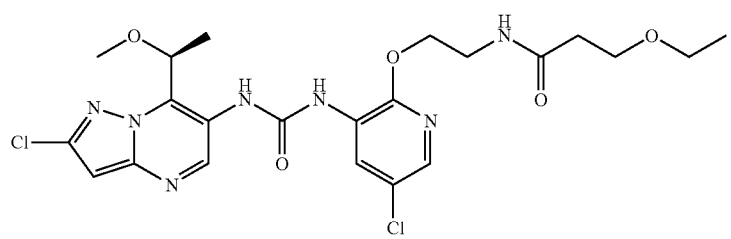
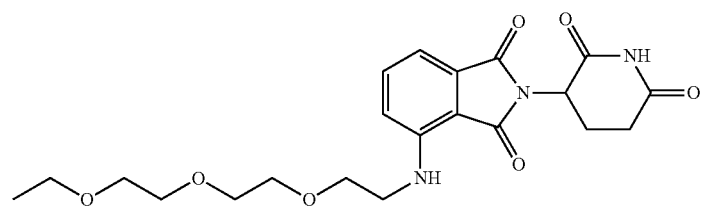
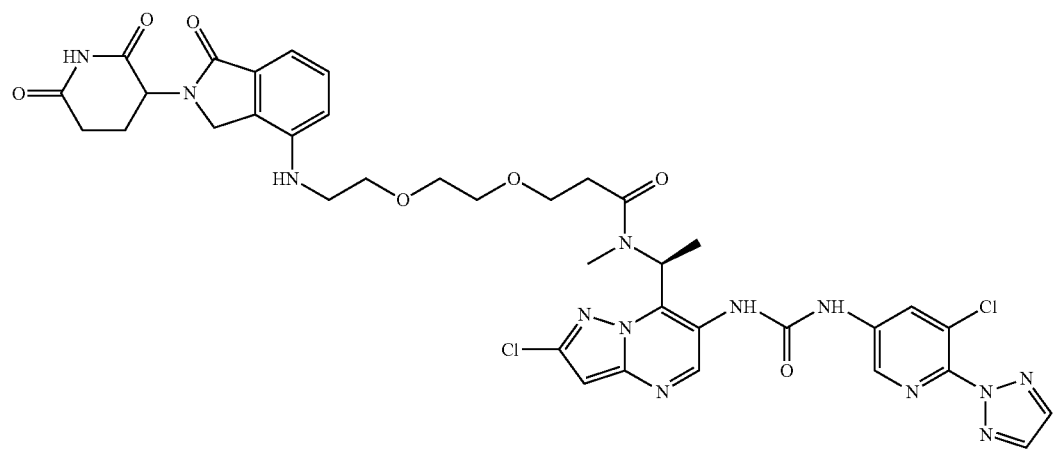 [SMILES: C[C@@H](c1c(NC(=O)Nc2cnc(-n3nccn3)c(Cl)c2)cnc2cc(Cl)nn12)N(C)C(=O)CCOCCOCCNc1cccc2c1CN(C1CCC(=O)NC1=O)C2=O]

TABLE 1-continued
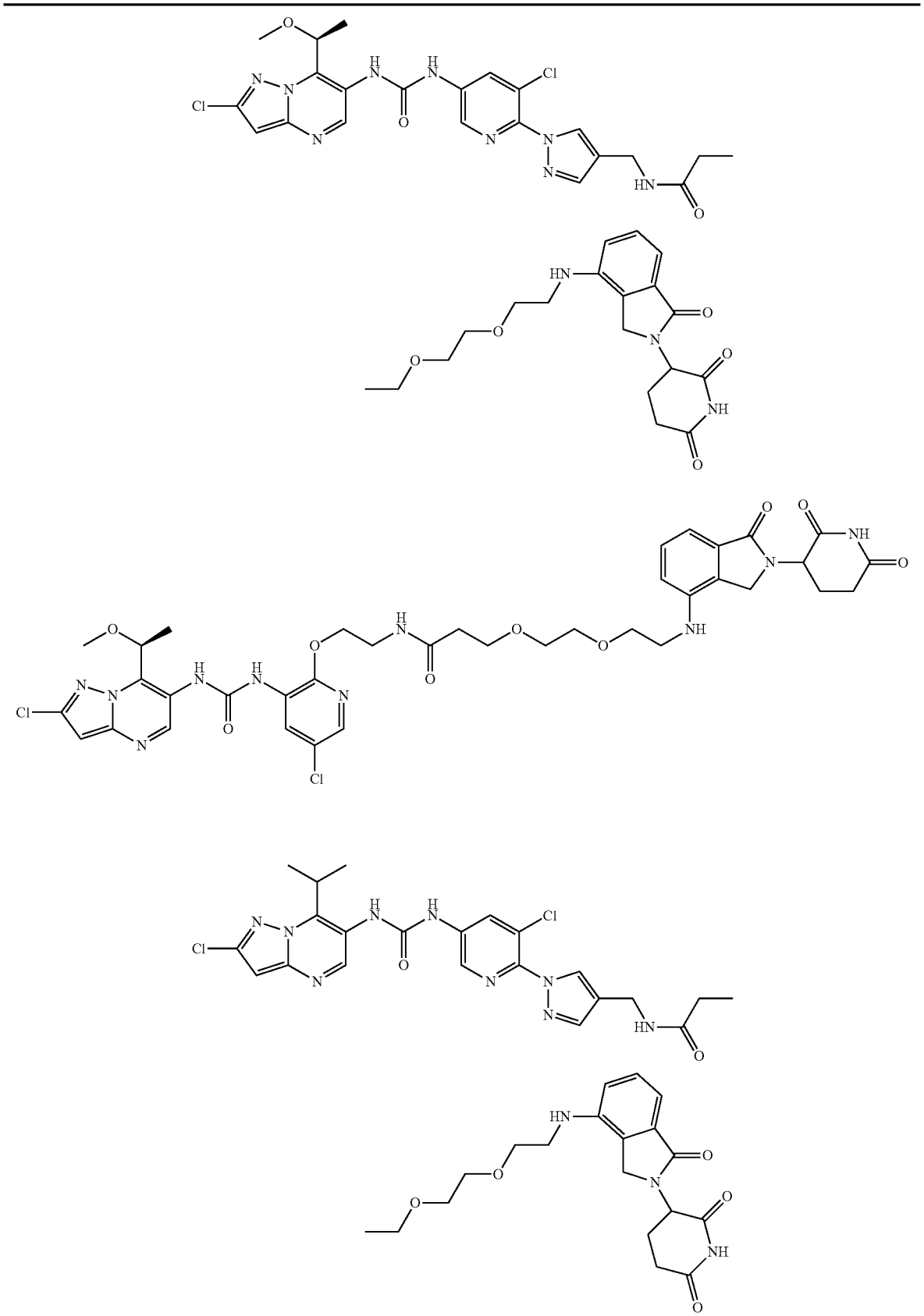

TABLE 1-continued
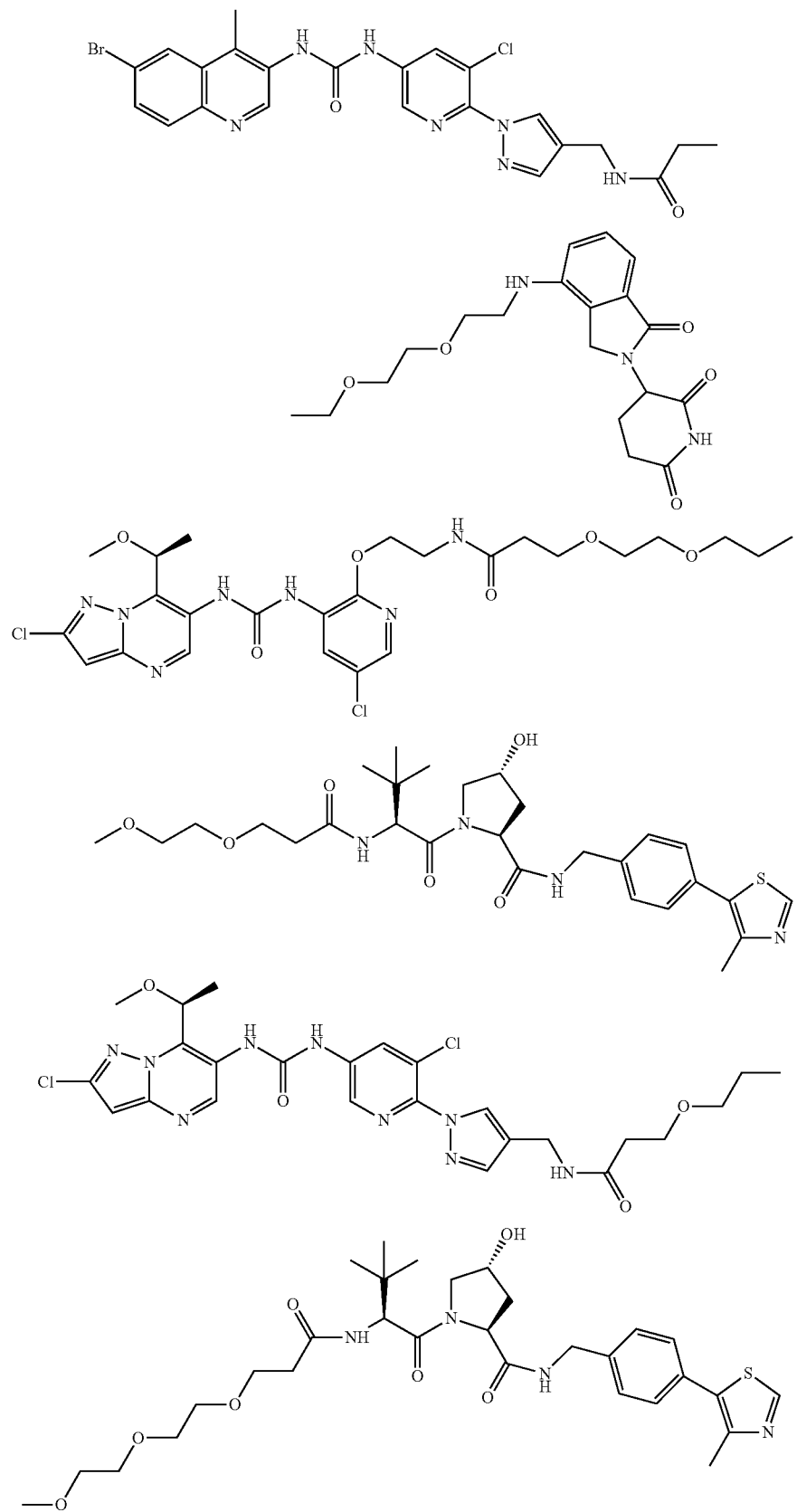

US 10,689,366 B2
89
In certain embodiments, the compound of Formula I is a compound of Table 2, or a pharmaceutically acceptable salt, co-crystal, tautomer, stereoisomer, solvate, hydrate, polymorph, isotopically enriched derivative, or prodrug thereof.
TABLE 2
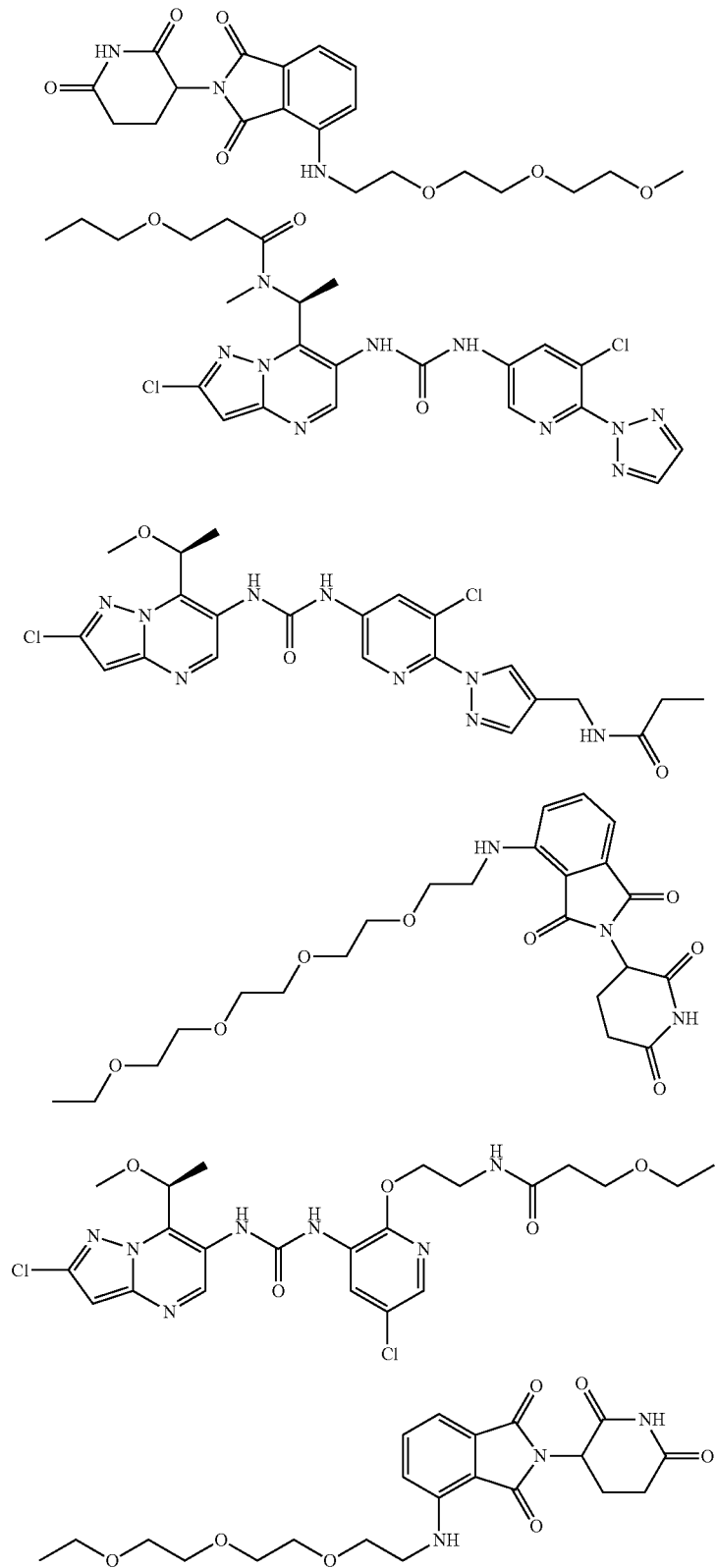

TABLE 2-continued
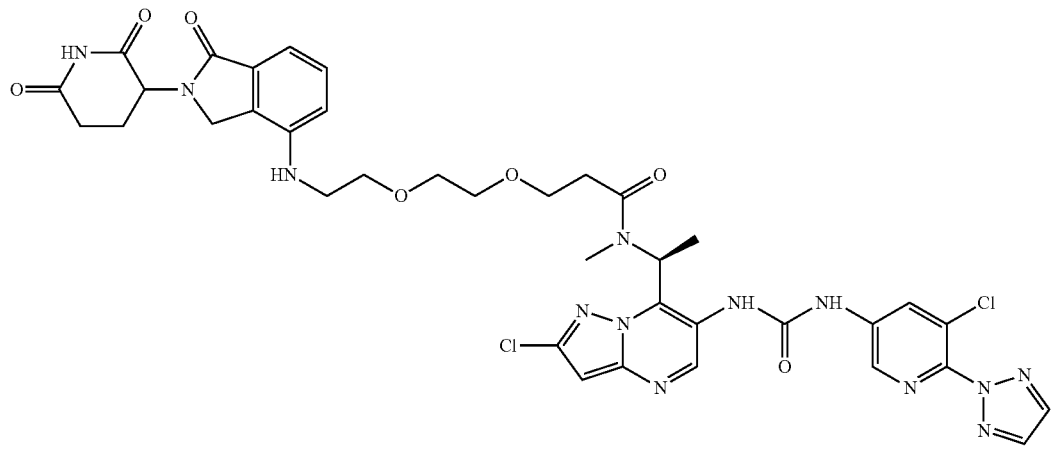 [SMILES: C[C@@H](c1c(NC(=O)Nc2cnc(-n3nccn3)c(Cl)c2)cnc2cc(Cl)nn12)N(C)C(=O)CCOCCOCCNc1cccc2c1CN(C1CCC(=O)NC1=O)C2=O]
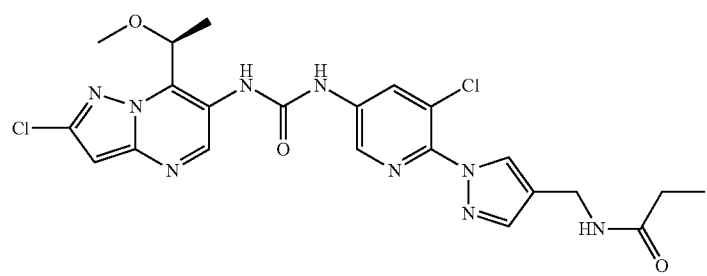
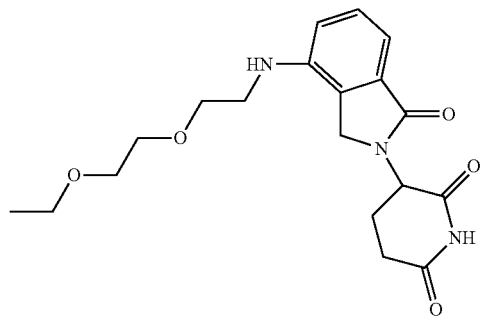
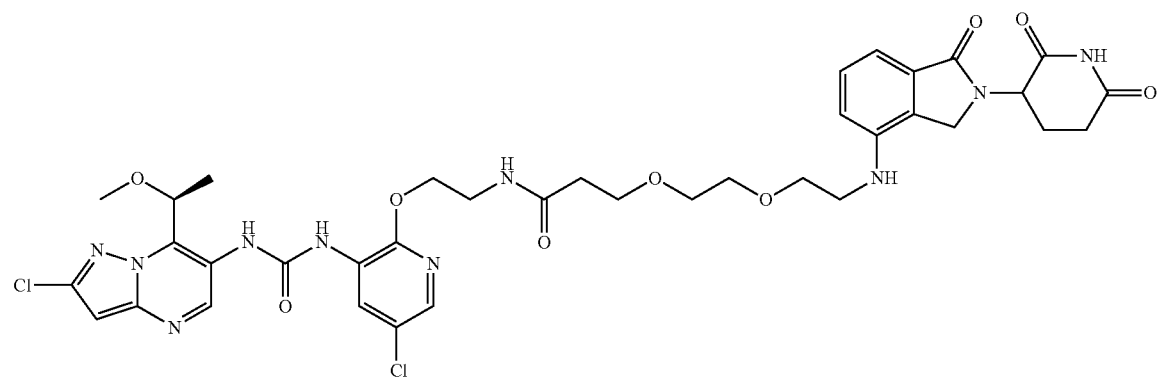 [SMILES: CO[C@@H](C)c1c(NC(=O)Nc2cc(Cl)cnc2OCCNC(=O)CCOCCOCCNc2cccc3c2CN(C2CCC(=O)NC2=O)C3=O)cnc2cc(Cl)nn12]

TABLE 2-continued
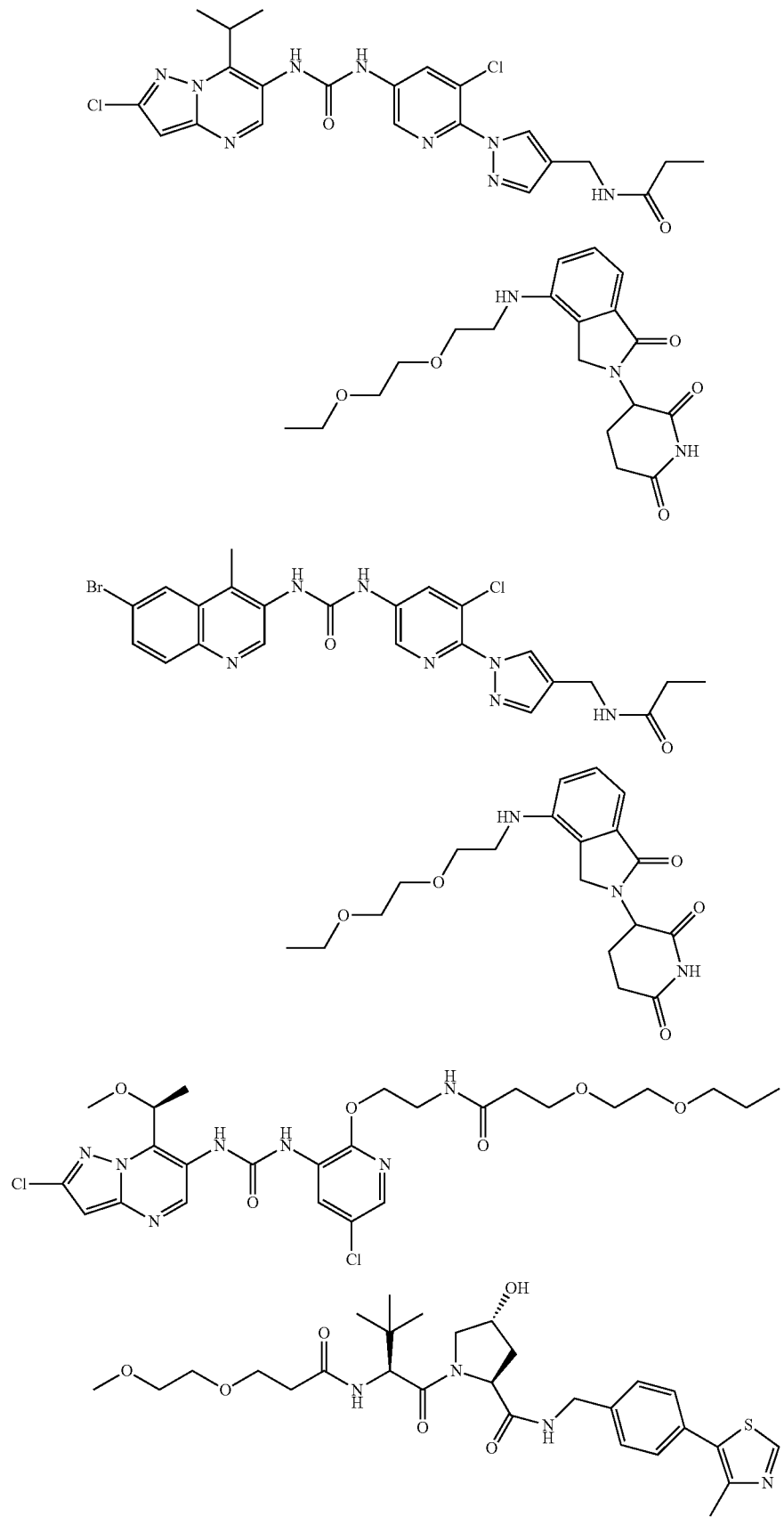

TABLE 2-continued
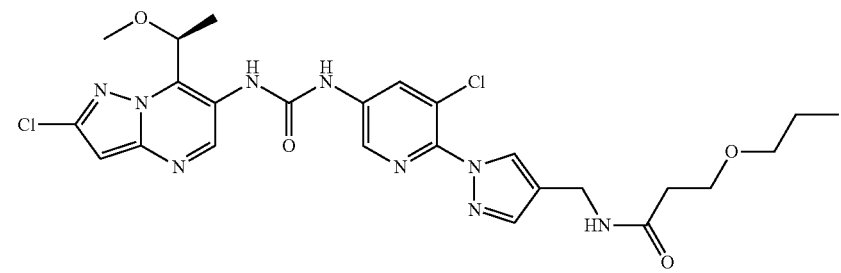
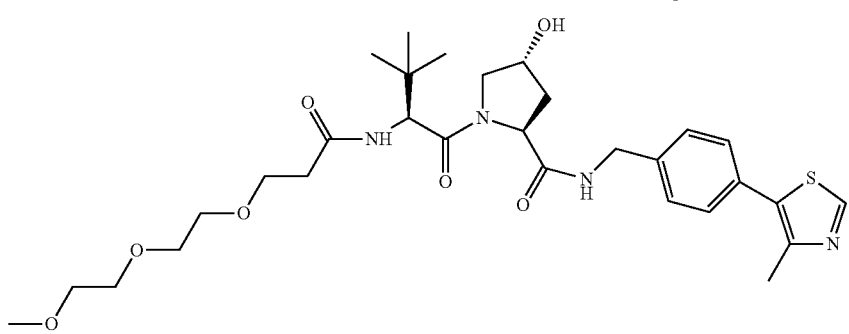
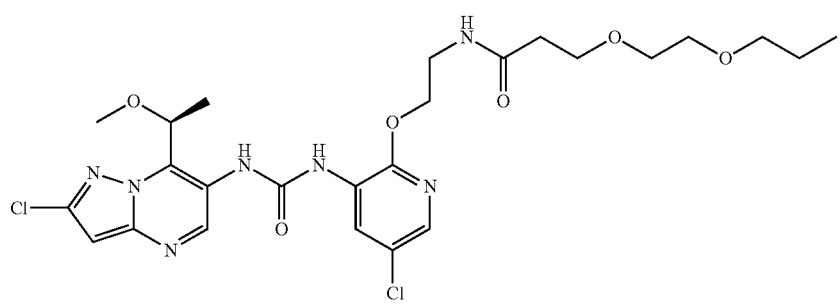
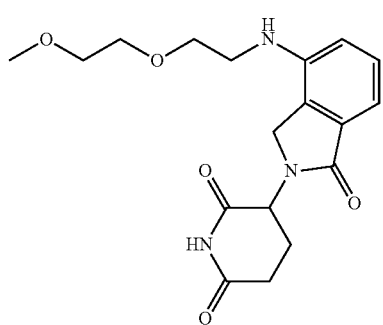
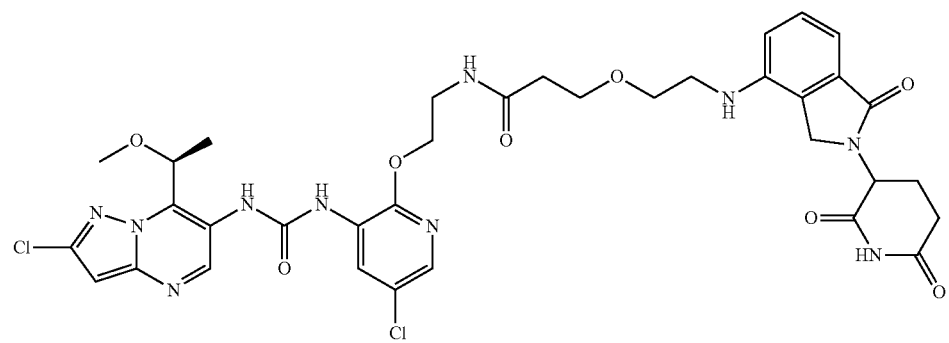 [SMILES: CO[C@@H](C)c1c(NC(=O)Nc2cc(Cl)cnc2OCCNC(=O)CCOCCNc2cccc3c2CN(C2CCC(=O)NC2=O)C3=O)cnc2cc(Cl)nn12]

TABLE 2-continued
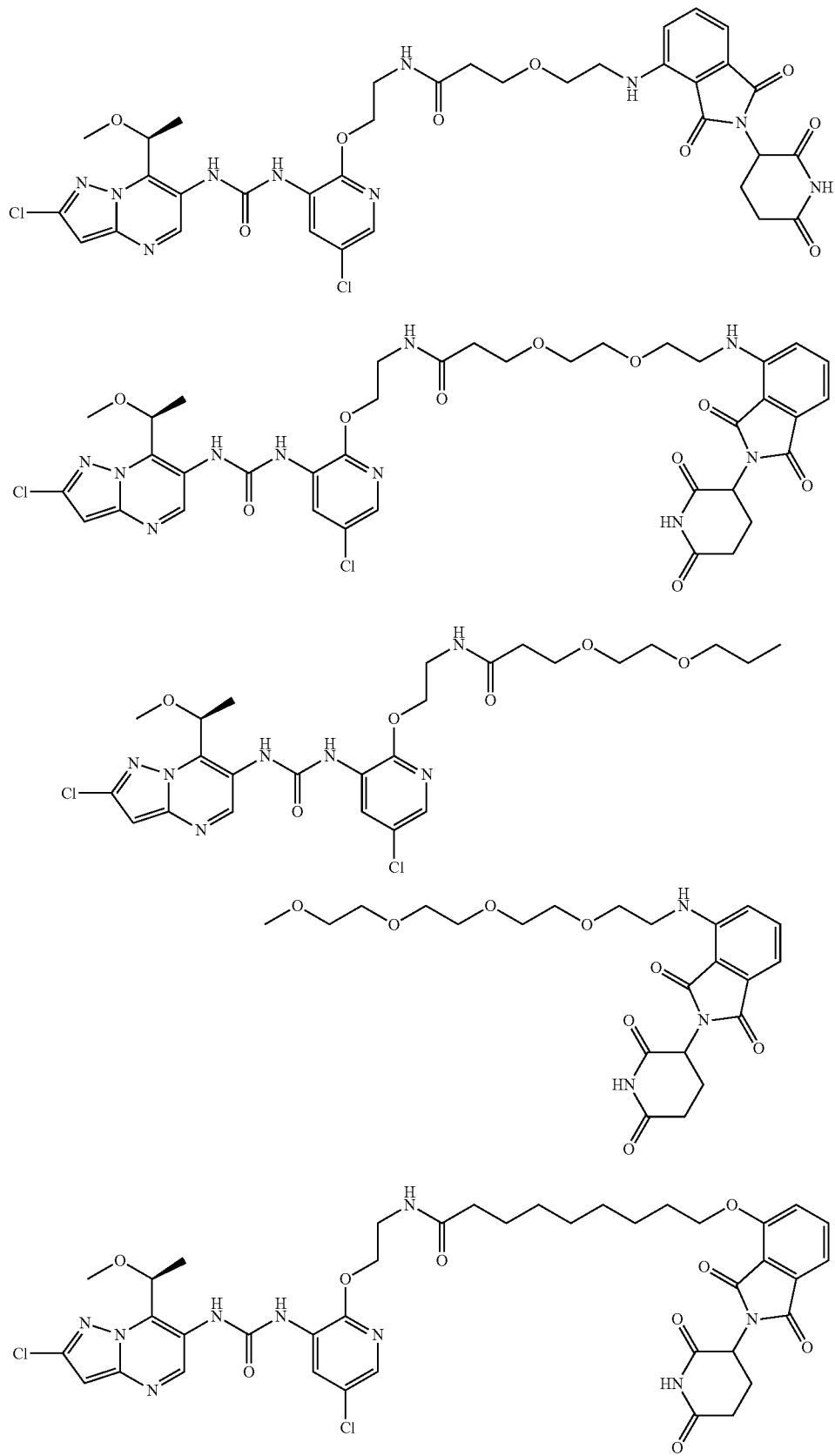

TABLE 2-continued
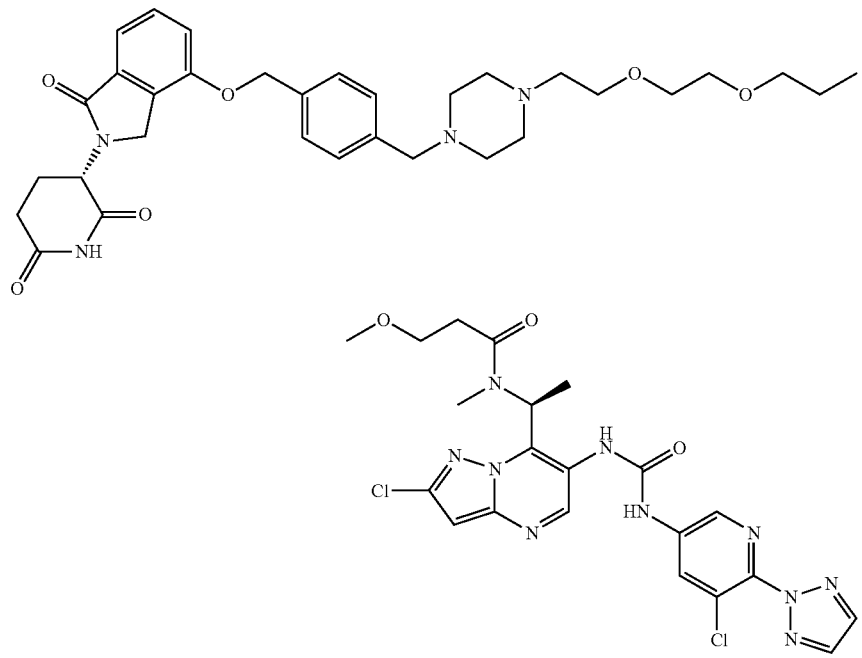
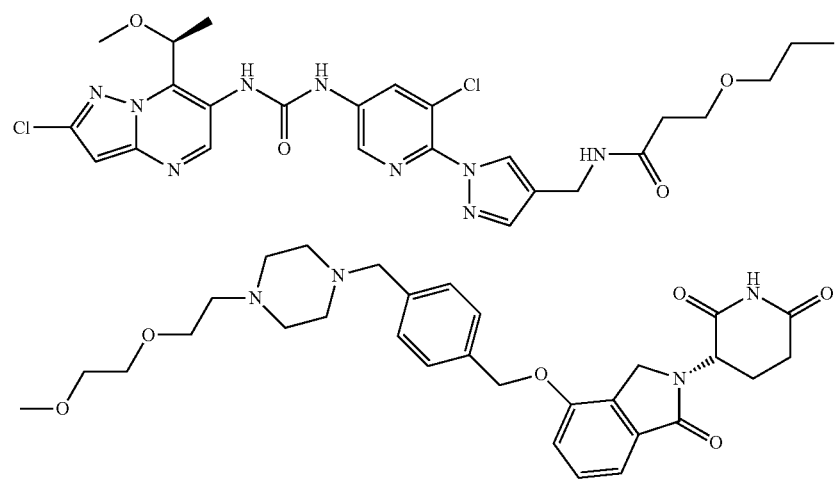

TABLE 2-continued

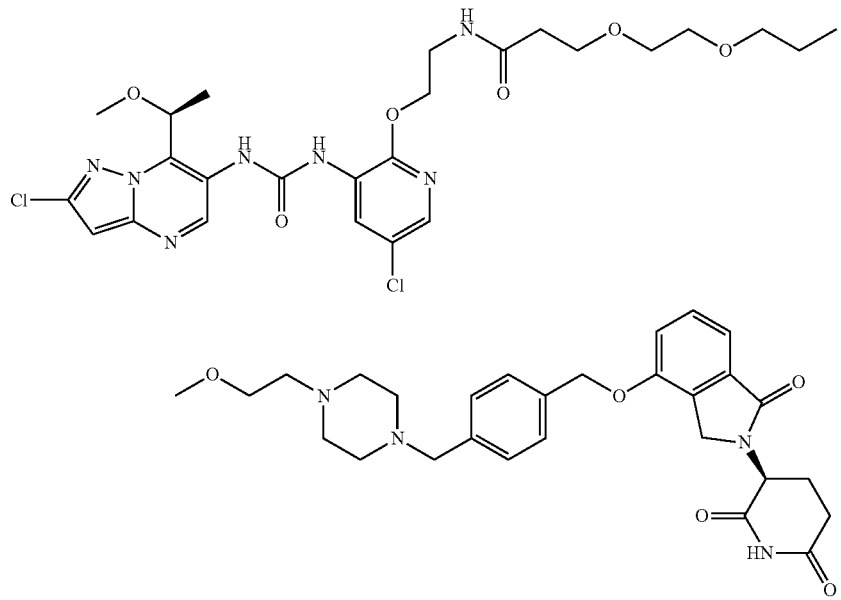

In certain embodiments, the compound of Formula I inhibits MALT1 with a $K_i$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I inhibits MALT1 with an $IC_{50}$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I selectively inhibits MALT1 over another protein. In some embodiments, the compound of Formula I selectively inhibits MALT1 as compared to another paracaspase. In some embodiments, the compound of Formula I selectively inhibits MALT1 over PCASP2 (paracaspace 2). In some embodiments, the compound of Formula I selectively inhibits MALT1 over PCASP3 (paracaspace 3). In some embodiments, the compound of Formula I selectively inhibits MALT1 over PCASP2 or PCASP3. In some embodiments, the compound of Formula I selectively inhibits MALT1 over PCASP2 and PCASP3. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formula I binds an E3 ubiquitin ligase with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I binds Cereblon with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I binds VHL with a $K_d$ of less than 100,000 nM, less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the compound of Formula I selectively binds an E3 ubiquitin ligase as compared to another protein. In some embodiments, the compound of Formula I selectively binds Cereblon over another protein. In some embodiments, the compound of Formula I selectively binds Cereblon over another E3 ubiquitin ligase. In some embodiments, the compound of Formula I selectively binds VHL over another protein. In some embodiments, the compound of Formula I selectively binds VHL over another E3 ubiquitin ligase. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formula I promotes the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of MALT1 at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

In certain embodiments, the compound of Formula I promotes the degradation of 10-30%, 31-50%, or 50-99% of MALT1 at a concentration of 1,000 nM. In certain embodiments, the compound of Formula I promotes the degradation of 10-30%, 31-50%, or 50-99% of MALT1 at a concentration of 100 nM.

In certain embodiments, the compound of Formula I promotes the degradation of at least 5%, at least 10%, at least 20%, at least 30%, at least 40%, at least 50%, at least 60%, at least 70%, at least 80%, at least 90%, at least 95%, or at least 99% of MALT1 at a concentration of 1,000 nM. In certain embodiments, the compound of Formula I promotes the degradation of at least 5%, at least 10%, at least 20%, at least 30%, at least 40%, at least 50%, at least 60%, at least 70%, at least 80%, at least 90%, at least 95%, or at least 99% of MALT1 at a concentration of 100 nM.

Pharmaceutical Compositions, Kits, and Administration

The present disclosure provides pharmaceutical compositions comprising a compound of Formula I, or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula I, or a pharmaceutically acceptable salt thereof, and a pharmaceutically acceptable excipient.

In certain embodiments, the compound of Formula I is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a proliferative disease in a subject in need thereof. In certain embodiments, the effective amount is an amount effective for preventing a proliferative disease in a subject in need thereof. In certain embodiments, the effective amount is an amount effective for treating a hematological cancer in a subject in need thereof. In certain embodiments, the effective amount is an amount effective for preventing a hematological cancer in a subject in need thereof. In certain embodiments, the effective amount is an amount effective for treating an autoimmune disorder in a subject in need thereof. In certain embodiments, the effective amount is an amount effective for preventing an autoimmune disorder in a subject in need thereof. In certain embodiments, the effective amount is an amount effective for treating an inflammatory disease in a subject in need thereof. In certain embodiments, the effective amount is an amount effective for preventing an inflammatory disease in a subject in need thereof. In certain embodiments, the effective amount is an amount effective for reducing the risk of developing a disease (e.g., proliferative disease, hematological cancer, inflammatory disease, or autoimmune disorder) in a subject in need thereof. In certain embodiments, the effective amount is an amount effective for inhibiting the activity (e.g., aberrant activity, such as increased activity) of a protein in a subject or cell.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting the activity of MALT1 by at least about 10%, at least about 20%, at least about 30%, at least about 40%, at least about 50%, at least about 60%, at least about 70%, at least about 80%, at least about 90%, at least about 95%, at least about 98%, or at least about 99%. In certain embodiments, the effective amount is an amount effective for promoting the degradation of at least about 10%, at least about 20%, at least about 30%, at least about 40%, at least about 50%, at least about 60%, at least about 70%, at least about 80%, at least about 90%, at least about 95%, at least about 98%, or at least about 99% of MALT1. In certain embodiments, the effective amount is an amount effective for inhibiting the activity of MALT1 and/or promoting the degradation of MALT1 by a range between a percentage described in this paragraph and another percentage described in this paragraph, inclusive.

The present disclosure provides pharmaceutical compositions comprising a compound that interacts with MALT1 and/or an E3 ubiquitin ligase (e.g., Cereblon, VHL) for use in treating cancer in a subject in need thereof. In certain embodiments, the composition is for use in treating a hematological cancer. In certain embodiments, the composition is for use in treating a lymphoid malignancy. In certain embodiments, the composition is for use in treating a leukemia, a lymphoma, or multiple myeloma. In certain embodiments, the composition is for use in treating a non-Hodgkin's lymphoma. In certain embodiments, the composition is for use in treating DLBCL. In certain embodiments, the composition is for use in treating ABC-DLBCL.

The present disclosure provides pharmaceutical compositions for the treatment of cancer comprising a compound that interacts with MALT1 and/or an E3 ubiquitin ligase (e.g., Cereblon, VHL). In certain embodiments, the pharmaceutical composition is for treatment of a hematological cancer. In certain embodiments, the pharmaceutical composition is for treatment of a lymphoid malignancy. In certain embodiments, the pharmaceutical composition is for treatment of a leukemia, a lymphoma, or multiple myeloma. In certain embodiments, the pharmaceutical composition is for treatment of non-Hodgkin's lymphoma. In certain embodiments, the pharmaceutical composition is for treatment of DLBCL. In certain embodiments, the pharmaceutical composition is for treatment of ABC-DLBCL.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, and/or in reducing the risk to develop a disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological cancer, autoimmune disease, and/or inflammatory disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, and anti-viral agents. In certain embodiments, the additional pharmaceutical agent is an anti-viral agent. In certain embodiments, the additional pharmaceutical agent is an immunotherapy. In certain embodiments, the additional pharmaceutical agent is an anti-proliferative agent. In certain embodiments, the additional pharmaceutical agent is an anti-cancer agent. In certain embodiments, the anti-cancer agents include, but are not limited to, epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), cell signaling pathway inhibitors (e.g., tyrosine protein kinase inhibitors), modulators of protein stability (e.g., proteasome inhibitors), Hsp90 inhibitors, glucocorticoids, all-trans retinoic acids, anti-estrogens (e.g., tamoxifen, raloxifene, and megestrol), LHRH agonists (e.g., goscrclin and leuprolide), anti-androgens (e.g. flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonuclotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), thalidomide, lenalidomide, pomalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the additional pharmaceutical agent is an immunotherapy. In certain embodiments, the immunotherapy is useful in the treatment of a cancer. Exemplary immunotherapies include, but are not limited to, T-cell therapies, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies. In certain embodiments, the immunotherapy is a T-cell therapy. In certain embodiments, the T-cell therapy is chimeric antigen receptor T cells (CAR-T). In certain embodiments, the immunotherapy is an antibody. In certain embodiments, the antibody is an anti-PD-1 antibody, an anti-PD-L1 antibody, an anti-CTLA-4 antibody, an anti-TIM3 antibody, an anti-OX40 antibody, an anti-GITR antibody, an anti-LAG-3 antibody, an anti-CD137 antibody, an anti-CD27 antibody, an anti-CD28 antibody, an anti-CD28H antibody, an anti-CD30 antibody, an anti-CD39 antibody, an anti-CD40 antibody, an anti-CD47 antibody, an anti-CD48 antibody, an anti-CD70 antibody, an anti-CD73 antibody, an anti-CD96 antibody, an anti-CD160 antibody, an anti-CD200 antibody, an anti-CD244 antibody, an anti-ICOS antibody, an anti-TNFRSF25 antibody, an anti-TMIGD2 antibody, an anti-DNAM1 antibody, an anti-BTLA antibody, an anti-LIGHT antibody, an anti-TIGIT antibody, an anti-VISTA antibody, an anti-HVEM antibody, an anti-Siglec antibody, an anti-GAL1 antibody, an anti-GAL3 antibody, an anti-GAL9 antibody, an anti-BTNL2 (butrophylins) antibody, an anti-B7-H3 antibody, an anti-B7-H4 antibody, an anti-B7-H5 antibody, an anti-B7-H6 antibody, an anti-KIR antibody, an anti-LIR antibody, an anti-ILT antibody, an anti-MICA antibody, an anti-MICB antibody, an anti-NKG2D antibody, an anti-NKG2A antibody, an anti-TGFβ antibody, an anti-TGFβR antibody, an anti-CXCR4 antibody, an anti-CXCL12 antibody, an anti-CCL2 antibody, an anti-IL-10 antibody, an anti-IL-13 antibody, an anti-IL-23 antibody, an anti-phosphatidylserine antibody, an anti-neuropilin antibody, an anti-GalCer antibody, an anti-HER2 antibody, an anti-VEGFA antibody, an anti-VEGFR antibody, an anti-EGFR antibody, or an anti-Tie2 antibody. In certain embodiments, the antibody is pembrolizumab, nivolumab, pidilizumab, ipilimumab, tremelimumab, durvalumab, atezolizumab, avelumab, PF-06801591, utomilumab, PDR001, PBF-509, MGB453, LAG525, AMP-224, INCSHR1210, INCAGN1876, INCAGN1949, samalizumab, PF-05082566, urelumab, lirilumab, lulizumab, BMS-936559, BMS-936561, BMS-986004, BMS-986012, BMS-986016, BMS-986178, IMP321, IPH2101, IPH2201, varilumab, ulocuplumab, monalizumab, MEDI0562, MEDI0680, MEDI1873, MEDI6383, MEDI6469, MEDI9447, AMG228, AMG820, CC-90002, CDX-1127, CGEN15001T, CGEN15022, CGEN15029, CGEN15049, CGEN15027, CGEN15052, CGEN15092, CX-072, CX-2009, CP-870893, lucatumumab, dacetuzumab, Chi Lob 7/4, RG6058, RG7686, RG7876, RG7888, TRX518, MK-4166, MGA271, IMC-CS4, emactuzumab, trastuzumab, pertuzumab, obinutuzumab, cabiralizumab, margetuximab, enoblituzumab, mogamulizumab, panitumumab, carlumab, bevacizumab, rituximab, or cetuximab.

In certain embodiments, the compounds described herein or pharmaceutical compositions can be administered in combination with an anti-cancer therapy including, but not limited to, surgery, radiation therapy, and transplantation (e.g., stem cell transplantation, bone marrow transplantation).

In certain embodiments, the compound or pharmaceutical composition is a solid. In certain embodiments, the compound or pharmaceutical composition is a powder. In certain embodiments, the compound or pharmaceutical composition can be dissolved in a liquid to make a solution. In certain embodiments, the compound or pharmaceutical composition is dissolved in water to make an aqueous solution. In certain embodiments, the pharmaceutical composition is a liquid for parental injection. In certain embodiments, the pharmaceutical composition is a liquid for oral administration (e.g., ingestion). In certain embodiments, the pharmaceutical composition is a liquid (e.g., aqueous solution) for intravenous injection. In certain embodiments, the pharmaceutical composition is a liquid (e.g., aqueous solution) for subcutaneous injection.

After formulation with an appropriate pharmaceutically acceptable excipient in a desired dosage, the pharmaceutical compositions of this invention can be administered to humans and other animals orally, parenterally, intracisternally, intraperitoneally, topically, bucally, or the like, depending on the disease or condition being treated.

In certain embodiments, a pharmaceutical composition comprising a compound of Formula I is administered, orally or parenterally, at dosage levels of each pharmaceutical composition sufficient to deliver from about 0.001 mg/kg to about 200 mg/kg in one or more dose administrations for one or several days (depending on the mode of administration). In certain embodiments, the effective amount per dose varies from about 0.001 mg/kg to about 200 mg/kg, about 0.001 mg/kg to about 100 mg/kg, about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, of subject body weight per day, one or more times a day, to obtain the desired therapeutic and/or prophylactic effect. In certain embodiments, the compounds described herein may be at dosage levels sufficient to deliver from about 0.001 mg/kg to about 200 mg/kg, from about 0.001 mg/kg to about 100 mg/kg, from about 0.01 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations). In certain embodiments, the composition described herein is administered at a dose that is below the dose at which the agent causes non-specific effects.

In certain embodiments, the pharmaceutical composition is administered at a dose of about 0.001 mg to about 1000 mg per unit dose. In certain embodiments, the pharmaceutical composition is administered at a dose of about 0.01 mg to about 200 mg per unit dose. In certain embodiments, the pharmaceutical composition is administered at a dose of about 0.01 mg to about 100 mg per unit dose. In certain embodiments, pharmaceutical composition is administered at a dose of about 0.01 mg to about 50 mg per unit dose. In certain embodiments, the pharmaceutical composition is administered at a dose of about 0.01 mg to about 10 mg per unit dose. In certain embodiments, the pharmaceutical composition is administered at a dose of about 0.1 mg to about 10 mg per unit dose.

Pharmaceutical compositions described herein can be prepared by any method known in the art of pharmacology. In general, such preparatory methods include the steps of bringing the composition comprising a compound of Formula I into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazelnut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include, but are not limited to, pharmaceutically acceptable emulsions, microemulsions, solutions, suspensions, syrups, and elixirs. In addition to the active agents, the liquid dosage forms may contain inert diluents commonly used in the art such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can also include adjuvants such as wetting agents, emulsifying and suspending agents, sweetening, flavoring, and perfuming agents. In certain embodiments for parenteral administration, agents of the invention are mixed with solubilizing agents such CREMOPHOR EL® (polyethoxylated castor oil), alcohols, oils, modified oils, glycols, polysorbates, cyclodextrins, polymers, and combinations thereof.

Injectable preparations, for example, sterile injectable aqueous or oleaginous suspensions, may be formulated according to the known art using suitable dispersing or wetting agents and suspending agents. Sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active agents can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets, and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include liquid or semi-liquid preparations such as liniments, lotions, gels, applicants, oil-in-water or water-in-oil emulsions such as creams, ointments, or pastes; or solutions or suspensions such as drops. Formulations for topical administration to the skin surface can be prepared by dispersing the drug with a dermatologically acceptable carrier such as a lotion, cream, ointment, or soap. Useful carriers are capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used. Ophthalmic formulation, ear drops, and eye drops are also contemplated as being within the scope of this invention. Additionally, the present disclosure contemplates the use of transdermal patches, which have the added advantage of providing controlled delivery of an agent to the body. Such dosage forms can be made by dissolving or dispensing the agent in the proper medium. Absorption enhancers can also be used to increase the flux of the agent across the skin. The rate can be controlled by either providing a rate controlling membrane or by dispersing the agent in a polymer matrix or gel.

Additionally, the carrier for a topical formulation can be in the form of a hydroalcoholic system (e.g., quids and gels), an anhydrous oil or silicone based system, or an emulsion system, including, but not limited to, oil-in-water, water-in-oil, water-in-oil-in-water, and oil-in-water-in-silicone emulsions. The emulsions can cover a broad range of consistencies including thin lotions (which can also be suitable for spray or aerosol delivery), creamy lotions, light creams, heavy creams, and the like. The emulsions can also include microemulsion systems. Other suitable topical carriers include anhydrous solids and semisolids (such as gels and sticks); and aqueous based mousse systems.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease, hematological cancer, autoimmune disease, inflammatory disease) in a subject in need thereof. In certain embodiments, the kits are useful for preventing a disease (e.g., proliferative disease, hematological cancer, autoimmune disease, inflammatory disease) in a subject in need thereof. In certain embodiments, the kits are useful for reducing the risk of developing a disease (e.g., proliferative disease, hematological cancer, autoimmune disease, inflammatory disease) in a subject in need thereof. In certain embodiments, the kits are useful for inhibiting the activity (e.g., aberrant activity, such as increased activity) of MALT1 in a subject or cell. In certain embodiments, the kits are useful for promoting the degradation of MALT1 in a subject or cell.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease, hematological cancer, autoimmune disease, inflammatory disease) in a subject in need thereof. In certain embodiments, the kits and instructions provide for preventing a disease (e.g., proliferative disease, hematological cancer, autoimmune disease, inflammatory disease) in a subject in need thereof. In certain embodiments, the kits and instructions provide for reducing the risk of developing a disease (e.g., proliferative disease, hematological cancer, autoimmune disease, inflammatory disease) in a subject in need thereof. In certain embodiments, the kits and instructions provide for inhibiting the activity (e.g., aberrant activity, such as increased activity) of MALT1 in a subject or cell. In certain embodiments, the kits and instructions provide for promoting the degradation of MALT1 in a subject or cell. A kit described herein may include one or more additional pharmaceutical agents described herein as a separate composition.

Methods of Treatment

In addition to acting as a scaffold protein within the CBM complex, MALT1 also has proteolytic activity that is constitutively activated in certain cancers, such as ABC-DLBCL. MALT1 inhibitors are known to inhibit ABC-DLBCL viability, making MALT1 inhibition and/or degradation an attractive method for the treatment of ABC-DLBCL.

Immunomodulatory agents, including thalidomide, lenalidomide, and pomalidomide bind Cereblon. Cereblon is a target for lenalidomide and pomalidomide in both multiple myeloma and ABC-DLBCL. Furthermore, in DLBCL cell lines, lenalidomide treatment preferentially suppresses proliferation of ABC-DLBCL cells in vitro and delays tumor growth in a human tumor xenograft model, with minimal effect on non-ABC-DLBCL cells.

In addition, compounds such as (2S,4R)-1-((S)-2-acetamido-3,3-dimethylbutanoyl)-4-hydroxy-N-(4-(4-methylthiazol-5-yl)benzyl)pyrrolidine-2-carboxamide, effectively bind VHL.

Accordingly, use of a bifunctional compound that binds and/or inhibits MALT1 and binds an E3 ubiquitin ligase (e.g., Cereblon, VHL) provides a method of treating diseases that rely on MALT1 activity.

The present disclosure provides methods for treating cancer. In certain embodiments, the application provides a method of treating a hematological cancer. In certain embodiments, the application provides a method of treating a lymphoid malignancy. In certain embodiments, the application provides a method of treating a leukemia, a lymphoma, or multiple myeloma. In certain embodiments, the application provides a method of treating non-Hodgkin's lymphoma. In certain embodiments, the application provides a method of treating DLBCL. In certain embodiments, the application provides a method of treating ABC-DLBCL. In certain embodiments, the application provides a method of promoting the degradation of MALT1. In certain embodiments, the application provides a method of promoting the degradation of MALT1 and binding an E3 ubiquitin ligase. In certain embodiments, the E3 ubiquitin ligase is Cereblon. In certain embodiments, the E3 ubiquitin ligase is VHL.

In certain embodiments, the methods comprise administering to a subject in need thereof (e.g., a subject with a cancer) a compound that interacts with MALT1, for example, a compound that is an inhibitor of MALT1, a modulator of MALT1, a binder of MALT1, a compound that modifies MALT1, or a compound that promotes the degradation of MALT1. The compound may also be an inhibitor of an E3 ubiquitin ligase, a modulator of an E3 ubiquitin ligase, a binder of an E3 ubiquitin ligase, a compound that modifies an E3 ubiquitin ligase, or a compound that disrupts the interaction of the E3 ubiquitin ligase with another protein. In certain embodiments, the methods comprise administering a compound of Formula I, or a pharmaceutically acceptable salt, co-crystal, tautomer, stereoisomer, solvate, hydrate, polymorph, isotopically enriched derivative, or prodrug, or composition thereof, to a subject in need thereof. In some embodiments, the method comprises administering a pharmaceutical composition comprising a compound of Formula I, or a pharmaceutically acceptable salt, co-crystal, tautomer, stereoisomer, solvate, hydrate, polymorph, isotopically enriched derivative, or prodrug, or composition thereof, to a subject in need thereof.

The present disclosure also provides a compound of Formula I, or a pharmaceutically acceptable salt, co-crystal, tautomer, stereoisomer, solvate, hydrate, polymorph, isotopically enriched derivative, or prodrug, or composition thereof, for use in the treatment of a cancer. In certain embodiments, the cancer is a hematological cancer. In certain embodiments, the cancer is a lymphoid malignancy. In certain embodiments, the cancer is a leukemia, a lymphoma, or multiple myeloma. In certain embodiments, the cancer is a non-Hodgkin's lymphoma. In certain embodiments, the cancer DLBCL. In certain embodiments, the cancer ABC-DLBCL.

The present disclosure also provides uses of a compound of Formula I, or a pharmaceutically acceptable salt, co-crystal, tautomer, stereoisomer, solvate, hydrate, polymorph, isotopically enriched derivative, or prodrug, or composition thereof, in the manufacture of a medicament for the treatment of a cancer. In certain embodiments, the cancer is a hematological cancer. In certain embodiments, the cancer is a lymphoid malignancy. In certain embodiments, the cancer is a leukemia, a lymphoma, or multiple myeloma. In certain embodiments, the cancer is a non-Hodgkin's lymphoma. In certain embodiments, the cancer is DLBCL. In certain embodiments, the cancer is ABC-DLBCL.

In certain embodiments, the methods of the invention comprise administering to the subject an effective amount of a compound of Formula I, or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formula I, or at different times than the compound of Formula I. For example, the compound of Formula I and any additional pharmaceutical agent(s) may be on the same dosing schedule or different dosing schedules. All or some doses of the compound of Formula I may be administered before all or some doses of an additional pharmaceutical agent, after all or some does an additional pharmaceutical agent, within a dosing schedule of an additional pharmaceutical agent, or a combination thereof. The timing of administration of the compound of Formula I and additional pharmaceutical agents may be different for different additional pharmaceutical agents.

In certain embodiments, the additional pharmaceutical agent comprises an agent useful in the treatment of cancer. In certain embodiments, the additional pharmaceutical agent is useful in the treatment of a hematological cancer. In certain embodiments, the additional pharmaceutical agent cancer is is useful in the treatment of a lymphoid malignancy. In certain embodiments, the additional pharmaceutical agent is useful in the treatment of a leukemia, a lymphoma, or multiple myeloma. In certain embodiments, the additional pharmaceutical agent is useful in the treatment of a non-Hodgkin's lymphoma. In certain embodiments, the additional pharmaceutical agent is useful in the treatment of DLBCL. In certain embodiments, the additional pharmaceutical agent is useful in the treatment of ABC-DLBCL. In certain embodiments, the additional pharmaceutical agent is an anti-cancer agent. In certain embodiments, the additional pharmaceutical agent is any anti-cancer agent recited herein. In certain embodiments, the additional pharmaceutical agent is an immunotherapy. In certain embodiments, the additional pharmaceutical agent is any immunotherapy recited herein.

In another aspect, the present disclosure provides methods for promoting the degradation of MALT1, the method comprising administering to the subject a compound of Formula I, or a pharmaceutically acceptable salt, co-crystal, tautomer, stereoisomer, solvate, hydrate, polymorph, isotopically enriched derivative, or prodrug, or composition thereof.

In another aspect, the present disclosure provides methods for promoting the degradation of MALT1 and binding an E3 ubiquitin ligase, the method comprising administering to the subject a compound of Formula I, or a pharmaceutically acceptable salt, co-crystal, tautomer, stereoisomer, solvate, hydrate, polymorph, isotopically enriched derivative, or prodrug, or composition thereof. In certain embodiments, the E3 ubiquitin ligase is Cereblon. In certain embodiments, the E3 ubiquitin ligase is VHL.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Compounds of Formula I may be prepared using the synthetic schemes and procedures described in detail below.

Preparation of Synthetic Intermediates

3-Chloro-1H-pyrazol-5-amine (4)

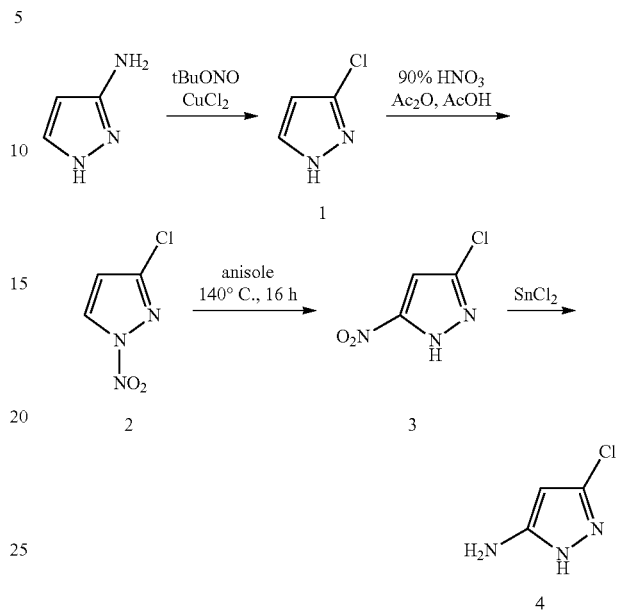

3-Chloro-1H-pyrazole (1)

Copper (II) chloride (65.0 g, 481 mmol) and conc. HCl (20 mL) were added to a solution of 1H-pyrazole-3-amine (20.0 g, 241 mmol) in acetonitrile (600 mL) at 0° C. The reaction mixture was stirred at 0° C. for 30 min, then isopentyl nitrite (56.4 g, 481 mmol) was added dropwise. The mixture was stirred at room temperature for 2 days, and then quenched with aq. ammonia (10%, 1 L). The aqueous phase was extracted with EtOAc (5×500 mL) and the combined organic phases were washed with brine, dried over anhydrous sodium sulfate, filtered and concentrated. The residue was purified by silica chromatography (hexane: EtOAc=20:1) to give the title compound (10.3 g, 42%) as a green oil. $^1$H NMR (400 MHz, CDCl$_3$): δ 12.84 (bs, 1H), 7.62 (s, 1H), 6.29 (s, 1H).

3-Chloro-1-nitro-pyrazole (2)

Conc. nitric acid (63%, 2.5 g, 39 mmol) was added to a solution of 3-chloro-1H-pyrazole (4.0 g, 39 mmol) in glacial acetic acid (5.2 mL) at 0° C. After stirring for 1 hour, acetic anhydride (15.5 g, 152 mmol) was added. The reaction mixture was stirred at room temperature for 2 hours then quenched with 10% sodium carbonate solution (100 mL), and extracted with EtOAc (3×100 mL). The combined organic phases were washed with brine, dried over anhydrous sodium sulfate, filtered and concentrated. The residue was purified by silica chromatography (hexane:EtOAc=10: 1) to give the title compound (4.1 g, 70%) as a yellow solid. $^1$H NMR (400 MHz, DMSO-d6): δ 8.91 (d, 1H), 6.91 (d, 1H).

3-Chloro-5-nitro-1H-pyrazole (3)

A solution of 3-chloro-1-nitro-pyrazole (4.0 g, 27 mmol) in anisole (20 mL) was heated to 140° C. in an autoclave and stirred at 140° C. overnight. After cooling to 0° C., the reaction mixture was diluted with hexane (200 mL), stirred for 30 min at 0° C., and filtered. The solid was collected, washed with hexane (10 mL), and dried to give the title compound (2.1 g, 51%) as a yellow solid. ¹H NMR (400 MHz, DMSO-d6): δ 14.96 (bs, 1H), 7.30 (s, 1H).

3-Chloro-1H-pyrazol-5-amine (4)

Tin (II) chloride (12.8 g, 68 mmol) was added in portions to a solution of 3-chloro-5-nitro-1H-pyrazole (2.0 g, 13.6 mmol) in methanol (200 mL) and conc. HCl (10 mL) at 0° C. The reaction mixture was stirred at room temperature for 6 hours, and the organic solvent was removed under reduced pressure. The residue was diluted with water (20 mL), neutralized to pH 7 with Na2CO3, then extracted with EtOAc (3×50 mL). The combined organic phases were washed with brine, dried over anhydrous sodium sulfate, filtered and concentrated to give the title compound (1.4 g, 87%), which was used without further purification. ¹H NMR (400 MHz, DMSO-d$_6$): δ 11.55 (bs, 1H), 5.26 (s, 2H), 5.21 (s, 1H).

7-[(1S)-1-[tert-Butoxycarbonyl(methyl)amino]ethyl]-2-chloro-pyrazolo[1,5-a]pyrimidine-6-carboxylic acid (7)

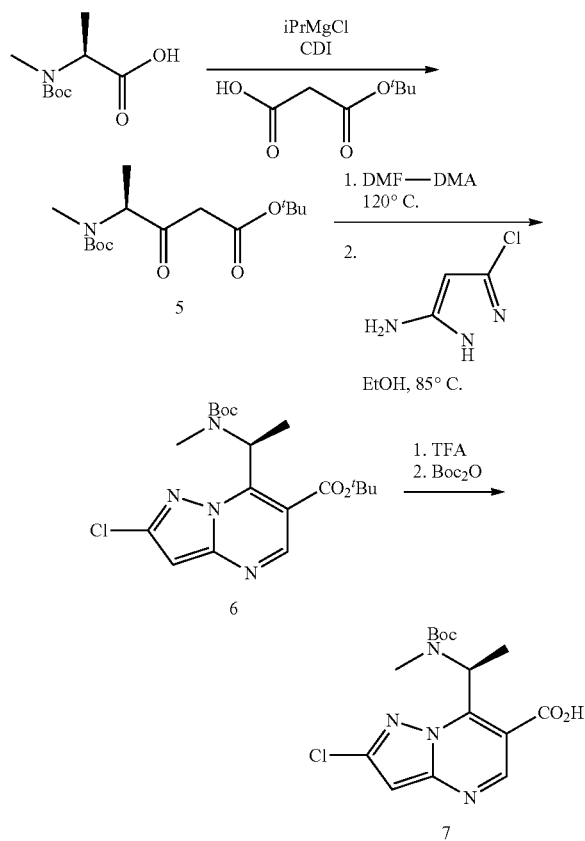

tert-Butyl (4S)-4-[tert-butoxycarbonyl(methyl)amino]-3-oxo-pentanoate (5)

CDI (4.4 g, 27 mmol) was added to a solution of N-(tert-butoxycarbonyl)-N-methyl-L-alanine (5.0 g, 24.6 mmol) in THF (100 mL) at 0° C. and the reaction mixture was stirred at room temperature for 3 hours. In a separate flask, isopropylmagnesium chloride (2M in THF, 73.8 mmol) was added dropwise to a solution of 3-(tert-butoxy)-3-oxopropanoic acid (5.9 g, 37 mmol) in THF (100 mL) at 0° C., the reaction mixture was stirred at room temperature for 3 hours and this solution was added dropwise to the acyl imidazole solution at 0° C. with stirring. The resulting mixture was allowed to warm to room temperature and stirred overnight, then quenched with 10% aqueous citric acid (100 mL). The organic phase was separated, the aqueous layer was extracted with EtOAc (2×100 mL), and the combined organic layers washed with saturated aq. NaHCO₃ solution and brine, dried over anhydrous sodium sulfate, filtered and concentrated. The residue was purified by silica chromatography (hexane:EtOAc=10:1) to give the title compound (1.60 g, 22%) as an oil. MS m/z 323.79 [M+Na]⁺.

tert-Butyl 7-[(1S)-1-[tert-butoxycarbonyl(methyl)amino]ethyl]-2-chloro-pyrazolo[1,5-a]pyrimidine-6-carboxylate (6)

A solution of compound tert-butyl (4S)-4-[tert-butoxycarbonyl(methyl)amino]-3-oxo-pentanoate (567 mg, 1.9 mmol) in DMF-DMA (0.25 mL) was heated at 120° C. for 1 hour, then cooled to 80° C., and a solution of 3-chloro-1H-pyrazol-5-amine (221 mg, 1.9 mmol) in EtOH (2.5 mL) was added to the reaction mixture. The resulting mixture was stirred for 2 hour at 80° C., cooled, concentrated under reduced pressure, and the residue was purified by silica chromatography (hexane:EtOAc=5:1 to 1:1) to give the title compound (340 mg, 44%) as an oil. ¹H NMR (400 MHz, CDCl₃): δ 8.61 (s, 1H), 6.66 (s, 1H), 5.96 (m, 1H), 3.08 (s, 3H), 1.76 (m, 3H), 1.60 (s, 9H), 1.47-0.90 (m, 9H). MS m/z 432.97 [M+Na]⁺.

7-[(1S)-1-[tert-Butoxycarbonyl(methyl)amino]ethyl]-2-chloro-pyrazolo[1,5-a]pyrimidine-6-carboxylic acid (7)

A solution of tert-butyl 7-[(1S)-1-[tert-butoxycarbonyl(methyl)amino]ethyl]-2-chloro-pyrazolo[1,5-a]pyrimidine-6-carboxylate (340 mg, 0.83 mmol) in TFA (5 mL) was stirred overnight at room temperature. The mixture was concentrated, the residue was dissolved in THF (10 mL) and K₂CO₃ solution (2N, 10 mL, 20 mmol), and Boc₂O (200 mg, 0.91 mol) was added. After stirring for 6 hours, the organic solvent was removed under reduced pressure, and the mixture diluted with H₂O (20 mL), and washed with hexane (3×30 mL). The aqueous phase was acidified with 1N HCl to pH 4, then extracted with ethyl acetate/THF (4:1, 3×50 mL). The combined organic layers were washed with brine, dried over anhydrous sodium sulfate, filtered and concentrated to give the title compound (230 mg, 79%). ¹H NMR (400 MHz, DMSO-d6): δ 13.90 (bs, 1H), 8.79 (s, 1H), 6.99 (s, 1H), 6.04 (s, 1H), 2.99 (s, 3H), 1.66 (m, 3H), 1.26-0.89 (m, 9H). MS m/z 353.15 [M−H]⁻.

(S)-1-(5-Chloro-6-(2H-1,2,3-triazol-2-yl)pyridin-3-yl)-3-(2-chloro-7-(1-(methylamino)ethyl)pyrazolo[1,5-a]pyrimidin-6-yl)urea hydrochloride (11)

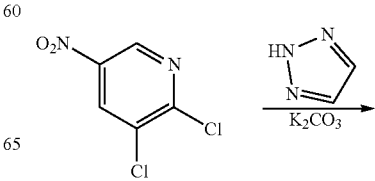

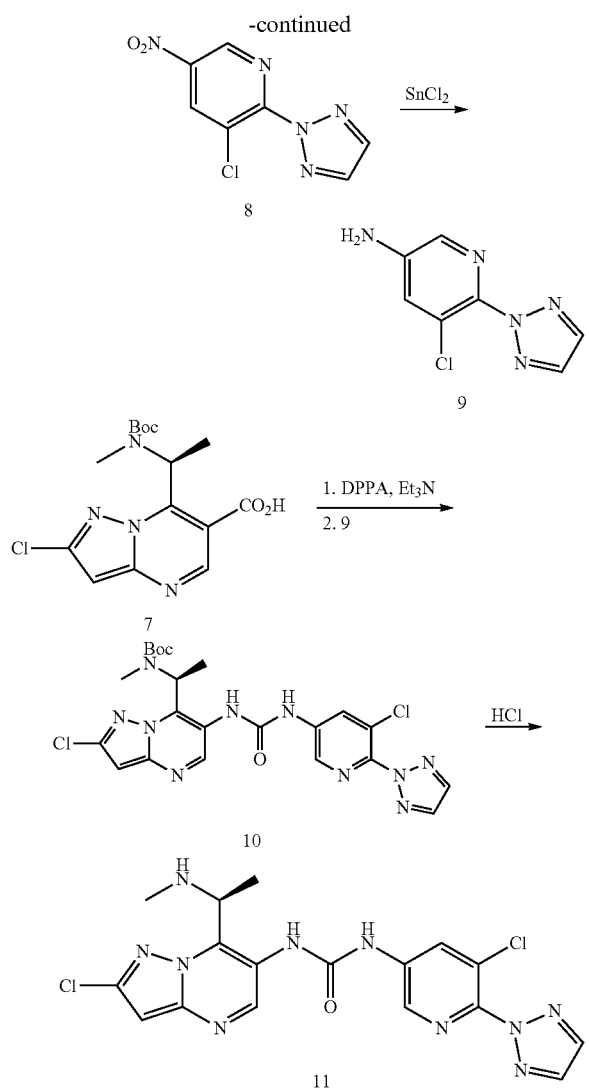

3-Chloro-5-nitro-2-(triazol-2-yl)pyridine (8)

1H-Triazole (760 mg, 11 mmol) was added to a suspension of 2,3-dichloro-5-nitro-pyridine (965 mg, 5 mmol) and anhydrous potassium carbonate (1.03 g, 7.5 mmol) in THF (50 mL), and the mixture was stirred overnight at room temperature. The mixture was diluted with EtOAc (100 mL), washed with water and brine, and the organic phase was dried over anhydrous sodium sulfate, filtered and concentrated. The residue was purified by silica chromatography (hexane:EtOAc=5:1 to 1:1) to give the title compound (505 mg, 44%). $^1$H NMR (400 MHz, DMSO-d6): δ 9.39 (d, 1H), 9.15 (d, 1H), 8.34 (s, 2H).

5-Chloro-6-(triazol-2-yl)pyridin-3-amine (9)

Tin(II) chloride dihydrate (4.75 g, 21 mmol) was added in portions to a suspension of 3-chloro-5-nitro-2-(triazol-2-yl)pyridine (950 mg, 4.2 mmol) in conc. HCl (25 mL) and EtOH (100 mL) at room temperature, then the mixture was stirred overnight. The solvent was removed under reduced pressure, and the residue was diluted with H$_2$O (100 mL), basicified with 3 N aq. NaOH solution to pH 9, then extracted with EtOAc (2×100 mL). The combined organic layers were washed with brine, dried over anhydrous sodium sulfate, filtered and concentrated to give the title compound (795 mg, 97%) as a yellow solid. $^1$H NMR (400 MHz, DMSO-d6): δ 8.05 (s, 2H), 7.82 (d, 1H), 7.20 (d, 1H), 6.21 (bs, 2H). MS m/z 195.95 [M+H]$^+$.

tert-Butyl (S)-(1-(2-chloro-6-(3-(5-chloro-6-(2H-1,2,3-triazol-2-yl)pyridin-3-yl)ureido)pyrazolo[1,5-a]pyrimidin-7-yl)ethyl)(methyl)carbamate (10)

Diphenylphosphoryl azide (0.20 mL) and triethylamine (302 mg, 3 mmol) were added to a solution of 7-[(1S)-1-[tert-butoxycarbonyl(methyl)amino]ethyl]-2-chloro-pyrazolo[1,5-a]pyrimidine-6-carboxylic acid (283 mg, 0.8 mmol) in dioxane (10 mL). The resulting yellow solution was stirred at room temperature for 30 minutes. 5-Chloro-6-(triazol-2-yl)pyridin-3-amine (156 mg, 0.8 mmol) was added and the reaction mixture was heated to 100° C. and stirred for 1 hour. After cooling to room temperature, the mixture was diluted with water (30 mL), extracted with EtOAc (3×30 mL). The combined organic layers were washed with saturated aq. NaHCO$_3$ solution and brine, dried over anhydrous sodium sulfate, filtered and concentrated. The residue was purified by prep-HPLC to give the title compound (170 mg, 39%). MS m/z 547.38 [M+H]$^+$.

(S)-1-(5-Chloro-6-(2H-1,2,3-triazol-2-yl)pyridin-3-yl)-3-(2-chloro-7-(1-(methylamino)ethyl)pyrazolo[1,5-a]pyrimidin-6-yl)urea hydrochloride (11)

A solution of HCl in dioxane (4N, 10 mL) was added dropwise to a solution of tert-butyl (S)-(1-(2-chloro-6-(3-(5-chloro-6-(2H-1,2,3-triazol-2-yl)pyridin-3-yl)ureido)pyrazolo[1,5-a]pyrimidin-7-yl)ethyl)(methyl)carbamate (170 mg, 0.31 mmol) in EtOAc (10 mL) at 0° C. The resulting mixture was stirred for 3 hours at room temperature, then concentrated under reduced pressure to give the title compound (125 mg, 83%) as the HCl salt. $^1$H NMR (400 MHz, D$_2$O): δ 8.45 (s, 1H), 8.40 (d, 1H), 8.24 (d, 1H), 7.92 (s, 2H), 6.76 (s, 1H), 5.05 (m, 1H), 2.55 (s, 3H), 1.74 (d, 3H). MS m/z 447.4 [M+H]$^+$.

2-Chloro-7-[(1S)-1-methoxyethyl]pyrazolo[1,5-a]pyrimidine-6-carboxylic acid (17)

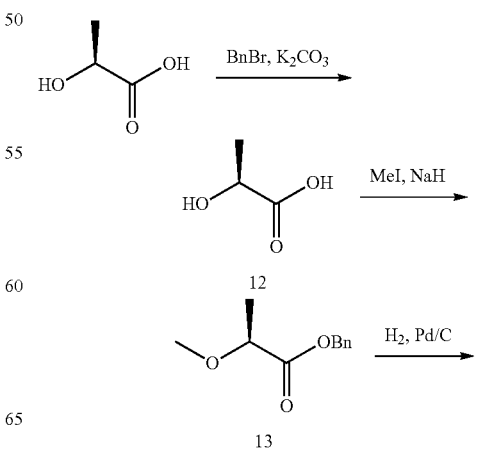

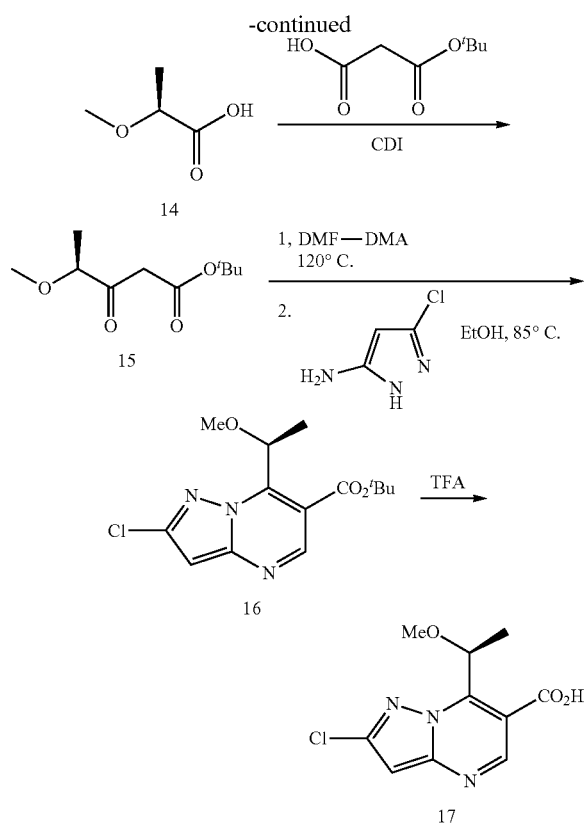

Benzyl (2S)-2-hydroxypropanoate (12)

Benzyl bromide (242 g, 1.42 mol) was added to a suspension of (2S)-2-hydroxy propanoic acid (106 g, 1.18 mol) and cesium carbonate (503 g, 1.53 mol) in acetonitrile (1 L) at room temperature, and the resulting mixture was heated under reflux for 2 days. After cooling to room temperature, the mixture was quenched with water (2 L), extracted with EtOAc (3×800 mL) and the combined organic phases were washed with brine, dried over anhydrous sodium sulfate, filtered and concentrated. The residue was purified by silica chromatography (hexane:EtOAc=10:1 to 5:1) to give the title compound (150 g, 70%). $^1$H NMR (400 MHz, CDCl$_3$): δ 7.38 (m, 5H), 5.22 (s, 2H), 4.33 (q, 1H), 1.44 (d, 3H).

Benzyl (2S)-2-methoxypropanoate (13)

NaH (60%, 15.0 g, 374 mmol) was added to a solution of benzyl (2S)-2-hydroxypropanoate (33.7 g, 187 mmol) in THF (100 mL) at 0° C. under N$_2$. The mixture was stirred for 30 minutes at room temperature, cooled to 0° C., and iodomethane (53.1 g, 374 mmol) was added dropwise. The mixture was stirred at room temperature overnight, quenched with water (500 mL), extracted with EtOAc (3×400 mL) and the combined organic phases were washed with brine (400 mL×1), dried over anhydrous sodium sulfate, filtered and concentrated. The residue was purified by silica chromatography (hexane:EtOAc=20:1) to give the title compound (7.6 g, 21%). $^1$H NMR (400 MHz, CDCl$_3$): δ 7.35 (m, 5H), 5.22 (s, 2H), 3.95 (q, 1H), 3.39 (s, 3H), 1.42 (d, 3H).

(2S)-2-Methoxypropanoic acid (14)

A suspension of benzyl (2S)-2-methoxypropanoate (7.6 g, 39 mmol) and Pd/C (10%, 0.7 g) in EtOH (100 mL) was stirred under hydrogen at room temperature for 3 hours, then filtered. The filtrate was concentrated under reduced pressure to give the title compound (3.76 g, 92%), which was used without further purification. $^1$H NMR (400 MHz, CDCl$_3$): δ 8.28 (bs, 1H), 3.94 (q, 1H), 3.45 (s, 3H), 1.48 (d, 3H).

tert-Butyl (4S)-4-methoxy-3-oxo-pentanoate (15)

CDI (4.39 g, 27.1 mmol) was added to a solution of (2S)-2-methoxypropanoic acid (2.56 g, 24.6 mmol) in THF (100 mL) at 0° C. and the reaction mixture was stirred at room temperature for 3 hours. In a separate flask, isopropylmagnesium chloride (2 M in THF, 37 mL, 74 mmol) was added dropwise to a solution of 3-(tert-butoxy)-3-oxopropanoic acid (5.91 g, 37 mmol) in THF (100 mL) at 0° C., the reaction mixture was stirred at room temperature for 3 hours and this solution was added dropwise to the acyl imidazole solution at 0° C. with stirring The resulting mixture was allowed to warm to room temperature and stirred overnight, then quenched with 10% aqueous citric acid (100 mL). The aqueous layer was extracted with EtOAc (3×100 mL) and the combined organic phases were washed with brine, dried over anhydrous sodium sulfate, filtered and concentrated. The residue was purified by silica chromatography (hexane:EtOAc=30:1) to give the title compound (3.90 g, 78%). $^1$H NMR (400 MHz, CDCl$_3$): δ 3.83 (q, 1H), 3.54 (2d, 2H), 3.46 (s, 3H), 1.47 (s, 9H), 1.31 (d, 3H).

tert-Butyl 2-chloro-7-[(1S)-1-methoxyethyl]pyrazolo[1,5-a]pyrimidine-6-carboxylate (16)

A solution of tert-butyl (4S)-4-methoxy-3-oxo-pentanoate (1.96 g, 9.7 mmol) in DMF-DMA (1.25 mL) was heated at 120° C. for 1 hour, then cooled to 80° C., and a solution of 3-chloro-1H-pyrazol-5-amine (1.14 g, 0.97 mmol) in EtOH (12.5 mL) was added. The resulting mixture was stirred for 2 hours at 80° C., then concentrated under reduced pressure. The residue was purified by silica chromatography (hexane:EtOAc=5:1 to 1:1) to give the title compound (1.60 g, 53%). $^1$H NMR (400 MHz, DMSO-d6): δ 8.66 (s, 1H), 7.05 (s, 1H), 5.26 (q, 1H), 3.22 (s, 3H), 1.62 (d, 3H), 1.56 (s, 9H). MS m/z 312.24 [M+H]$^+$.

2-Chloro-7-[(1S)-1-methoxyethyl]pyrazolo[1,5-a]pyrimidine-6-carboxylic acid (17)

A solution of tert-butyl 2-chloro-7-[(1S)-1-methoxyethyl]pyrazolo[1,5-a]pyrimidine-6-carboxylate (160 mg, 0.053 mmol) in TFA (1 mL) was stirred overnight at room temperature. The solvent was removed to give the title compound (130 mg, 99%), which was used without further purification. $^1$H NMR (400 MHz, DMSO-d6): δ 13.75 (bs, 1H), 8.72 (s, 1H), 7.04 (s, 1H), 5.40 (q, 1H), 3.21 (s, 3H), 1.65 (d, 3H). MS m/z 256.31 [M+H]$^+$.

2-Chloro-7-isopropylpyrazolo[1,5-a]pyrimidine-6-carboxylic acid (20)

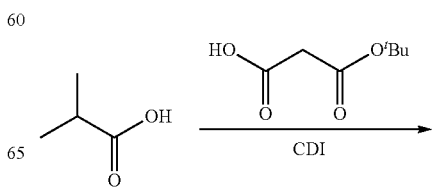

-continued

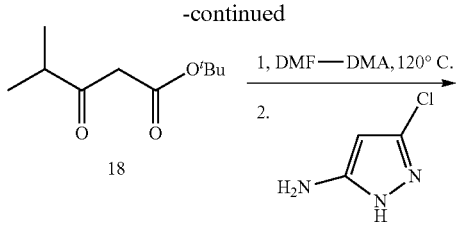

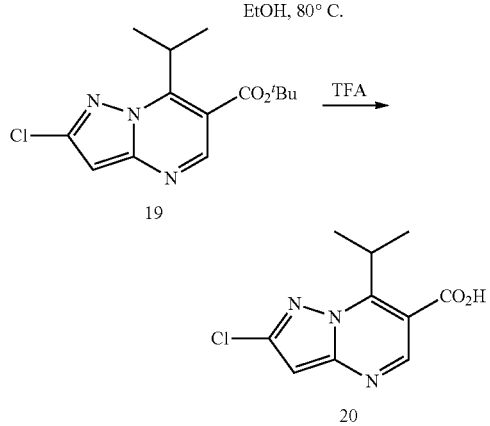

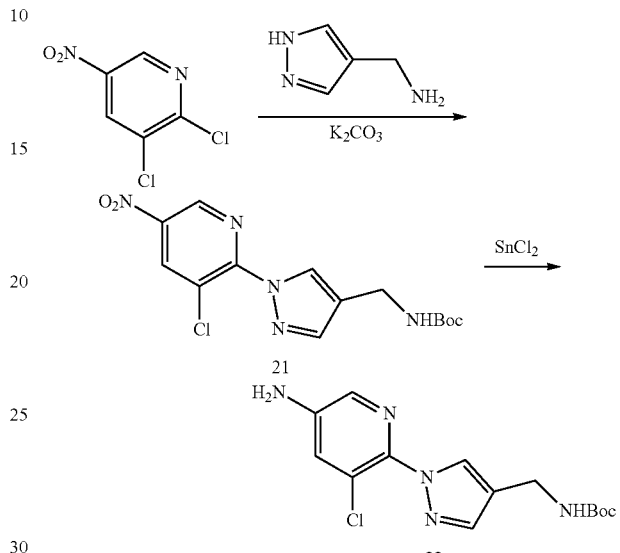

tert-Butyl 4-methyl-3-oxopentanoate (18)

CDI (8.1 g, 50.0 mmol) was added to a solution of isobutyric acid (4 g, 45.5 mmol) in THF (120 mL) at 0° C. and the reaction mixture was stirred at room temperature for 3 hours. In a separate flask, isopropylmagnesium chloride (2M in THF, 69 mL, 136.5 mmol) was added dropwise to a solution of malonic acid mono-tert-butyl ester (11.0 g, 68.3 mmol) in THF (120 mL) at 0° C. This reaction mixture was stirred at room temperature for 3 hours then added dropwise to the above acyl imidazole solution at 0° C. The reaction mixture was allowed to warm to room temperature and stirred overnight, poured into ice-cold 10% aqueous citric acid (300 mL) and the aqueous layer was extracted with EtOAc (3×300 mL). The combined organic phases were washed with brine, dried over anhydrous sodium sulfate, filtered and concentrated to give the title compound (8.3 g, 98% yield), used without further purification. $^1$H NMR (400 MHz, CDCl$_3$): δ 3.41 (s, 2H), 2.72 (m, 1H), 1.43 (s, 9H), 1.13 (d, 6H).

tert-Butyl 2-chloro-7-isopropylpyrazolo[1,5-a]pyrimidine-6-carboxylate (19)

A solution of tert-butyl 4-methyl-3-oxopentanoate (2.52 g, 13.6 mmol) in DMF-DMA (1.8 mL) was heated at 120° C. for 1 hour. The solution was cooled to 80° C. and a solution of 3-chloro-1H-pyrazol-5-amine (1.6 g, 13.6 mmol) in EtOH (21 mL) was added. The resulting mixture was stirred for 2 hours at 80° C. The solvent was removed in vacuo then concentrated under reduced pressure. The residue was purified by silica chromatography (petroleum ether:EtOAc=40:1) to give the title compound (2.1 g, 52% yield). $^1$H NMR (400 MHz, DMSO-d6): δ 8.76 (s, 1H), 6.97 (s, 1H), 4.30 (m, 1H), 1.57 (s, 9H), 1.52 (d, J=7.2 Hz, 6H). MS m/z 296.45 [M+H]$^+$.

2-Chloro-7-Isopropylpyrazolo[1,5-a]Pyrimidine-6-Carboxylic Acid (20)

A solution of compound 19 (300 mg, 1.0 mmol) in TFA/DCM (6 mL/3 mL) was stirred for 1 hour at room temperature. The solvent was concentrated under reduced pressure to give the title compound (257 mg, 100% yield), used without further purification.

tert-Butyl N-[[1-(5-amino-3-chloro-2-pyridyl)pyrazol-4-yl]methyl]carbamate (22)

tert-Butyl N-[[1-(3-chloro-5-nitro-2-pyridyl)pyrazol-4-yl]methyl]carbamate (21)

A suspension of 2,3-dichloro-5-nitro-pyridine (579 mg, 3.0 mmol), tert-butyl N-(1H-pyrazol-4-ylmethyl)carbamate (592 mg, 3.0 mmol) and potassium carbonate (621 mg, 4.5 mmol) in DMF (10 mL) was heated to 50° C. and stirred for 18 hours, then cooled and and filtered. The filtrate was diluted with water (100 mL) and extracted with EtOAc (3×100 mL). The combined organic phases were washed with brine, dried over anhydrous sodium sulfate, filtered and concentrated. The residue was purified by silica chromatography (hexane:EtOAc=20:1) to give the title compound (705 mg, 66%). $^1$H NMR (400 MHz, CDCl$_3$): δ 9.20 (d, 1H), 8.70 (d, 1H), 8.35 (s, 1H), 7.84 (s, 1H), 4.85 (bs, 1H), 4.30 (m, 2H), 1.26 (s, 9H). MS m/z 353.85 [M+H]$^+$.

tert-Butyl N-[[1-(5-amino-3-chloro-2-pyridyl)pyrazol-4-yl]methyl]carbamate (22)

Iron powder (158 mg, 2.8 mmol) was added to a solution of tert-butyl N-[[1-(3-chloro-5-nitro-2-pyridyl)pyrazol-4-yl]methyl]carbamate (100 mg, 0.28 mmol) in saturated NH$_4$Cl solution (0.5 mL) and EtOH (5 mL). The mixture was heated under reflux and stirred for 1 hour, then cooled to room temperature, filtered through Celatom and concentrated. The residue was purified by silica chromatography (DCM:MeOH=100:1 to 20:1) to give the title compound (81 mg, 88%) as a white solid. $^1$H NMR (400 MHz, DMSO-d6): δ 7.79 (s, 1H), 7.76 (d, 1H), 7.53 (s, 1H), 7.26 (m, 1H), 7.16 (d, 1H), 5.96 (s, 2H), 4.03 (m, 2H), 1.39 (s, 9H). MS m/z 324.35 [M+H]$^+$.

tert-Butyl N-[2-[(3-amino-5-chloro-2-pyridyl)oxy]ethyl]carbamate (24)

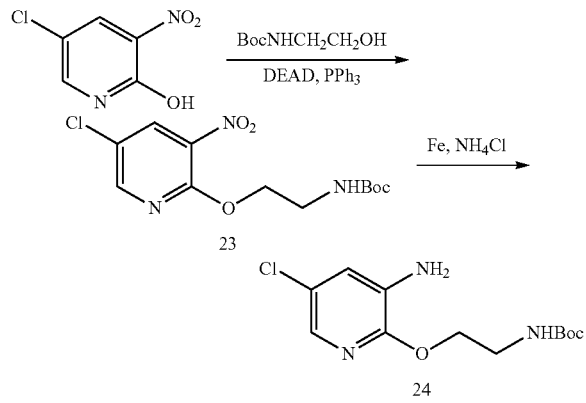

tert-Butyl N-[2-[(5-chloro-3-nitro-2-pyridyl)oxy]ethyl]carbamate (23):

DEAD (6.98 g, 40 mmol) was added to a suspension of 5-chloro-3-nitro-pyridin-2-ol (3.50 g, 20 mmol), tert-butyl N-(2-hydroxyethyl)carbamate (3.23 g, 20 mmol) and PPh₃ (11.56 g, 44 mmol) in THF (70 mL) at 0° C. After stirring at room temperature overnight, the reaction was poured into water (250 mL), and extracted with EtOAc (3×100 mL). The combined organic phases were washed with brine, dried over anhydrous sodium sulfate, filtered and concentrated. The residue was purified by silica chromatography (hexane: EtOAc=100:1 to 10:1) to give the title compound (2.4 g, 38%) as a white solid. $^1$H NMR (400 MHz, CDCl₃): δ 8.35 (d, 1H), 8.30 (d, 1H), 5.02 (s, 1H), 4.53 (t, 2H), 3.59 (m, 2H), 1.45 (s, 9H). MS m/z 318.24 [M+H]$^+$.

tert-Butyl N-[2-[(3-amino-5-chloro-2-pyridyl)oxy]ethyl]carbamate (24):

Iron powder (4.22 g, 75.5 mmol) was added to a solution of tert-butyl N-[2-[(5-chloro-3-nitro-2-pyridyl)oxy]ethyl]carbamate (2.40 g, 7.6 mmol) in saturated NH₄Cl solution (5 mL) and EtOH (20 mL). The mixture was stirred under reflux for 3 hours. The reaction was cooled to room temperature, then filtered through Celatom and concentrated. The residue was purified by silica chromatography (hexane: EtOAc=10:1 to 1:1) to give the title compound (1.60 g, 74%) as a yellow solid. $^1$H NMR (400 MHz, CDCl₃): δ 7.45 (s, 1H), 6.87 (s, 1H), 4.94 (m, 1H), 4.39 (t, 2H), 3.55 (m, 2H), 1.40 (s, 9H). MS m/z 288.06 [M+H]$^+$.

(S)-1-(6-(4-(Aminomethyl)-1H-pyrazol-1-yl)-5-chloropyridin-3-yl)-3-(2-chloro-7-(1-methoxyethyl)pyrazolo[1,5-a]pyrimidin-6-yl)urea hydrochloride (26);
(S)-1-(2-(2-Aminoethoxy)-5-chloropyridin-3-yl)-3-(2-chloro-7-(1-methoxyethyl)pyrazolo[1,5-a]pyrimidin-6-yl)urea hydrochloride (28)

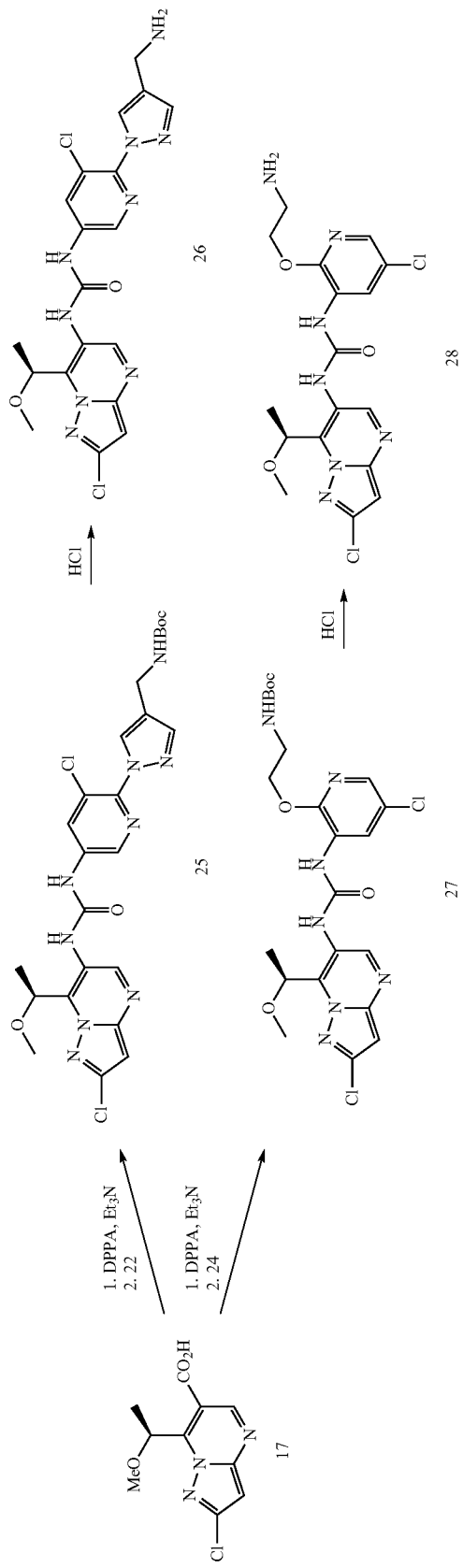

tert-Butyl N-[[1-[5-[[2-chloro-7-[(1S)-1-methoxyethyl]pyrazolo[1,5-a]pyrimidin-6-yl]carbamoylamino]-2-pyridyl]pyrazol-4-yl]methyl]carbamate (25)

Diphenylphosphoryl azide (0.25 mL) and triethylamine (0.4 mL, 3 mmol) were added to a solution of 2-chloro-7-[(1S)-1-methoxyethyl]pyrazolo[1,5-a]pyrimidine-6-carboxylic acid (255 mg, 1.0 mmol) in dioxane (10 mL). The resulting yellow solution was stirred at room temperature for 30 minutes. tert-Butyl N-[[1-(5-amino-3-chloro-2-pyridyl)pyrazol-4-yl]methyl]carbamate (387 mg, 1.2 mmol) was added and the reaction mixture was stirred under reflux for 1 hour. After cooling, the mixture was diluted with water (50 mL), extracted with EtOAc (3×30 mL), and the combined organic phases were washed with saturated $NaHCO_3$ solution and brine, dried over anhydrous sodium sulfate, filtered and concentrated. The residue was purified by prep-HPLC to give the title compound (175 mg, 32%).

(S)-1-(6-(4-(Aminomethyl)-1H-pyrazol-1-yl)-5-chloropyridin-3-yl)-3-(2-chloro-7-(1-methoxyethyl)pyrazolo[1,5-a]pyrimidin-6-yl)urea hydrochloride (26)

A solution of HCl in dioxane (4N, 10 mL) was added dropwise to a solution of tert-butyl N-[[1-[5-[[2-chloro-7-[(1S)-1-methoxyethyl]pyrazolo[1,5-a]pyrimidin-6-yl]carbamoylamino]-2-pyridyl]pyrazol-4-yl]methyl]carbamate (150 mg, 0.26 mmol) in EtOAc (10 mL) at 0° C. The resulting mixture was stirred for 3 hours at room temperature, then concentrated under reduced pressure to give the title compound (113 mg, 91%) as the HCl salt. $^1H$ NMR (400 MHz, DMSO-d6): δ 10.80 (s, 1H), 8.90 (s, 1H), 8.80 (s, 1H), 8.55 (s, 1H), 8.41 (s, 1H), 8.37 (bs, 3H), 8.31 (s, 1H), 7.89 (s, 1H), 6.94 (s, 1H), 5.42 (m, 1H), 4.00 (m, 2H), 3.32 (s, 3H), 1.59 (d, 3H). MS m/z 476.4 $[M+H]^+$.

tert-Butyl N-[2-[[5-chloro-3-[[2-chloro-7-[(1S)-1-methoxyethyl]pyrazolo[1,5-a]pyrimidin-6-yl]carbamoylamino]-2-pyridyl]oxy]ethyl]carbamate (27)

Diphenylphosphoryl azide (0.26 mL) and triethylamine (0.4 mL, 3 mmol) were added to a solution of 2-chloro-7-[(1S)-1-methoxyethyl]pyrazolo[1,5-a]pyrimidine-6-carboxylic acid (255 mg, 1.0 mmol) in dioxane (10 mL). The resulting yellow solution was stirred at room temperature for 30 minutes, then tert-butyl N-[2-[(3-amino-5-chloro-2-pyridyl)oxy]ethyl]carbamate (574 mg, 2 mmol) was added and the mixture heated under reflux for 1 hour. After cooling to room temperature, the mixture was diluted with water (50 mL), extracted with EtOAc (3×30 mL). The combined organic phases were washed with saturated $NaHCO_3$ solution and brine, dried over anhydrous sodium sulfate, filtered and concentrated. The residue was purified by HPLC to give the title compound (133 mg, 25%).

(S)-1-(2-(2-Aminoethoxy)-5-chloropyridin-3-yl)-3-(2-chloro-7-(1-methoxyethyl)pyrazolo[1,5-a]pyrimidin-6-yl)urea hydrochloride (28)

A solution of HCl in dioxane (4N, 5 mL) was added dropwise to a solution of tert-butyl N-[2-[[5-chloro-3-[[2-chloro-7-[(1S)-1-methoxyethyl]pyrazolo[1,5-a]pyrimidin-6-yl]carbamoylamino]-2-pyridyl]oxy]ethyl]carbamate (200 mg, 0.37 mmol) in EtOAc (5 mL) at 0° C. The resulting mixture was stirred for 3 hours at room temperature, and then concentrated under reduced pressure to give the title compound (150 mg, 92%) as the HCl salt. $^1H$ NMR (400 MHz, $D_2O$): δ 8.50 (s, 1H), 8.06 (d, 1H), 7.62 (d, 1H), 6.59 (s, 1H), 5.24 (m, 1H), 4.46 (m, 2H), 3.39 (m, 2H), 3.20 (s, 3H), 1.49 (d, 3H). MS m/z 440.4 $[M+H]^+$.

Compounds 29 and 30 were prepared in in an analogous manner to compound 26, employing the indicated starting materials and tert-butyl N-[[1-(5-amino-3-chloro-2-pyridyl)pyrazol-4-yl]methyl]carbamate (19), followed by deprotection of the Boc group with HCl in dioxane. The compounds could also be isolated as the TFA salt after further purification by prep HPLC.

| Compound | Name/Structure | Characterization | Starting material |
|---|---|---|---|
| 29 | 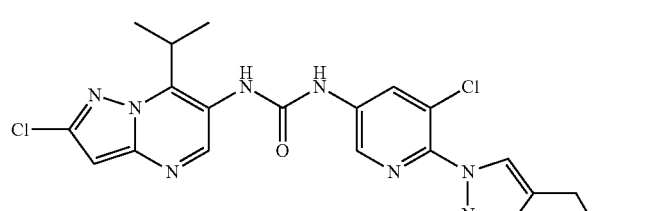<br>1-(6-(4-(Aminomethyl)-1H-pyrazol-1-yl)-5-chloropyridin-3-yl)-3-(2-chloro-7-isopropylpyrazolo[1,5-a]pyrimidin-6-yl)urea hydrochloride | $^1H$ NMR (500 MHz, d6-DMSO): 10.39 (br, 1H), 9.14 (s, 1H), 8.58 (s, 1H), 8.53 (d, 1H), 8.36 (s, 1H), 8.33 (m, 3H), 8.30 (s, 1H), 7.88 (s, 1H), 6.91 (s, 1H), 4.00 (m, 2H), 3.87 (m, 1H), 1.49 (d, 6H); m/z [M + 1]+: 460.4 | (20) |

| Compound | Name/Structure | Characterization | Starting material |
|---|---|---|---|
| 30 | 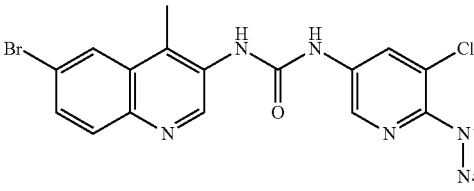<br>1-(6-(4-(Aminomethyl)-1H-pyrazol-1-yl)-5-chloropyridin-3-yl)-3-(6-bromo-4-methylquinolin-3-yl)urea 2,2,2-trifluoroacetate | 9.97 (s, 1H), 9.20 (s, 1H), 9.10 (s, 1H), 8.57 (d, 1H), 8.41 (d, 1H), 8.34 (d, 1H), 8.27 (s, 1H), 8.10 (br, 3H), 7.95 (d, 1H), 7.85 (m, 2H), 4.03 (m, 2H), 2.59 (s, 3H); m/z [M + 1]+: 488.03 | 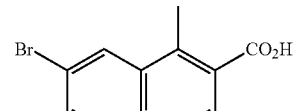<br>6-Bromo-4-methylquinoline-3-carboxylic acid |

2-(2,6-Dioxopiperidin-3-yl)-4-fluoroisoindoline-1,3-dione (31) was prepared according to the procedures reported in U.S. Patent Application Publication No. 2016/0058872, the contents of which are incorporated herein by reference.

3-(2-(2-((2-(2,6-Dioxopiperidin-3-yl)-1-oxoisoindolin-4-yl)amino)ethoxy)ethoxy)propanoic acid (36)

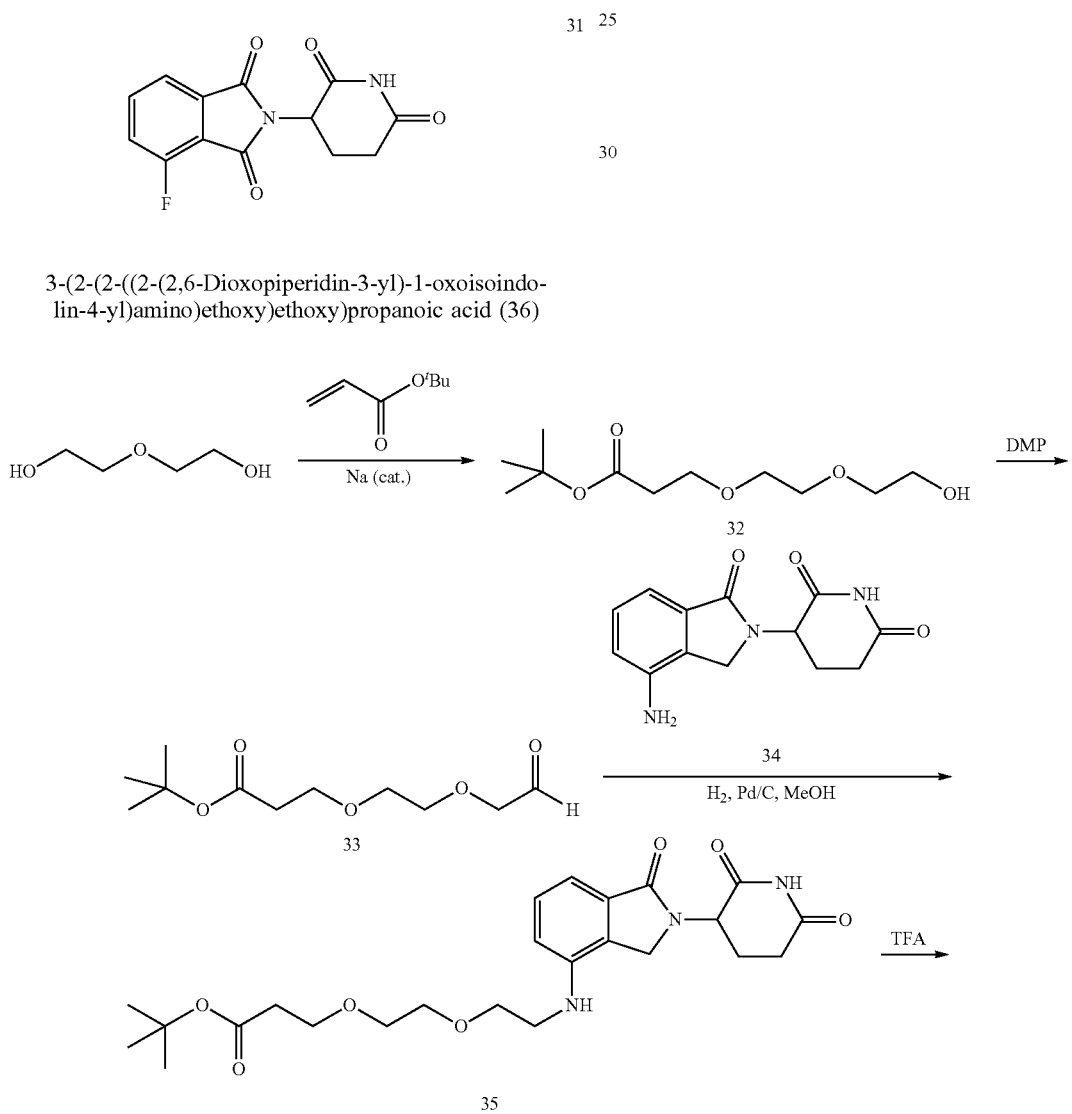

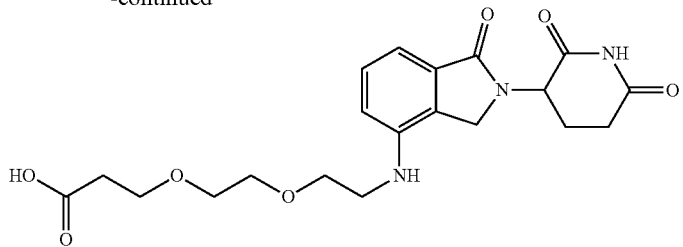

36 tert-Butyl 3-(2-(2-hydroxyethoxy)ethoxy)propanoate (32)

Metal sodium (64 mg, 0.03 eq) was added to a solution of diethylene glycol (29.5 g, 0.278 mmol) in THF (100 mL). The mixture was stirred for 1 hour to dissolve the sodium, then tert-butyl acrylate (12.4 g, 97 mmol) was added. The resulting mixture was stirred for 2 days, then concentrated under reduced pressure and the residue purified by silica chromatography (hexane:EtOAc=1:1) to give the title compound (9.1 g, 40%) as a colorless oil. $^1$H NMR (400 MHz, CDCl$_3$): δ 3.75 (m, 4H), 3.64 (m, 6H), 2.53 (t, 2H), 2.40 (s, 1H), 1.45 (s, 9H).

tert-Butyl 3-(2-(2-oxoethoxy)ethoxy)propanoate (33)

tert-Butyl 3-(2-(2-hydroxyethoxy)ethoxy)propanoate (8.6 g, 37 mmol) was added to a suspension of Dess-Martin periodinane (DMP, 18.8 g, 44 mmol) and pyridine (7.0 g, 88 mmol) in DCM (150 mL) at 0° C. The resulting mixture was stirred at room temperature for 16 hours, then filtered, washed with DCM (3×50 mL). The filtrate and washings were combined and washed with saturated NaHCO$_3$ solution and brine, dried over anhydrous sodium sulfate, filtered and concentrated. The residue was purified by silica chromatography (hexane:EtOAc=10:1 to 3:1) to give the title compound (4.1 g, 48%) as a yellow oil. $^1$H NMR (400 MHz, CDCl$_3$): δ 9.76 (s, 1H), 4.16 (s, 2H), 3.50-3.80 (m, 6H), 2.53 (t, 2H), 1.46 (s, 9H).

tert-Butyl 3-(2-(2-((2-(2,6-dioxopiperidin-3-yl)-1-oxoisoindolin-4 yl)amino)ethoxy)ethoxy)propanoate (35)

10% pd/c (100 mg) was added to a solution of lenalidomide (34) (1.0 g, 3.9 mmol) and tert-butyl 3-(2-(2-oxoethoxy)ethoxy)propanoate (1.8 g, 7.7 mmol) in MeOH (200 mL). The mixture was stirred at room temperature under an atmosphere of hydrogen for 16 hours. The solid was filtered, and the filtrate was concentrated under reduced pressure. The residue was purified by silica chromatography (DCM:MeOH=30:1 to 20:1) and then by HPLC to give the title compound (425 mg, 23%).

3-(2-(2-((2-(2,6-Dioxopiperidin-3-yl)-1-oxoisoindolin-4-yl)amino)ethoxy)ethoxy)propanoic acid (36)

TFA (1.5 mL) was added to a solution of tert-butyl 3-(2-(2-((2-(2,6-dioxopiperidin-3-yl)-1-oxoisoindolin-4-yl)amino)ethoxy)ethoxy)propanoate (400 mg, 0.84 mmol) in DCM (6 mL) at 0° C. The mixture was stirred at room temperature for 1 hour, and the solvent was removed under reduced pressure to give the title compound (380 mg, 92% yield) as TFA salt. $^1$H NMR (400 MHz, DMSO-d6): δ 11.00 (s, 1H), 7.30 (d, 1H), 6.95 (d, 1H), 6.80 (d, 1H), 5.10 (m, 1H), 4.15 (2d, 2H), 3.60 (m, 2H), 3.50 (m, 2H), 3.36 (m, 6H), 2.95 (m, 1H), 2.62 (m, 1H), 2.44 (t, 2H), 2.30 (m, 1H), 2.00 (m, 1H). MS m/z 420.7 [M+H]$^+$.

Compounds 37-39 were prepared in an analogous manner to compound 36, employing the indicated starting material and either lenalidomide (34) or pomalidomide.

| Compound | Structure/Name | Characterization | Starting materials |
|---|---|---|---|
| 37 | 1-((2-(2,6-Dioxopiperidin-3-yl)-1-oxoisoindolin-4-yl)amino)-3,6,9,12-tetraoxapentadecan-15-oic acid | $^1$H NMR (400 MHz, d$_6$-DMSO): δ 12.30 (br s, 1H), 11.04 (s, 1H), 7.28 (m, 1H), 6.94 (d, 1H), 6.80 (d, 1H), 5.64 (m, 1H), 5.10 (m, 1H), 4.21 (d, 1H) 4.15 (d, 1H), 3.50 (m, 16H), 3.31 (m, 2H), 2.92 (m, 1H), 2.63 (m, 1H), 2.42 (t, 2H), 2.32 (m, 1H), 2.03 | 2,2-((oxybis(ethane-2,1-diyl))bis(oxy))bis(ethan-1-ol) + (34) |

| Compound | Structure/Name | Characterization | Starting materials |
|---|---|---|---|
| | | (m, 1H); m/z [M + 1]⁺: 507.95 | |
| 38 | 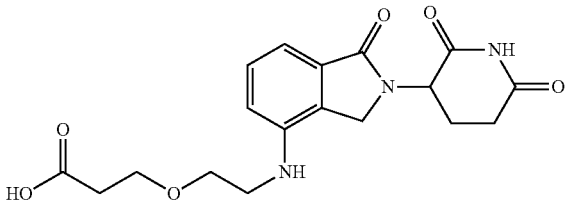 [SMILES: O=C(O)CCOCCNc1cccc2c1CN(C1CCC(=O)NC1=O)C2=O]<br>3-(2-((2-(2,6-Dioxopiperidin-3-yl)-1-oxoisoindolin-4-yl)amino)ethoxy)propanoic acid | $^1$H NMR (400 MHz, d$_6$-DMSO): δ 12.23 (br s, 1H), 11.04 (s, 1H), 7.29 (m, 1H), 6.95 (d, 1H), 6.80 (d, 1H), 5.57 (br s, 1H), 5.12 (m, 1H), 4.21 (d, 1H) 4.15 (d, 1H), 3.63 (t, 2H), 3.57 (t, 2H), 3.28 (m, 2H), 2.92 (m, 1H), 2.60 (m, 1H), 2.47 (m, 2H), 2.33 (m, 1H), 2.03 (m, 1H); m/z [M + 1]⁺: 376.6 | ethane-1,2-diol + (34) |
| 39 | 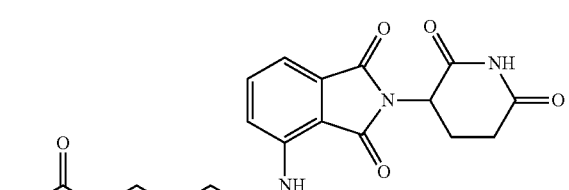<br>3-(2-((2-(2,6-Dioxopiperidin-3-yl)-1,3-dioxoisoindolin-4-yl)amino)ethoxy)propanoic acis | $^1$H NMR (400 MHz, CDCl$_3$): δ 8.60 (s, 1H), 7.50 (m, 1H), 7.11 (d, 1H), 6.92 (d, 1H), 4.95 (m, 1H), 3.78 (t, 2H), 3.71 (t, 2H), 3.47 (t, 2H), 2.88 (m, 1H), 2.78 (m, 2H), 2.62 (t, 2H), 2.13 (m, 1H); m/z 387.6 [M − H]⁻. | ethane-1,2-diol + pomalidomide |

3-(2-(2-((2-(2,6-Dioxopiperidin-3-yl)-1,3-diox-oisoindolin-4-yl)amino)ethoxy)ethoxy) propanoic acid (41)

50

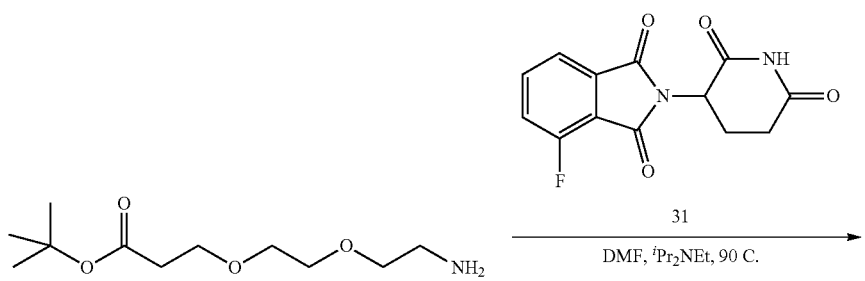

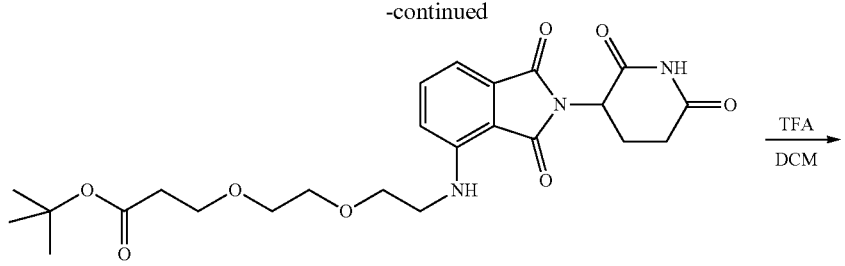

tert-Butyl 3-(2-(2-(2-(2,6-dioxopiperidin-3-yl)-1,3-dioxoisoindolin-4-ylamino)ethoxy)ethoxy) propanoate (40)

Diisopropylethylamine (10 mL) was added to a solution of 2-(2,6-dioxopiperidin-3-yl)-4-fluoroisoindoline-1,3-dione (31) (1.2 g, 4.3 mmol) and NH$_2$—PEG2-tBu (1 g, 4.3 mmol) in DMF (10 mL). The solution was heated at 90° C. for 2 hours, then cooled, diluted with water (50 mL) and acidified to pH 4-5 with 10% KHSO$_4$. The mixture was extracted with ethyl acetate (3×50 mL) and the combined organic extracts washed with brine, dried over anhydrous sodium sulfate and concentrated. The residue was purified by silica chromatography (petroleum ether/ethyl acetate=2:1) to give the title compound (470 mg, 22% yield) as a yellow solid. $^1$H NMR (400 MHz, CDCl$_3$): δ 8.09 (s, 1H), 7.49 (m, 1H), 7.10 (d, 1H), 6.92 (d, 1H), 4.92 (m, 1H), 3.72 (m, 4H), 3.64 (m, 4H), 3.46 (t, 2H), 2.67-2.94 (m, 3H), 2.51 (t, 2H), 2.13 (m, 1H), 1.44 (s, 9H); MS m/z 512.17 (M+Na)$^+$.

3-(2-(2-((2-(2,6-Dioxopiperidin-3-yl)-1,3-dioxoisoindolin-4-yl)amino)ethoxy)ethoxy) propanoic acid (41)

TFA (6 mL) was added to a solution of tert-butyl 3-(2-(2-(2-(2,6-dioxopiperidin-3-yl)-1,3-dioxoisoindolin-4-ylamino)ethoxy)ethoxy)propanoate (740 mg, 1.51 mmol) in DCM (20 mL), and the solution was stirred for 2 hours. The solvent was removed to give the title compound (615 mg, 94% yield) as a yellow solid. $^1$H NMR (400 MHz, CDCl$_3$): δ 8.62 (s, 1H), 7.48 (m, 1H), 7.10 (d, 1H), 6.91 (d, 1H), 6.54 (br s, 1H), 4.93 (m, 1H), 3.77 (t, 2H), 3.73 (t, 2H), 3.67 (s, 4H), 3.46 (t, 2H), 2.86 (m, 1H), 2.77 (m, 2H), 2.65 (t, 2H), 2.13 (m, 1H); MS m/z 434.25 [M+H]$^+$.

Compound 42 was prepared in an analogous manner to compound 41, employing tert-butyl 1-amino-3,6,9,12,15,18-hexaoxahenicosan-21-oate and (31).

| Compound | Structure/Name | Characterization |
|---|---|---|
| 42 | ![structure] HO-CH$_2$CH$_2$-C(O)-O-CH$_2$CH$_2$-O-CH$_2$CH$_2$-O-CH$_2$CH$_2$-O-CH$_2$CH$_2$-O-CH$_2$CH$_2$-NH-[phthalimide-glutarimide]<br><br>1-((2-(2,6-Dioxopiperidin-3-yl)-1,3-dioxoisoindolin-4-yl)amino)-3,6,9,12,15,18-hexaoxahenicosan-21-oic acid | m/z [M + 1]$^+$: 610.4 |

9-((2-(2,6-Dioxopiperidin-3-yl)-1,3-dioxoisoindolin-4-yl)oxy)nonanoic acid (46)

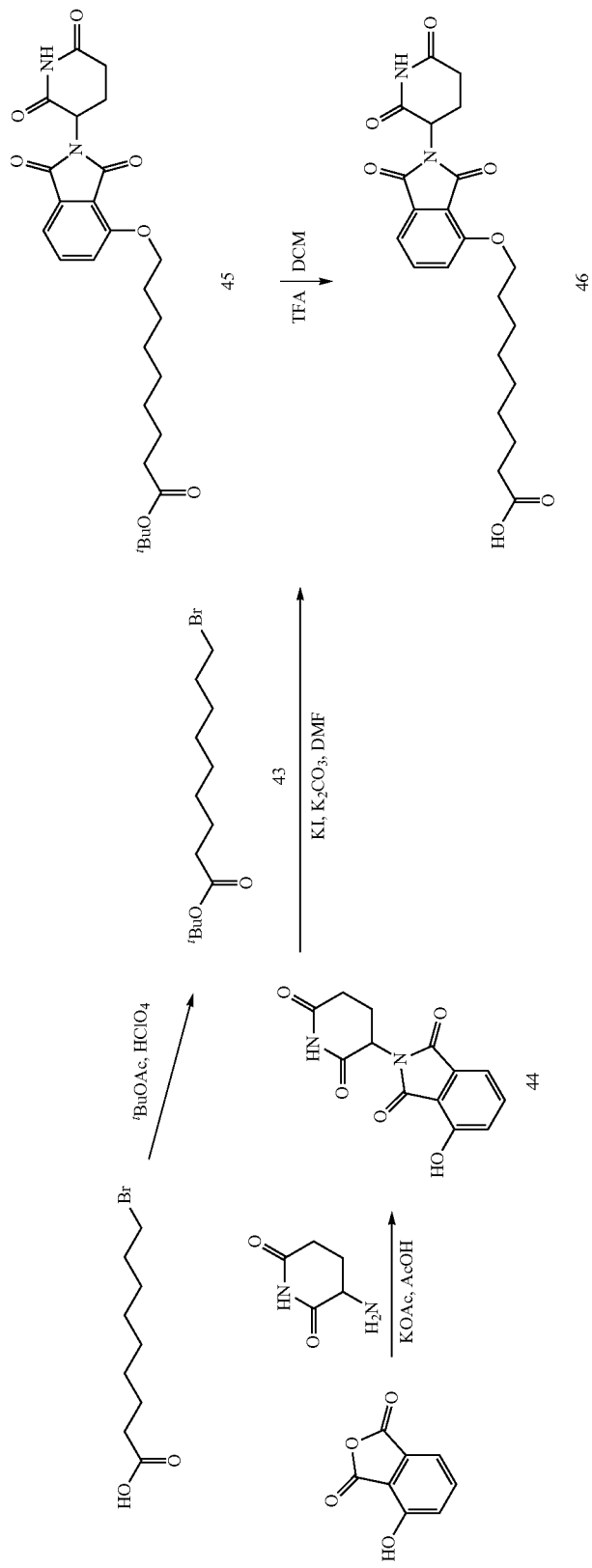

tert-Butyl 9-bromononanoate (43)

9-Bromononanoic acid (5.5 g, 23.2 mmol) was dissolved in tert-butyl acetate (70 mL). HClO$_4$ (1.8 g) was added to the solution and the mixture was stirred overnight then quenched by addition of aq. NaHCO$_3$ (50 mL). The mixture was filtered and the filtrate was extracted with EtOAc (2×50 mL). The combined organic extracts were washed with brine, dried and concentrated. The residue was purified by silica chromatography (petroleum ether/EtOAc: 50/1) to give the title compound (3.6 g, 49% yield) as a colorless oil.

2-(2,6-Dioxopiperidin-3-yl)-4-hydroxyisoindoline-1,3-dione (44)

4-Hydroxyisobenzofuran-1,3-dione (3.6 g, 22 mmol), 3-aminopiperidine-2,6-dione (3.6 g, 22 mmol) and KOAc (8.6 g, 88 mmol) were dissolved in acetic acid (70 mL). The reaction mixture was stirred at 120° C. for 1 hour then cooled and diluted with water (100 mL). The resulting mixture was extracted with EtOAc (2×100 mL). The combined organic extracts were washed with NaHCO$_3$ and brine, dried (Na$_2$SO$_4$) and filtered. The solvents were removed and the solid dried under vacuum to give the title compound (4.0 g, 67% yield) as a blue solid. $^1$H NMR (400 MHz, DMSO): δ 11.30 (br s, 1H), 11.10 (s, 1H), 7.65 (dd, 1H), 7.30 (d, 1H), 7.24 (d, 1H), 5.07 (m, 1H), 2.87 (m, 1H), 2.53 (m, 2H), 2.02 (m, 1H).

9-((2-(2,6-Dioxopiperidin-3-yl)-1,3-dioxoisoindolin-4-yl)oxy)nonanoic acid (46)

A mixture of tert-butyl 9-bromononanoate (2.5 g, 8.53 mmol), 2-(2,6-dioxopiperidin-3-yl)-4-hydroxyisoindoline-1,3-dione (2.34 g, 8.53 mmol), K$_2$CO$_3$ (2.35 g, 17.06 mmol) and KI (0.71 g, 4.27 mmol) in DMF (100 mL) was stirred for 24 hours then diluted with water (200 mL). The resulting mixture was extracted with EtOAc (3×100 mL). The combined organic extracts were washed with NaHCO$_3$ and brine, dried (Na$_2$SO$_4$) and the residue was purified by prep-HPLC to give compound 45 (0.73 g) as a white solid. This material was dissolved in a mixture of DCM (70 mL) and TFA (7 mL). The mixture was stirred for 5 hours then diluted with water (200 mL). The mixture was separated and the aqueous phase was extracted with DCM (2×100 mL). The combined organic extracts were washed with brine, dried and concentrated to give the title compound (0.64 g, 17% yield over two steps) as a white solid. $^1$H NMR (400 MHz, DMSO): δ 12.00 (br s, 1H), 11.1 (s, 1H), 7.79 (dd, 1H), 7.51 (d, 1H), 7.44 (d, 1H), 5.08 (m, 1H), 4.20 (t, 2H), 2.87 (m, 1H), 2.55 (m, 2H), 2.19 (t, 2H), 2.02 (m, 1H), 1.77 (m, 2H), 1.45 (m, 4H), 1.29 (m, 6H); MS m/z 429.3 [M−H]$^-$.

(S)-3-(2-(2-(2-(4-(4-(((2-(2,6-Dioxopiperidin-3-yl)-1-oxoisoindolin-4-yl)oxy) methyl) benzyl) piperazin-1-yl)ethoxy)ethoxy)ethoxy)propanoic acid (55)

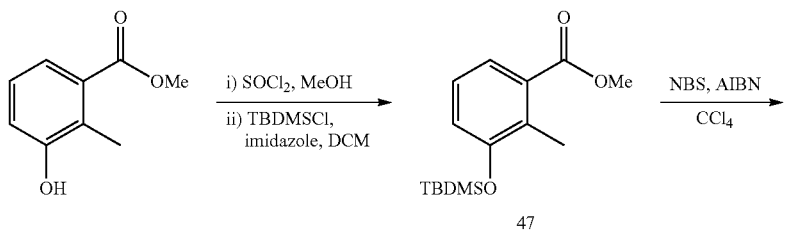

47

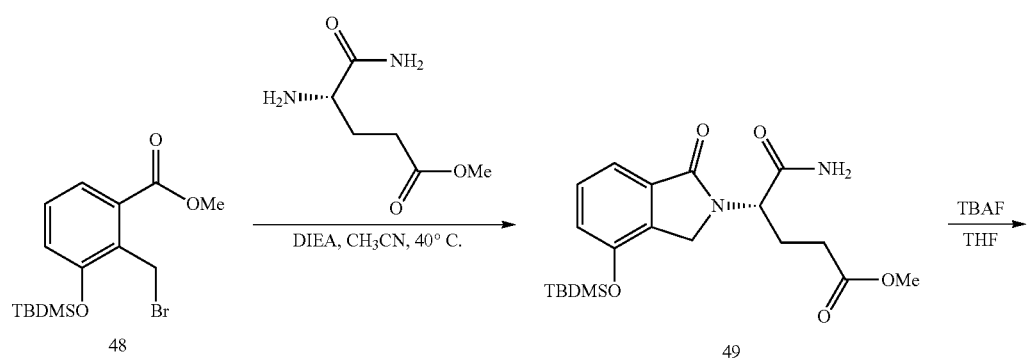

48 49

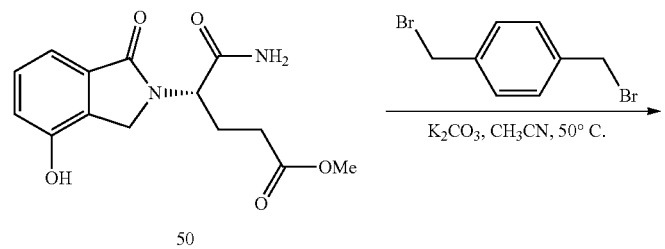

50

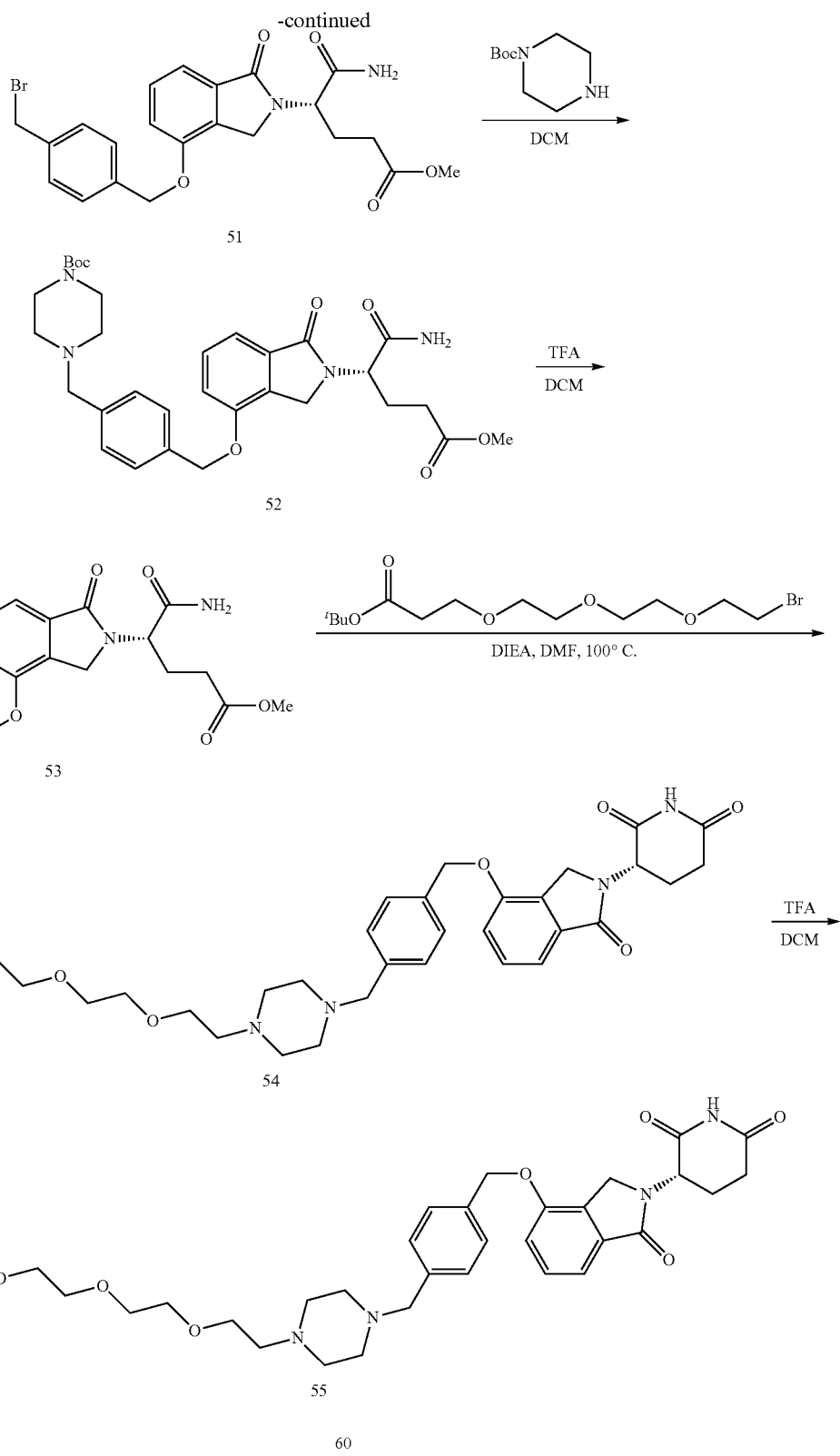

Methyl 2-(bromomethyl)-3-(tert-butyldimethylsilyloxy)benzoate (48)

Thionyl chloride (26.2 g, 0.22 mol) was added dropwise to a solution of 3-hydroxy-2-methylbenzoic acid (20 g, 0.13 mol) in methanol (60 mL) at 0° C. The reaction was refluxed for 1 hour, and the solvent removed to give methyl ester (22.3 g, quantitative yield). The ester (22.3 mol, 0.13 mol) was dissolved in DCM (100 mL) and cooled to 0° C. Imidazole (26.5 g, 0.39 mol) and TBDMSCl (24.2 g, 0.16 mol) were added while keeping the internal temperature between 0-5° C., and the reaction was stirred for 1 hour at 0° C. The mixture was poured into water (100 mL) and extracted with dichloromethane (3×100 mL). The combined organic extracts were washed with brine, dried over anhydrous sodium sulfate, and concentrated. The residue was purified by silica chromatography (petroleum ether/ethyl acetate=100:1) to give TBS-protected methyl ester (47) (37.9 g, quantitative yield). A mixture of TBS-protected methyl ester (37.9 g, 0.13 mol) and NBS (26.7 g, 0.15 mol) in $CCl_4$ (200 mL) was degassed and purged with $N_2$. AIBN (2.3 g, 14 mmol) was added and the reaction was refluxed overnight. After cooling, the precipitate was filtered and washed with $CCl_4$ (50 mL). The filtrate was concentrated, and the residue suspended in water (200 mL) and extracted with EtOAc (3×200 mL). The combined organic extracts were washed with brine, dried over anhydrous sodium sulfate, and concentrated to give the title compound (52 g, quantitative yield), which was used without further purification. $^1$H NMR (400 MHz, $CDCl_3$): δ 7.51 (dd, 1H), 7.23 (m, 1H), 7.00 (dd, 1H), 5.02 (s, 2H), 3.93 (s, 3H), 1.26 (s, 9H), 0.31 (s, 6H).

(S)-Methyl 5-amino-4-(4-(tert-butyldimethylsilyloxy)-1-oxoisoindolin-2-yl)-5-oxopentanoate (49)

A mixture of methyl 2-(bromomethyl)-3-(tert-butyldimethylsilyloxy)benzoate (7.29 g, 20.3 mmol), (S)-methyl 4,5-diamino-5-oxopentanoate hydrochloride (4 g, 20.3 mmol), and DIEA (5.24 g, 40.6 mmol) in acetonitrile (50 mL) was heated at 40° C. overnight. The mixture was cooled, diluted with EtOAc (200 mL), washed with 1 N HCl, sat. sodium bicarbonate and brine, dried over anhydrous sodium sulfate, and concentrated. The residue was purified by silica chromatography (DCM/methanol=100:1) to give the title compound (4.2 g, 51% yield) as a light yellow powder. $^1$H NMR (400 MHz, $CDCl_3$): δ 7.44 (d, 1H), 7.34 (m, 1H), 6.96 (d, 1H), 6.38 (br s, 1H), 5.37 (br s, 1H), 4.90 (m, 1H), 4.35 (dd, 2H), 3.65 (s, 3H), 2.44 (m, 3H), 2.35 (m, 1H), 1.00 (s, 9H), 0.26 (s, 6H).

(S)-Methyl 5-amino-4-(4-hydroxy-1-oxoisoindolin-2-yl)-5-oxopentanoate (50)

TBAF (6.3 g, 20.0 mmol) was added to a solution of (S)-methyl 5-amino-4-(4-(tert-butyldimethylsilyloxy)-1-oxoisoindolin-2-yl)-5-oxopentanoate (4.2 g, 10.0 mmol) in THF (20 mL) and the reaction mixture was stirred for 2 hours. The solution was poured into water (50 mL) and extracted with EtOAc (3×50 mL). The combined organic extracts were washed with brine, dried over anhydrous sodium sulfate, and concentrated to give the title compound (3.6 g, quantitative yield), which was used without further purification.

(S)-Methyl 5-amino-4-(4-(4-(bromomethyl)benzyloxy)-1-oxoisoindolin-2-yl)-5-oxo pentanoate (51)

A mixture of (S)-methyl 5-amino-4-(4-hydroxy-1-oxoisoindolin-2-yl)-5-oxopentanoate (3.6 g, 12.3 mmol), 1,4-bis(bromomethyl)benzene (9.7 g, 36.9 mmol), and potassium carbonate (1.7 g, 12.3 mmol) in acetonitrile (20 mL) was heated at 50° C. overnight. The mixture was cooled, filtered, and washed with acetonitrile (10 mL). The filtrate was concentrated and the residue purified by silica chromatography (DCM/methanol=100:1) to give the title compound (1.28 g, 22% yield). MS m/z 475.34 [M+H]$^+$ (S)-tert-Butyl 4-(4-((2-(1-amino-5-methoxy-1,5-dioxopentan-2-yl)-1-oxoisoindolin-4-yloxy)methyl)benzyl)piperazine-1-carboxylate (52)

tert-Butyl piperazine-1-carboxylate (1.69 g, 9.1 mmol) was added to a solution of (S)-methyl 5-amino-4-(4-(4-(bromomethyl)benzyloxy)-1-oxoisoindolin-2-yl)-5-oxopentanoate (1.23 g, 2.6 mmol) in DCM (10 mL). The reaction was stirred for 5 hours. The solvent was removed and the residue was purified by silica chromatography (DCM/methanol=20:1) to give the title compound (1.1 g, 73% yield).

(S)-Methyl 5-amino-5-oxo-4-(1-oxo-4-(4-(piperazin-1-ylmethyl)benzyloxy) isoindolin-2-yl) pentanoate (53)

TFA (3 mL) was added to a solution of (S)-tert-Butyl 4-(4-((2-(1-amino-5-methoxy-1,5-dioxopentan-2-yl)-1-oxoisoindolin-4-yloxy)methyl)benzyl)piperazine-1-carboxylate (1.1 g, 1.9 mmol) in DCM (6 mL). The reaction was stirred for 2 hours. The solvent was removed to give the title compound as the TFA salt (1.1 g, 86% yield).

(S)-tert-Butyl 3-(2-(2-(2-(4-(4-((2-(2,6-dioxopiperidin-3-yl)-1-oxoisoindolin-4-yloxy)methyl) benzyl) piperazin-1-yl)ethoxy)ethoxy)ethoxy)propanoate (54)

A solution of (S)-methyl 5-amino-5-oxo-4-(1-oxo-4-(4-(piperazin-1-ylmethyl) benzyloxy)isoindolin-2-yl)pentanoate (173 mg, 0.26 mmol), tert-butyl 3-(2-(2-(2-bromoethoxy)ethoxy)ethoxy)propanoate (122 mg, 0.34 mmol), and DIEA (139 mg, 1.08 mmol) in DMF (5 mL) was heated at 100° C. overnight. The mixture was cooled, poured into water (30 mL), and extracted with EtOAc (3×30 mL). The combined organic extracts were washed with brine, dried over anhydrous sodium sulfate, and concentrated. The residue was purified by silica chromatography (DCM/methanol=20:1) to give the title compound (130 mg, 67% yield). MS m/z 709.52 [M+H]$^+$ (S)-3-(2-(2-(2-(4-(4-(((2-(2,6-Dioxopiperidin-3-yl)-1-oxoisoindolin-4-yl)oxy)methyl)benzyl) piperazin-1-yl)ethoxy)ethoxy)ethoxy)propanoic acid (55)

TFA (5 mL) was added to a solution of (S)-tert-butyl 3-(2-(2-(2-(4-(4-((2-(2,6-dioxopiperidin-3-yl)-1-oxoisoindolin-4-yloxy)methyl)benzyl)piperazin-1-yl)ethoxy)ethoxy)ethoxy)propanoate (130 mg, 0.18 mmol) in DCM (5 mL). The reaction was stirred for 2 hours and the solvent was removed to give the title compound (160 mg, ~quantitative yield). MS m/z 653.6 [M+H]$^+$ tert-Butyl ((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)carbamate (56) was prepared according to the synthetic procedures described in Galdeano, C. et. al. *J. Med. Chem.* 2014, 57, 8657, the contents of which are incorporated herein by reference.

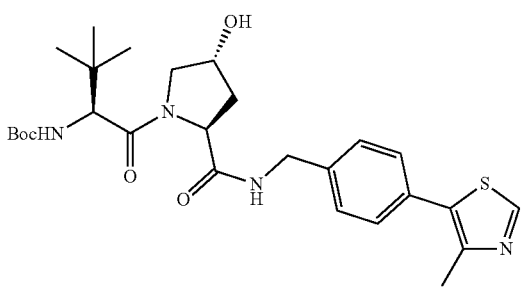

Preparation of Example Compounds

Example 1. N—((S)-1-(2-Chloro-6-(3-(5-chloro-6-(2H-1,2,3-triazol-2-yl)pyridin-3-yl)ureido)pyrazolo[1,5-a]pyrimidin-7-yl)ethyl)-1-((2-(2,6-dioxopiperidin-3-yl)-1,3-dioxoisoindolin-4-yl)amino)-N-methyl-3,6,9,12-tetraoxapentadecan-15-amide

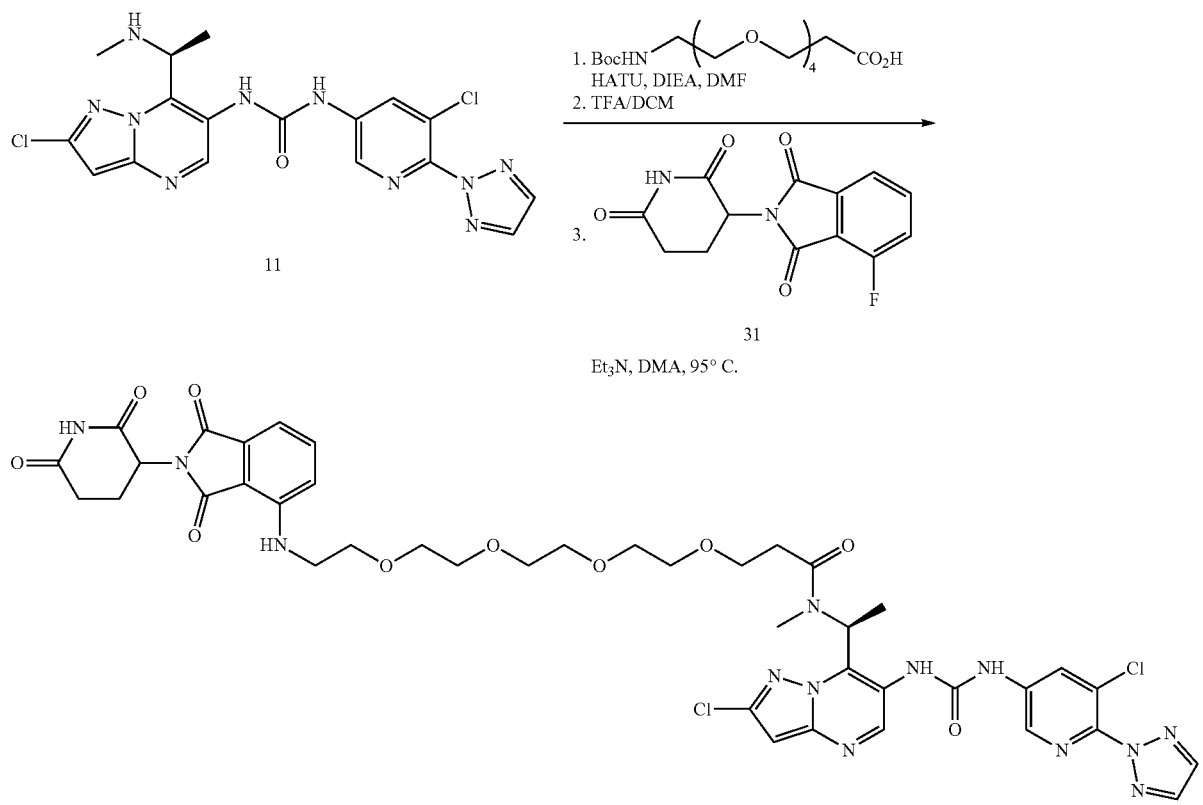

Example 1 tert-Butyl (S)-(17-(2-chloro-6-(3-(5-chloro-6-(2H-1,2,3-triazol-2-yl)pyridin-3-yl)ureido)pyrazolo[1,5-a]pyrimidin-7-yl)-16-methyl-15-oxo-3,6,9,12-tetraoxa-16-azaoctadecyl)carbamate HATU (20 mg, 0.045 mmol), 2,2-dimethyl-4-oxo-3,8,11,14,17-pentaoxa-5-azaicosan-20-oic acid (10 mg, 0.026 mmol) and DIEA (20 µL, 0.11 mmol) were added to a solution of (S)-1-(5-chloro-6-(2H-1,2,3-triazol-2-yl)pyridin-3-yl)-3-(2-chloro-7-(1-(methylamino)ethyl)pyrazolo[1,5-a]pyrimidin-6-yl)urea hydrochloride (10 mg, 0.021 mmol) in DMF (3 mL). The reaction was stirred for 30 minutes and the mixture was purified by HPLC to give the title compound (10 mg, 56%) as an oil. MS m/z 795.57 [M+H]$^+$.

N—((S)-1-(2-Chloro-6-(3-(5-chloro-6-(2H-1,2,3-triazol-2-yl)pyridin-3-yl)ureido)pyrazolo[1,5-a]pyrimidin-7-yl)ethyl)-1-((2-(2,6-dioxopiperidin-3-yl)-1,3-dioxoisoindolin-4-yl)amino)-N-methyl-3,6,9,12-tetraoxapentadecan-15-amide (Example 1)

tert-Butyl (S)-(17-(2-chloro-6-(3-(5-chloro-6-(2H-1,2,3-triazol-2-yl)pyridin-3-yl)ureido)pyrazolo[1,5-a]pyrimidin-7-yl)-16-methyl-15-oxo-3,6,9,12-tetraoxa-16-azaoctadecyl)carbamate (10 mg, 0.013 mmol) was dissolved in DCM (10 mL). TFA (1 mL) was added and the mixture was stirred for 30 minutes. The solvent was removed under reduced pressure and the residue was dissolved in DMA (3 mL). 2-(2,6-Dioxopiperidin-3-yl)-4-fluoroisoindoline-1,3-dione (6 mg, 0.019 mmol) and triethylamine (18 µL, 0.125 mmol) were added and the mixture stirred at 90° C. for 24 hours. The mixture was purified by HPLC to give the title compound (3 mg, 25%) as a yellow oil. MS m/z 950.48 [M+H]$^+$.

Examples 2-3 were prepared in an analogous manner to Example 1, employing the indicated amine starting materials and 2,2-dimethyl-4-oxo-3,8,11,14,17-pentaoxa-5-azaicosan-20-oic acid, followed by subsequent reaction with 2-(2,6-dioxopiperidin-3-yl)-4-fluoroisoindoline-1,3-dione (31).

| Example | Structure/Name | Characterization | Starting material |
|---|---|---|---|
| 2 | 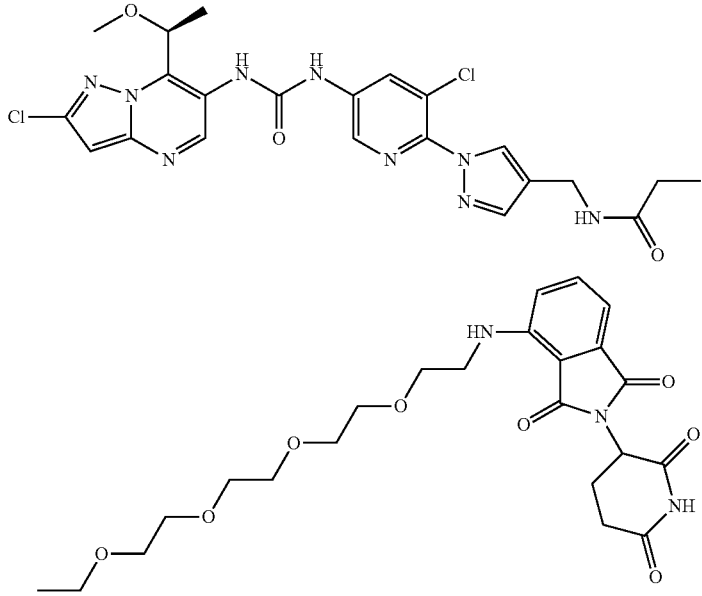<br>N-((1-(3-Chloro-5-(3-(2-chloro-7-((S)-1-methoxyethyl)pyrazolo[1,5-a]pyrimidin-6-yl)ureido)pyridin-2-yl)-1H-pyrazol-4-yl)methyl)-1-((2-(2,6-dioxopiperidin-3-yl)-1,3-dioxoisoindolin-4-yl)amino)-3,6,9,12-tetraoxapentadecan-15-amide | $^1$H NMR (500 MHz, d$_6$-DMSO): 11.09 (s, 1H), 10.14 (s, 1H), 8.95 (s, 1H), 8.53 (s, 1H), 8.47 (d, 1H), 8.37 (d, 1H), 8.26 (t, 1H), 8.02 (s, 1H), 7.65 (s, 1H), 7.57 (dd, 1H), 7.13 (d, 1H), 7.03 (d, 1H), 6.93 (s, 1H), 6.59 (br, 1H), 5.42 (q, 1H), 5.05 (dd, 1H), 4.20 (d, 2H), 3.62 (m, 4H), 4.50 (m, 14H), 3.47 (s, 3H), 2.85 (m, 1H), 2.60 (m, 1H), 2.49 (m, 1H), 2.36 (t, 2H), 2.03 (m, 1H), 1.58 (d, 3H); m/z [M + 1]$^+$: 979.59 | (26) |
| 3 | 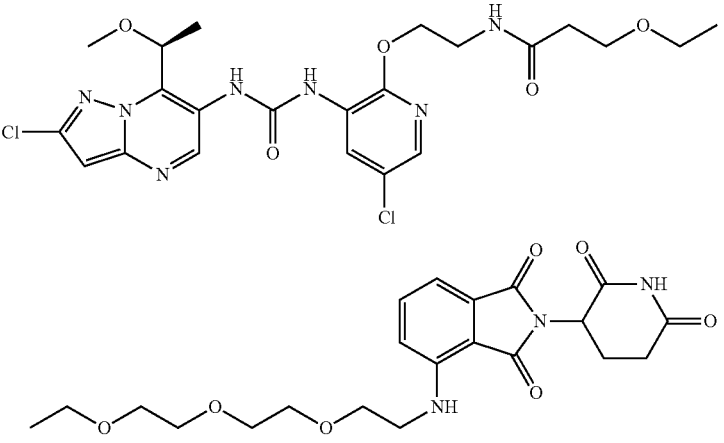<br>N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-1-((2-(2,6-dioxopiperidin-3-yl)-1,3-dioxoisoindolin-4-yl)amino)-3,6,9,12-tetraoxapentadecan-15-amide | 11.09(s, 1H), 9.09 (s, 11.09 (s, 1H), 9.09 (s, 1H), 8.88 (s, 1H), 8.75 (s, 1H), 8.45 (d, 1H), 8.08 (t, 1H), 7.80 (d, 1H), 7.57 (dd, 1H), 7.13 (d, 1H), 7.04 (d, 1H), 6.93 (s, 1H), 6.59 (t, 1H), 5.37 (q, 1H), 5.05 (dd, 1H), 4.41 (t, 2H), 3.60 (m, 4H), 3.40-3.58 (m, 19H), 2.86 (m, 1H), 2.58 (m, 1H), 2.49 (m, 1H), 2.35 (t, 2H), 2.04 (m, 1H), 1.59 (d, 3H); m/z [M + 1]$^+$: 943.62 | (28) |

Example 4. N—((S)-1-(2-Chloro-6-(3-(5-chloro-6-(2H-1,2,3-triazol-2-yl)pyridin-3-yl)ureido)pyrazolo[1,5-a]pyrimidin-7-yl)ethyl)-3-(2-(2-((2-(2,6-dioxopiperidin-3-yl)-1-oxoisoindolin-4-yl)amino)ethoxy)ethoxy)-N-methylpropanamide

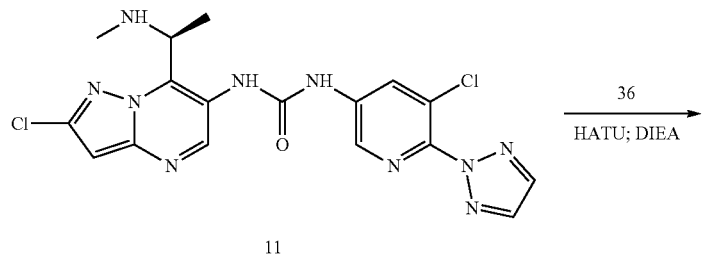

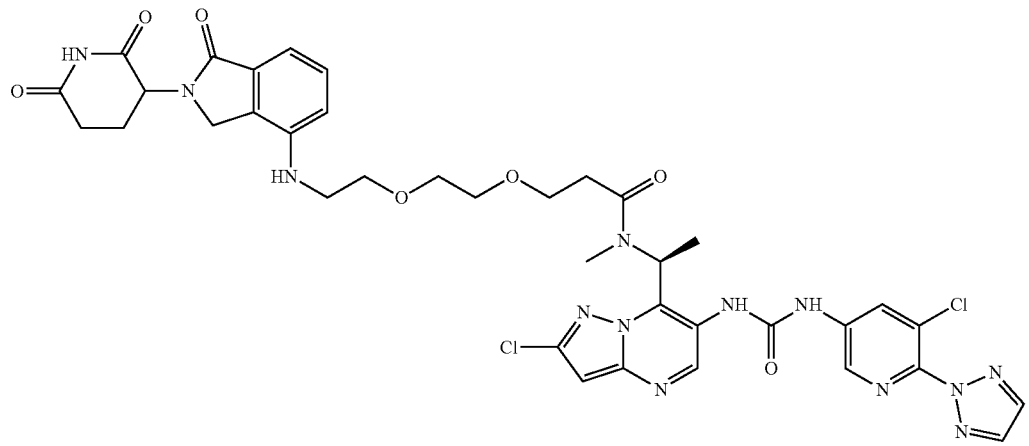

Example 4

N—((S)-1-(2-Chloro-6-(3-(5-chloro-6-(2H-1,2,3-triazol-2-yl)pyridin-3-yl)ureido)pyrazolo[1,5-a]pyrimidin-7-yl)ethyl)-3-(2-(2-((2-(2,6-dioxopiperidin-3-yl)-1-oxoisoindolin-4-yl)amino)ethoxy)ethoxy)-N-methylpropanamide (Example 4)

(S)-1-(5-Chloro-6-(2H-1,2,3-triazol-2-yl)pyridin-3-yl)-3-(2-chloro-7-(1-(methylamino)ethyl)pyrazolo[1,5-a]pyrimidin-6-yl)urea hydrochloride (10 mg, 0.021 mmol) was dissolved in DMF (1.5 mL) along with 3-(2-(2-((2-(2,6-dioxopiperidin-3-yl)-1-oxoisoindolin-4-yl)amino)ethoxy)ethoxy)propanoic acid (10 mg, 0.023 mmol) and HATU (17 mg, 0.042 mmol). DIEA (20 μL, 0.103 mmol) was added and the mixture stirred for 30 minutes. The mixture was purified by reversed-phase HPLC to give the title compound (8 mg, 42%) as a brown oil. $^1$H NMR (500 MHz DMSO) δ 11.00 (s, 1H), 10.19 (br, 1H), 8.63 (s, 2H), 8.57 (d, 1H), 8.46 (d, 1H), 8.14 (s, 2H), 7.26 (m, 1H), 6.94 (m, 2H), 6.78 (d, 1H), 5.69 (m, 1H), 5.10 (dd, 1H), 4.22 (d, 1H), 4.11 (d, 1H), 3.54 (m, 4H), 3.42 (m, 4H), 3.27 (t, 2H), 3.25 (s, 3H), 2.92 (m, 1H), 2.60 (m, 3H), 2.31 (m, 1H), 2.01 (m, 1H), 1.67 (d, 3H). MS m/z 848.66 [M+H]$^+$.

Examples 5-8 were prepared in an analogous manner to Example 4, employing the indicated amine starting materials and 3-(2-(2-((2-(2,6-dioxopiperidin-3-yl)-1-oxoisoindolin-4-yl)amino)ethoxy)ethoxy)propanoic acid (36).

| Example | Structure/Name | MS | Starting material |
|---|---|---|---|
| 5 | 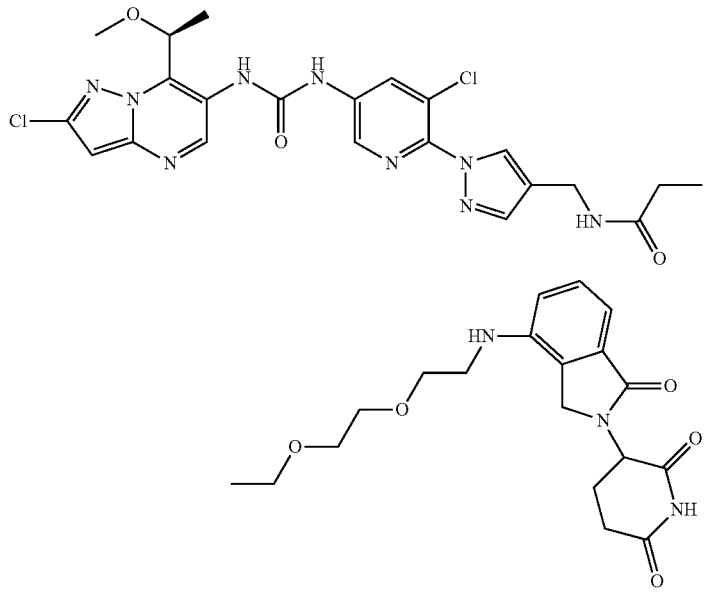 N-((1-(3-Chloro-5-(3-(2-chloro-7-((S)-1-methoxyethyl)pyrazolo[1,5-a]pyrimidin-6-yl)ureido)pyridin-2-yl)-1H-pyrazol-4-yl)methyl)-3-(2-(2-((2-(2,6-dioxopiperidin-3-yl)-1-oxoisoindolin-4-yl)amino)ethoxy)ethoxy)propanamide | m/z [M + 1]$^+$: 877.77 | (26) |
| 6 | 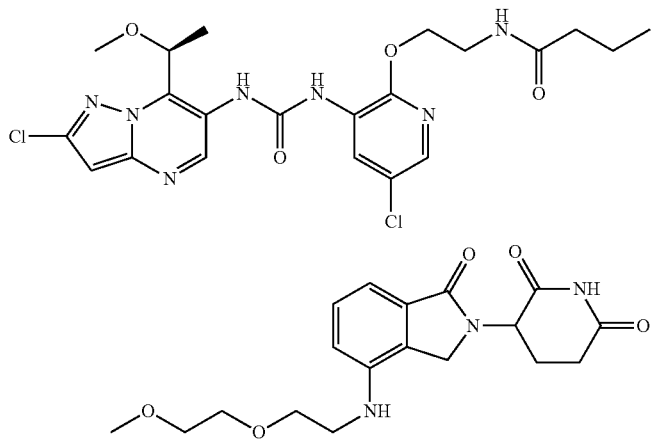 N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-3-(2-(2-((2-(2,6-dioxopiperidin-3-yl)-1-oxoisoindolin-4-yl)amino)ethoxy)ethoxy)propanamide | m/z [M + 1]$^+$: 841.25 | (28) |

| Example | Structure/Name | MS | Starting material |
|---|---|---|---|
| 7 | 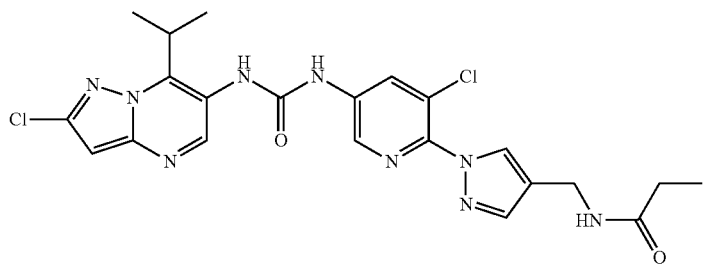<br>N-((1-(3-Chloro-5-(3-(2-chloro-7-isopropylpyrazolo[1,5-a]pyrimidin-6-yl)ureido)pyridin-2-yl)-1H-pyrazol-4-yl)methyl)-3-(2-(2-((2-(2,6-dioxopiperidin-3-yl)-1-oxoisoindolin-4-yl)amino)ethoxy)ethoxy)propanamide | m/z [M + 1]⁺: 861.68 | (29) |
| 8 | 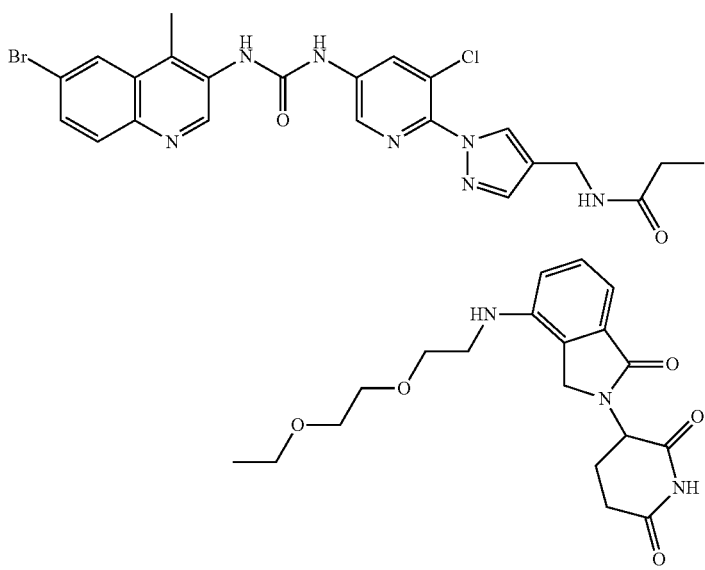<br>N-((1-(5-(3-(6-Bromo-4-methylquinolin-3-yl)ureido)-3-chloropyridin-2-yl)-1H-pyrazol-4-yl)methyl)-3-(2-(2-((2-(2,6-dioxopiperidin-3-yl)-1-oxoisoindolin-4-yl)amino)ethoxy)ethoxy)propanamide | m/z [M + 1]⁺: 841.25 | (30) |

Example 9. $N^1$-(2-((5-Chloro-3-(3-(2-chloro-7-((S)-1-methoxyethyl)pyrazolo[1,5-a]pyrimidin-6-yl)ureido)pyridin-2-yl)oxy)ethyl)-$N^{16}$-((2S)-1-((4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide

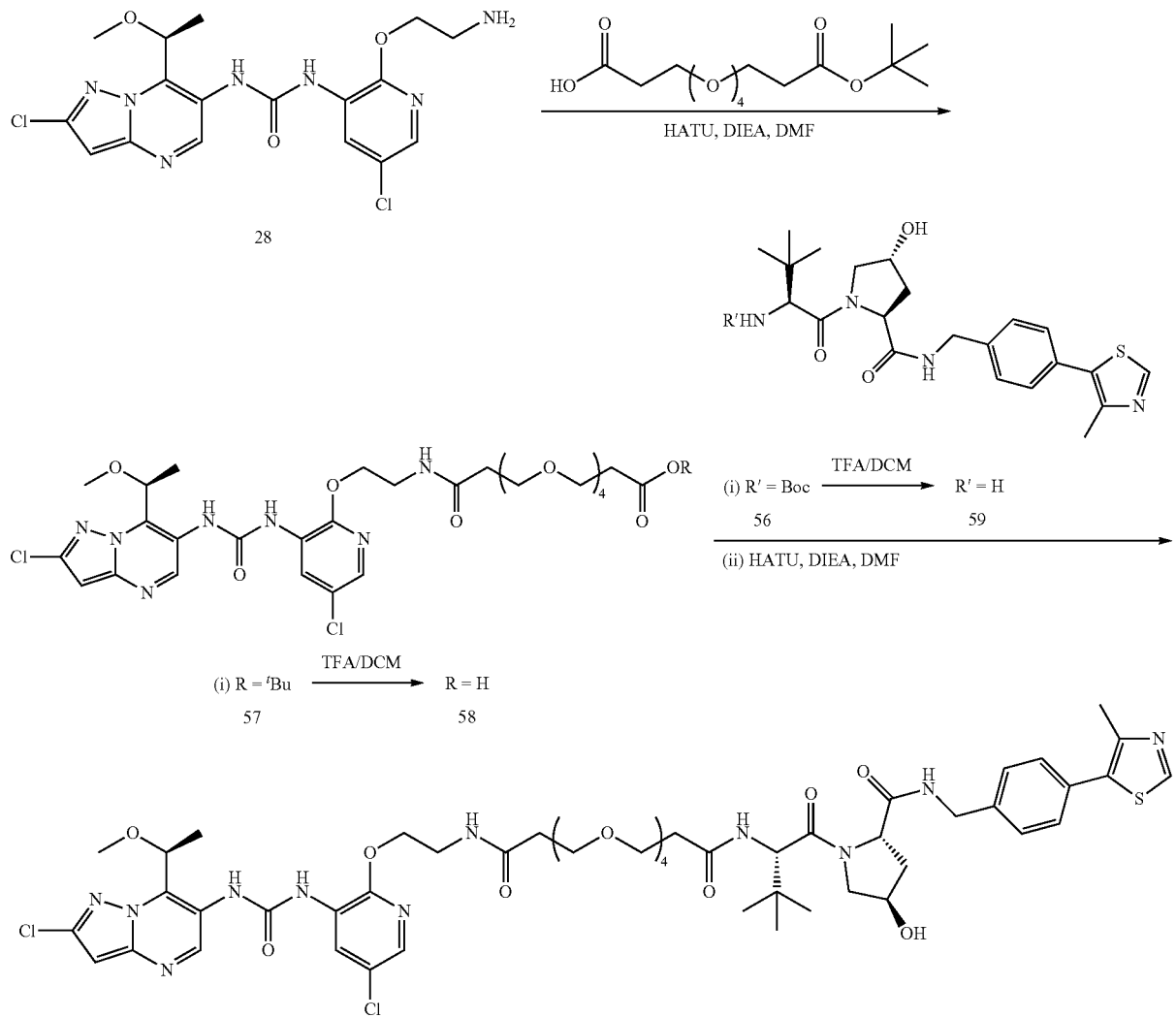

Example 9 tert-Butyl (S)-1-((5-chloro-3-(3-(2-chloro-7-(1-methoxyethyl)pyrazolo[1,5-a]pyrimidin-6-yl)ureido)pyridin-2-yl)oxy)-4-oxo-7,10,13,16-tetraoxa-3-azanonadecan-19-oate (57)

HATU (35 mg, 0.091 mmol), tert-butyl 1-hydroxy-1-oxo-2,5,8,11-tetraoxatetradecan-14-oate (28) (19 mg, 0.055 mmol) and DIEA (40 μL, 0.227 mmol) were added to a solution of (S)-1-(2-(2-aminoethoxy)-5-chloropyridin-3-yl)-3-(2-chloro-7-(1-methoxyethyl)pyrazolo[1,5-a]pyrimidin-6-yl)urea hydrochloride (20 mg, 0.045 mmol) in DMF (5 mL). After stirring for 30 minutes, the mixture was purified by HPLC to give the title compound (25 mg, 71% yield) as a colorless oil. MS m/z 772.60 [M+H]$^+$.

$N^1$-(2-((5-Chloro-3-(3-(2-chloro-7-((S)-1-methoxyethyl)pyrazolo[1,5-a]pyrimidin-6-yl)ureido)pyridin-2-yl)oxy)ethyl)-$N^{16}$-((2S)-1-((4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide (Example 9)

tert-Butyl (S)-1-((5-chloro-3-(3-(2-chloro-7-(1-methoxyethyl)pyrazolo[11,5-a]pyrimidin-6-yl)ureido)pyridin-2-yl)oxy)-4-oxo-7,10,13,16-tetraoxa-3-azanonadecan-19-oate (57) (25 mg, 0.032 mmol) was dissolved in DCM (10 mL). TFA (1 mL) was added and the mixture stirred for 30 minutes and then concentrated under reduced pressure. In a separate flask, tert-butyl ((2S)-1-((4R)-4-hydroxy-2-((4-(4-methylthiazol-5-yl)benzyl)carbamoyl)pyrrolidin-1-yl)-3,3-dimethyl-1-oxobutan-2-yl)carbamate (56) (18 mg, 0.033 mmol) was dissolved in DCM (10 mL) and TFA (1 mL) and stirred for 30 minutes, then concentrated under reduced pressure. This material was dissolved in DMF (5 mL) and added to the other flask along with HATU (25 mg, 0.065 mmol) and DIEA (56 µL, 0.320 mmol). After stirring for 30 minutes, the mixture was purified by HPLC to give the title compound (24 mg, 65% yield) as a colorless oil. MS m/z 1130.74 [M+H]+.

Example 10 was prepared in an analogous manner to Example 9, employing the indicated amine starting material and tert-butyl 1-hydroxy-1-oxo-2,5,8,11-tetraoxatetradecan-14-oate, followed by coupling with compound (59) after removal of the Boc group of tert-butyl ((2S)-1-((4R)-4-hydroxy-2-((4-(4-methylthiazol-5-yl)benzyl)carbamoyl)pyrrolidin-1-yl)-3,3-dimethyl-1-oxobutan-2-yl)carbamate (56).

| Example | Structure/Name | MS | Starting material |
|---|---|---|---|
| 10 | | m/z [M + 1]+: 1166.78 | (26) |

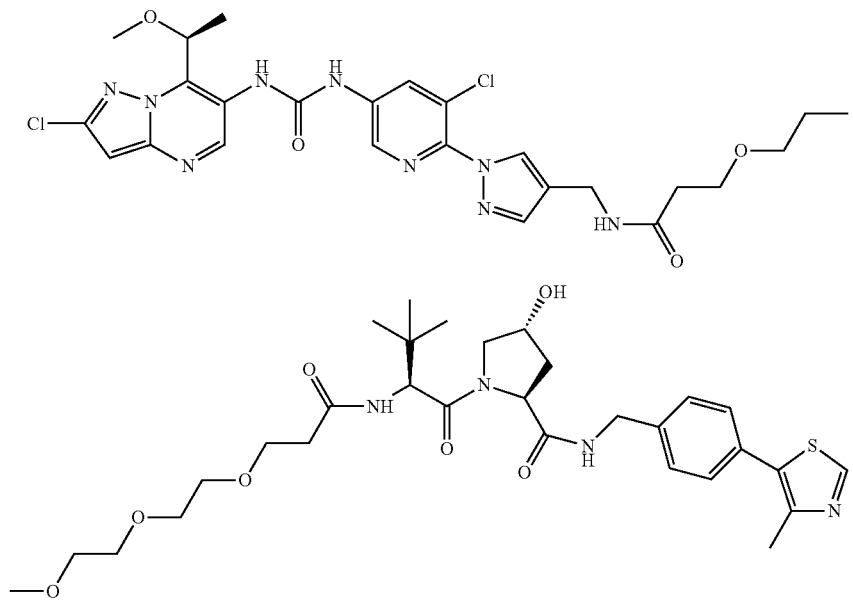

N1-((1-(3-Chloro-5-(3-(2-chloro-7-(S)-1-methoxyethyl)pyrazolo[1,5-a]pyrimidin-6-yl)ureido)pyridin-2-yl)-1H-pyrazol-4-yl)methyl)-N16-((2S)-1-((4R)-4-hydroxy-2-((4-(4-methylthiazol-5-yl)benzyl)carbamoyl)pyrrolidin-1-yl)-3,3-dimethyl-1-oxobutan-2-yl)-4,7,10,13-tetraoxahexadecanediamide Examples 11-19 were prepared in an analogous manner to Example 4, employing the indicated amine and acid starting materials.

| Example | Structure/Name | MS | Starting material |
|---|---|---|---|
| 11 | 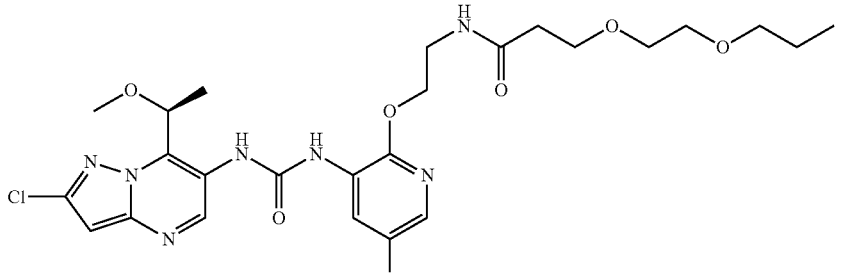<br>N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-1-((2-(2,6-dioxopiperidin-3-yl)-1-oxoisoindolin-4-yl)amino)-3,6,9,12-tetraoxapentadecan-15-amide | m/z [M + 1]$^+$: 929.40 | (28) + (37) |
| 12 | 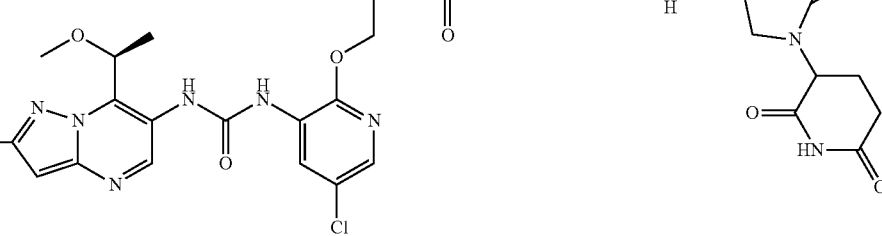<br>N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-3-(2-((2-(2,6-dioxopiperidin-3-yl)-1-oxoisoindolin-4-yl)amino)ethoxy)piopanamide | m/z [M + 1]$^+$: 797.13 | (28) + (38) |
| 13 | 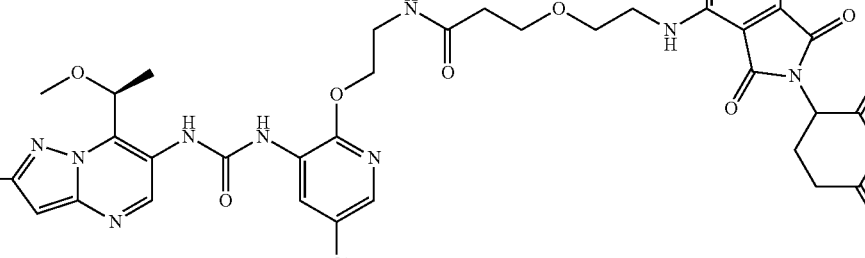<br>N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-3-(2-((2-(2,6-dioxopiperidin-3-yl)-1,3-dioxoisoindolin-4-yl)amino)ethoxy)propanamide | m/z [M + 1]$^+$: 812.59 | (28) + (39) |

| Example | Structure/Name | MS | Starting material |
|---|---|---|---|
| 14 | 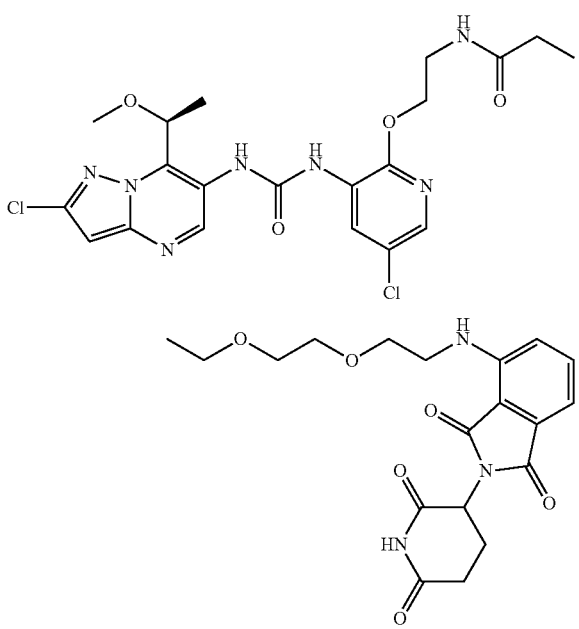<br>N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-3-(2-(2-((2-(2,6-dioxopiperidin-3-yl)-1,3-dioxoisoindolin-4-yl)amino)ethoxy)ethoxy)propanamide | m/z [M + 1]⁺: 855.31 | (28) + (41) |
| 15 | 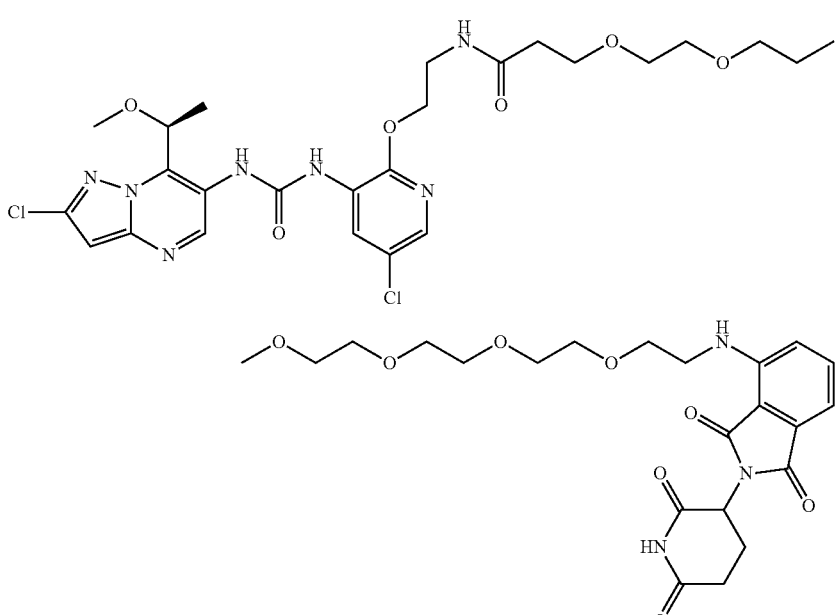<br>N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-1-((2-(2,6-dioxopiperidin-3-yl)-1,3-dioxoisoindolin-4-yl)amino)-3,6,9,12,15,18-hexaoxahenicosan-21-amide | m/z [M + 1]⁺: 1032.67 | (28) + (42) |

| Example | Structure/Name | MS | Starting material |
|---|---|---|---|
| 16 | 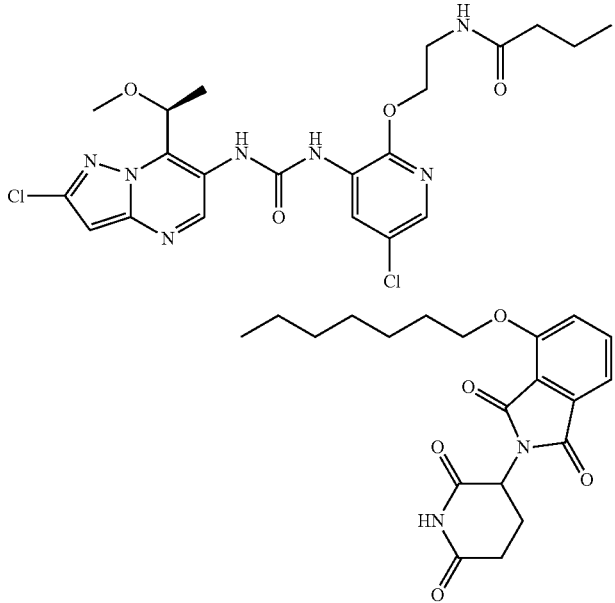<br>N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-9-((2-(2,6-dioxopiperidin-3-yl)-1,3-dioxoisoindolin-4-yl)oxy)nonanamide | m/z [M + 1]⁺: 853.41 | (28) + (46) |
| 17 | 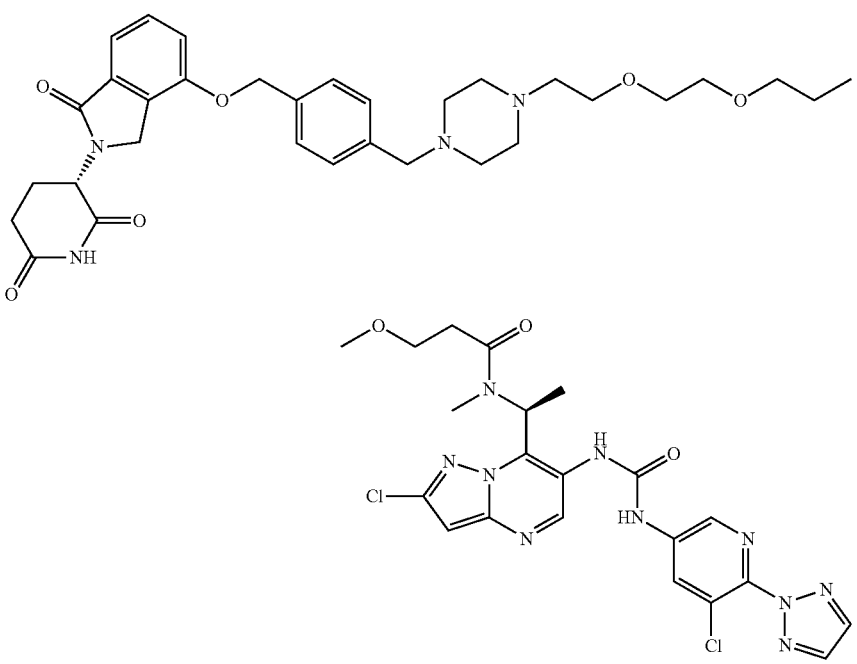<br>N-((S)-1-(2-Chloro-6-(3-(5-chloro-6-(2H-1,2,3-triazol-2-yl)pyridin-3-yl)ureido)pyrazolo[1,5-a]pyrimidin-7-yl)ethyl)-3-(2-(2-(2-(4-(4-(((2-((S)-2,6-dioxopiperidin-3-yl)-1-oxoisoindolin-4-yl)oxy)methyl)benzyl)piperazin-1-yl)ethoxy)ethoxy)ethoxy)-N-methylpropanamide | m/z [M + 1]⁺: 1083.38 | (11) + (55) |

| Example | Structure/Name | MS | Starting material |
|---|---|---|---|
| 18 | N-((1-(3-Chloro-5-(3-(2-chloro-7-((S)-1-methoxyethyl)pyrazolo[1,5-a]pyrimidin-6-yl)ureido)pyridin-2-yl)-1H-pyrazol-4-yl)methyl)-3-(2-(2-(2-(4-(4-(((2-((S)-2,6-dioxopiperidin-3-yl)-1-oxoisoindolin-4-yl)oxy)methyl)benzyl)piperazin-1-yl)ethoxy)ethoxy)ethoxy)propanamide | m/z [M + 1]⁺: 1112.61 | (26) + (55) |
| 19 | N-(2-((5-Chloro-3-(3-(2-chloro-7-((S)-1-methoxyethyl)pyrazolo[1,5-a]pyrimidin-6-yl)ureido)pyridin-2-yl)oxy)ethyl)-3-(2-(2-(2-(4-(4-(((2-((S)-2,6-dioxopiperidin-3-yl)-1-oxoisoindolin-4-yl)oxy)methyl)benzyl)piperazin-1-yl)ethoxy)ethoxy)ethoxy)propanamide | m/z [M + 1]⁺: 1076.61 | (28) + (55) |

MALT1 Degradation Assay

Table 3 provides the results of experimental data obtained from the example compounds of the present disclosure. In particular, OCI-Ly3 cells were grown for 48 hours in the presence of the indicated concentrations of Examples 1-19. Proteins were extracted, analyzed by Western blot, and membranes were immunoblotted for MALT1, CRBN, and Actin. Western blot bands were quantified using Image Lab software. Results were normalized to Actin expression and presented as % MALT1 degradation relative to vehicle treated cells. Table 3 shows that moderate to high levels of MALT1 degradation were achieved.

TABLE 3

| Example | % MALT1 Degradation at 1 μM |
|---|---|
| 1 | 31-50% |
| 2 | >50% |
| 3 | >50% |

TABLE 3-continued

| Example | % MALT1 Degradation at 1 μM |
|---|---|
| 4 | 31-50% |
| 5 | 10-30% |
| 6 | >50% |
| 7 | 31-50% |
| 8 | 31-50% |
| 9 | 10-30% |
| 10 | no degradation |
| 11 | >50% |
| 12 | 31-50% |
| 13 | no degradation |
| 14 | >50% |
| 15 | >50% |
| 16 | no degradation |
| 17 | >50% |
| 18 | >50% |
| 19 | >50% |

Mechanistic Validation of MALT1 Degradation

Mechanistic Validation Using Cereblon (CRBN) Knockout Cells.

Figure 2:
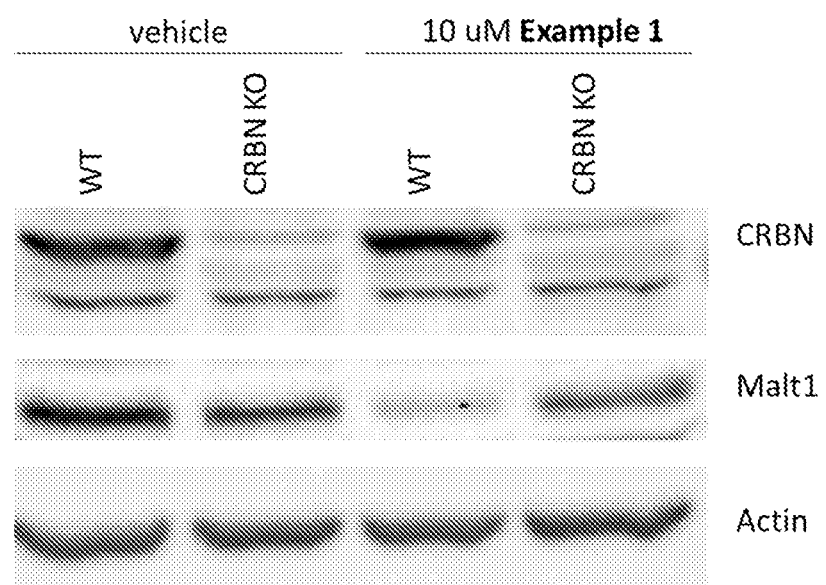
FIG. 2 shows images of Western blots demonstrating that MALT1 degradation is dependent on the presence of CRBN. Wild type and CRBN knockout 293T cells were treated with 10 μM of Example 1 or vehicle for 24 hours, and protein lysates were collected. The protein was analyzed by Western blot and immunoassayed for MALT1, CRBN, and Actin.

Wild type and CRBN knockout 293T cells were treated with 10 μM of Example 1 or vehicle for 24 hours, and protein lysates were collected. 80 μg of protein were analyzed by Western blot and immunoassayed for MALT1, CRBN and Actin. As shown in FIG. 2, Example 1 promoted CRBN-dependent MALT1 degradation.

Taken together, these results suggest that the compounds of the invention induced rapid and efficient MALT1 degradation by actively recruiting E3 ubiquitin ligase Cereblon to MALT1, which directs MALT1 to the proteasome degradation machinery.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula I:

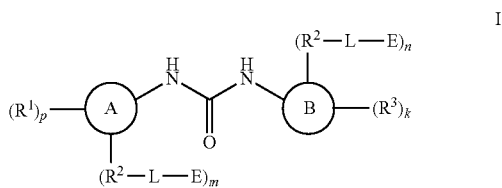

or a pharmaceutically acceptable salt thereof, wherein:
A is a fused bicyclic heteroaryl ring;
B is phenyl or pyridinyl;
each occurrence of $R^1$ and $R^3$ is, independently, hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted heteroalkyl, —$OR^A$, —$N(R^A)_2$, —$SR^A$, —CN, —SCN, —C(=$NR^A$)$R^A$, —C(=$NR^A$)$OR^A$, —C(=$NR^A$)N($R^A$)$_2$, —C(=O)$R^A$, —C(=O)$OR^A$, —C(=O)N($R^A$)$_2$, —$NO_2$, —$NR^A$C(=O)$R^A$, —$NR^A$C(=O)$OR^A$, —$NR^A$C(=O)N($R^A$)$_2$, —OC(=O)$R^A$, —OC(=O)$OR^A$, —OC(=O)N($R^A$)$_2$, or a nitrogen protecting group when attached to a nitrogen atom;
$R^2$ is substituted or unsubstituted alkylene, substituted or unsubstituted heterocyclylene, substituted or unsubstituted arylene, substituted or unsubstituted heteroarylene, substituted or unsubstituted heteroalkylene, substituted or unsubstituted alkylheteroarylene, substituted or unsubstituted heteroarylalkylene, —O—, —N(R$^A$)—, —S—, —C(=O)—, —C(=O)O—, —C(=O)NR$^A$—, —NR$^A$C(=O)—, —NR$^A$C(=O)O—, —NR$^A$C(=O)N(R$^A$)—, —OC(=O)—, —OC(=O)O—, or —OC(=O)N(R$^A$)—;

each occurrence of R$^A$ is, independently, hydrogen, substituted or unsubstituted acyl, substituted or unsubstituted alkyl, substituted or unsubstituted alkenyl, substituted or unsubstituted alkynyl, substituted or unsubstituted heteroalkyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R$^A$ groups are joined to form a substituted or unsubstituted heterocyclic ring;

L is substituted or unsubstituted alkylene, substituted or unsubstituted alkenylene, substituted or unsubstituted alkynylene, substituted or unsubstituted carbocyclylene, substituted or unsubstituted heterocyclylene, substituted or unsubstituted arylene, substituted or unsubstituted heteroarylene, substituted or unsubstituted heteroalkylene, —O—, —N(R$^A$)—, —S—, —C(=O)—, —C(=O)O—, —C(=O)NR$^A$—, —NR$^A$C(=O)—, —NR$^A$C(=O)R$^A$—, —C(=O)R$^A$—, —NR$^A$C(=O)O—, —NR$^A$C(=O)N(R$^A$)—, —OC(=O)—, —OC(=O)O—, or —OC(=O)N(R$^A$)—, or a combination thereof;

E is

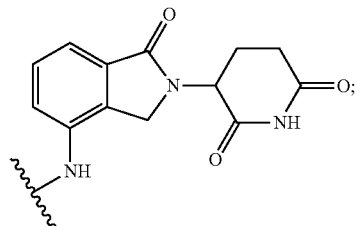

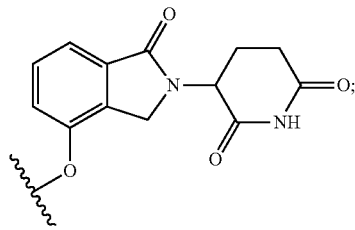

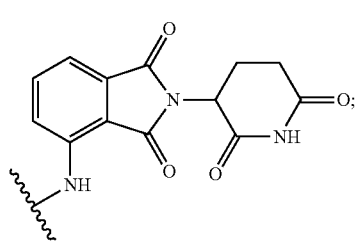

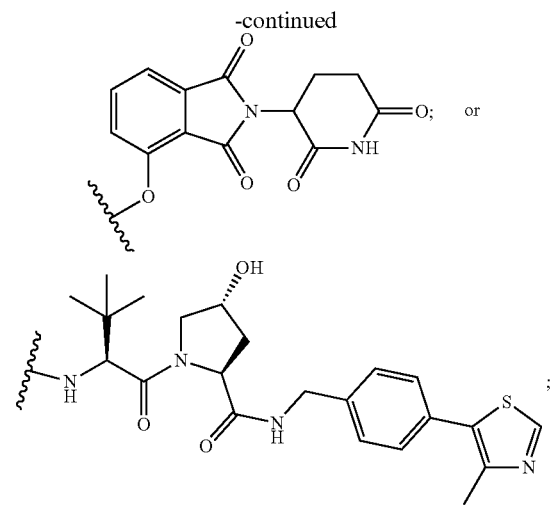

m and n are each independently 0 or 1, provided that m+n=1;

k is 0, 1, 2, 3, or 4; and p is 0, 1, 2, 3, or 4.

2. The compound of claim 1, or a pharmaceutically acceptable salt thereof, wherein:

A is

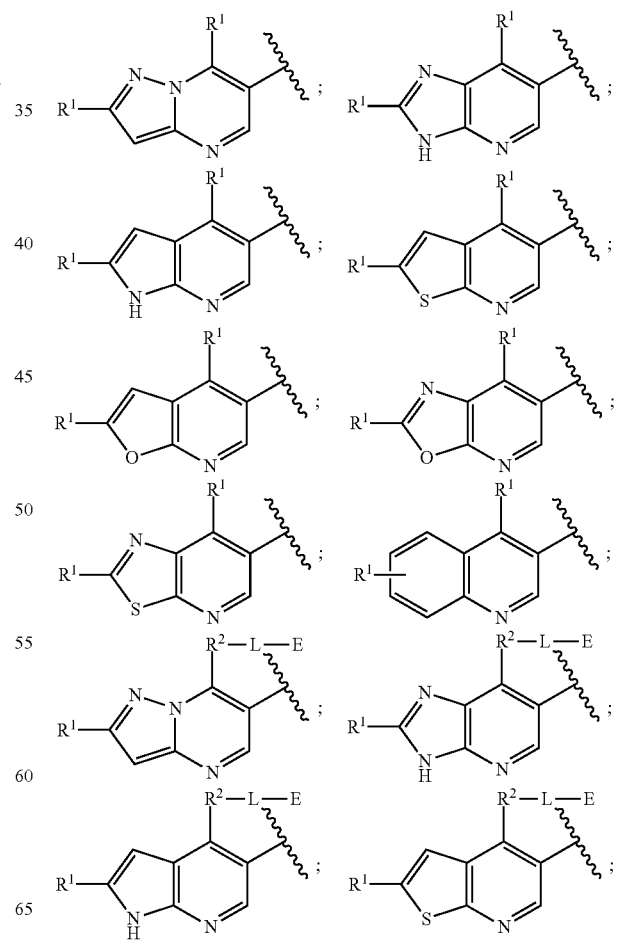

-continued

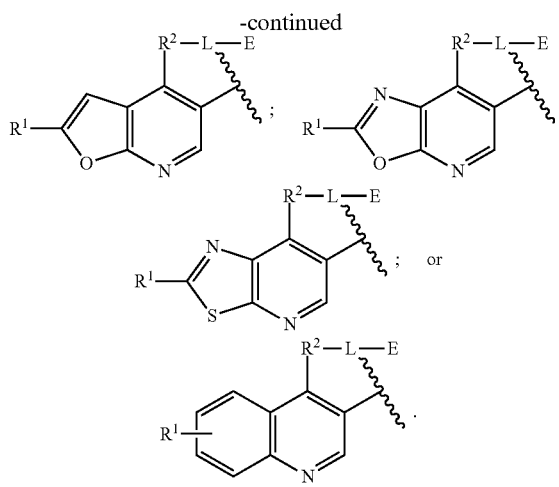

3. The compound of claim 1, or a pharmaceutically acceptable salt thereof, wherein B is pyridinyl.

4. The compound of claim 1, or a pharmaceutically acceptable salt thereof, wherein each occurrence of $R^1$ and $R^3$ is, independently, halogen, substituted or unsubstituted alkyl, substituted or unsubstituted alkenyl, substituted or unsubstituted alkynyl, substituted or unsubstituted heterocyclyl, substituted or unsubstituted aryl, substituted or unsubstituted heteroaryl, or substituted or unsubstituted heteroalkyl.

5. The compound of claim 1, or a pharmaceutically acceptable salt thereof, wherein $R^2$ is substituted or unsubstituted alkylene, substituted or unsubstituted heterocyclylene, substituted or unsubstituted heteroarylene, substituted or unsubstituted heteroalkylene, substituted or unsubstituted alkylheteroarylene, or —O—.

6. The compound of claim 1, or a pharmaceutically acceptable salt thereof, wherein L is substituted or unsubstituted alkylene, substituted or unsubstituted alkenylene, substituted or unsubstituted heterocyclylene, substituted or unsubstituted heteroarylene, substituted or unsubstituted heteroalkylene, —O—, —N($R^4$)—, —S—, —C(=O)—, —C(=O)O—, —C(=O)N$R^4$—, —N$R^4$C(=O)—, —N$R^4$C(=O)$R^4$—, —C(=O)$R^4$—, —N$R^4$C(=O)O—, —N$R^4$C(=O)N($R^4$)—, —OC(=O)—, —OC(=O)O—, or —OC(=O)N($R^4$)—.

7. The compound of claim 1, or a pharmaceutically acceptable salt thereof, wherein:
L is

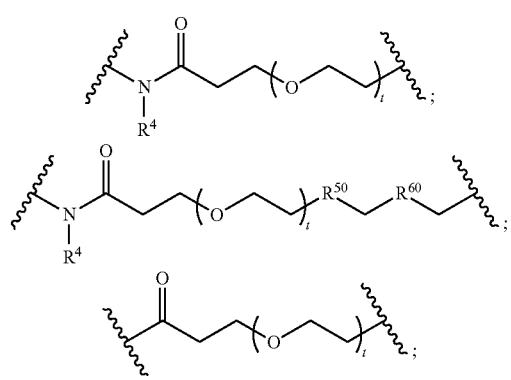

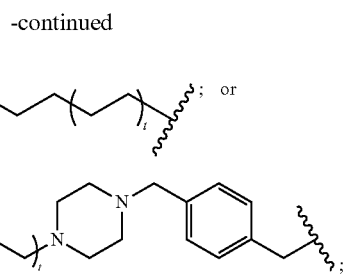

$R^4$ is hydrogen or $C_{1-6}$ alkyl;
t is 0, 1, 2, 3, 4, 5, or 6;
$R^{50}$ is substituted or unsubstituted heterocyclylene, or substituted or unsubstituted arylene; and
$R^{60}$ is substituted or unsubstituted heterocyclylene, or substituted or unsubstituted arylene.

8. The compound of claim 1, or a pharmaceutically acceptable salt thereof, wherein:
—$R^2$-L- is

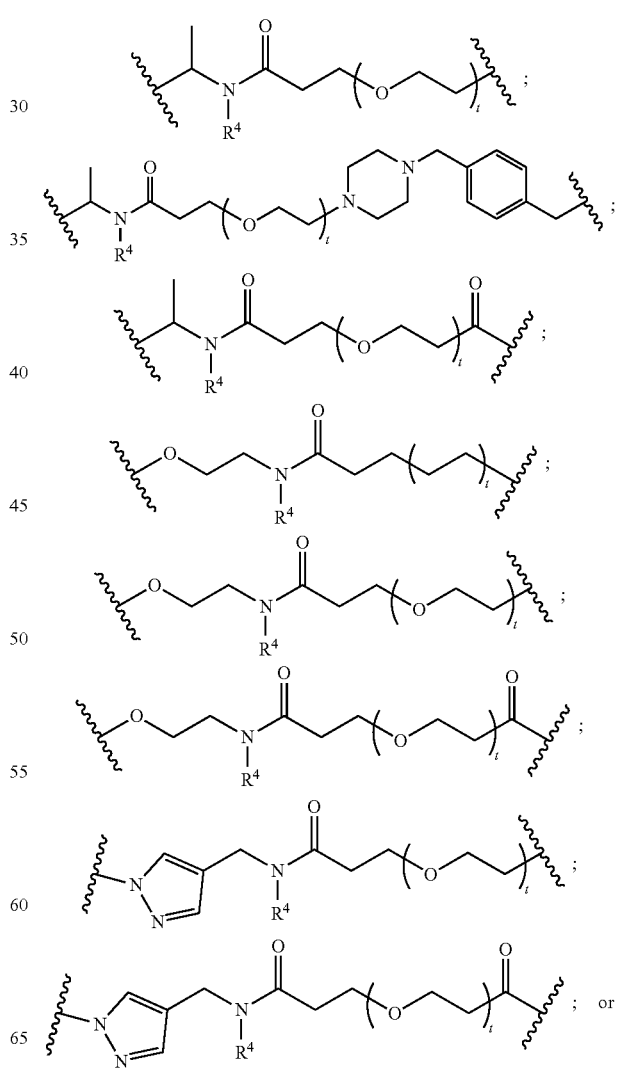

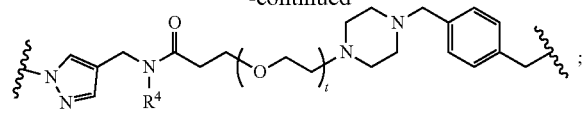

$R^4$ is hydrogen or $C_{1-6}$ alkyl; and
t is 0, 1, 2, 3, 4, 5, or 6.

9. The compound of claim 1, or a pharmaceutically acceptable salt thereof, wherein E binds to Cereblon or VHL.

10. The compound of claim 1, wherein the compound is of Formula I-a, Formula I-b, Formula I-c, Formula I-d, or Formula I-e:

I-a
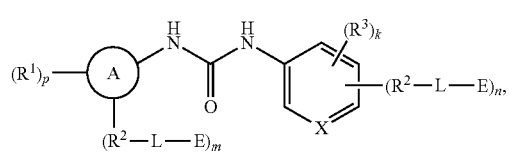

I-b
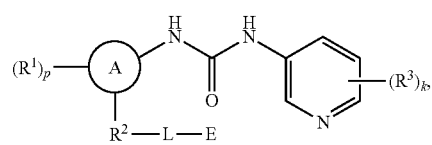

I-c
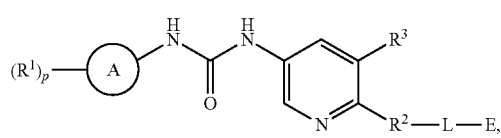

I-d
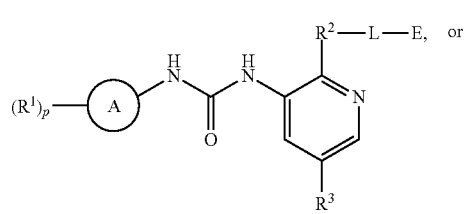

I-e
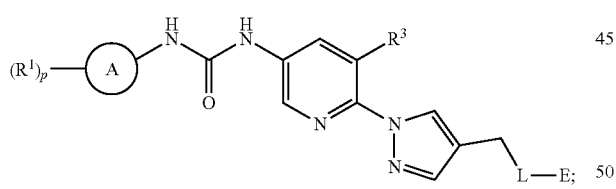

or a pharmaceutically acceptable salt thereof, wherein X is N, CH, or $CR^3$.

11. The compound of claim 1, wherein the compound is of Formula I-f, Formula I-g, Formula I-h, Formula I-I, or Formula I-j:

I-f
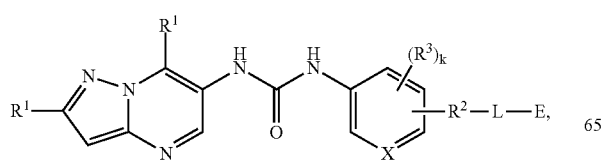

I-g
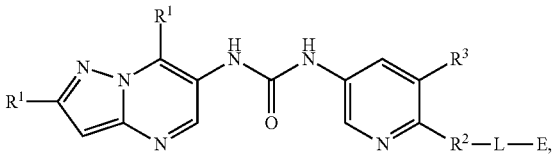

I-h
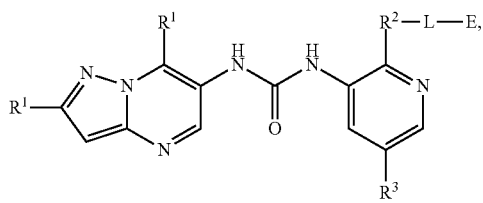

I-i
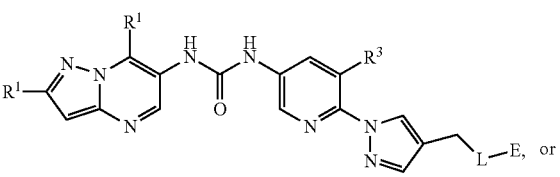

I-j
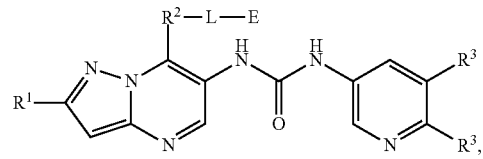

or a pharmaceutically acceptable salt thereof, wherein X is N, CH, or $CR^3$.

12. The compound of claim 1, wherein the compound is of Formula I-l, Formula I-m, Formula I-n, or Formula I-o:

I-l
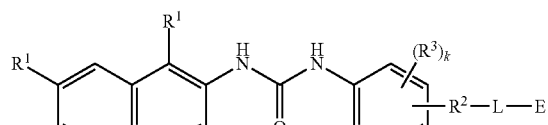

I-m
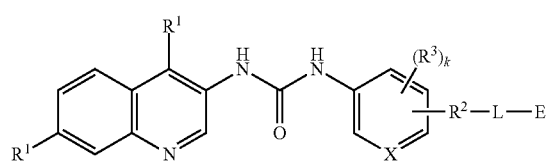

I-n
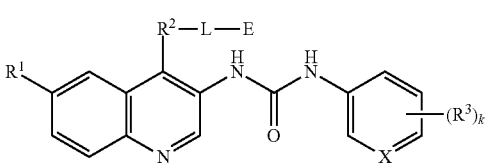

-continued

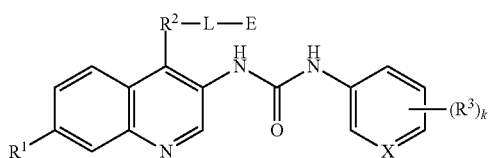
I-o or a pharmaceutically acceptable salt thereof, wherein X is N, CH, or $CR^3$.

13. The compound of claim 1, wherein the compound is of Formula I-p Formula I-q, Formula I-r, Formula I-s, Formula I-t, Formula I-u, or Formula I-v:

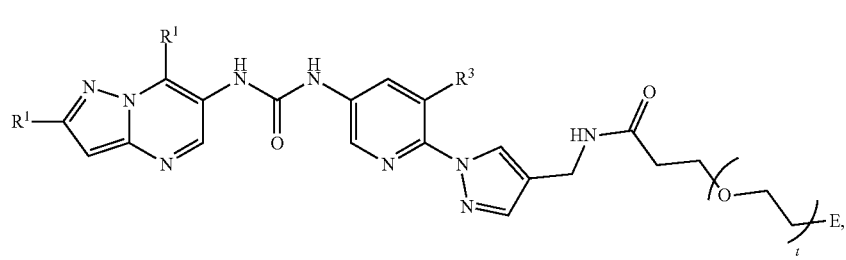
I-p or a pharmaceutically acceptable salt thereof, wherein t is 2 or 4;

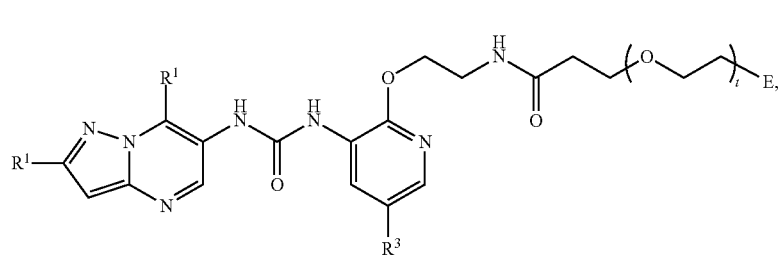
I-q or a pharmaceutically acceptable salt thereof, wherein t is 1, 2, 3, 4, 5, or 6;

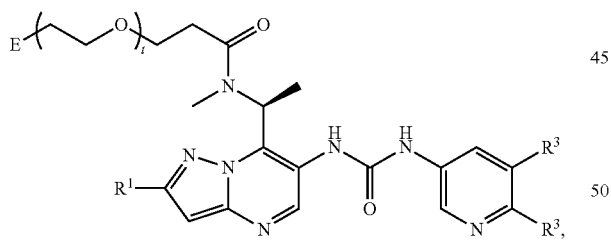
I-r or a pharmaceutically acceptable salt thereof, wherein t is 2 or 4;

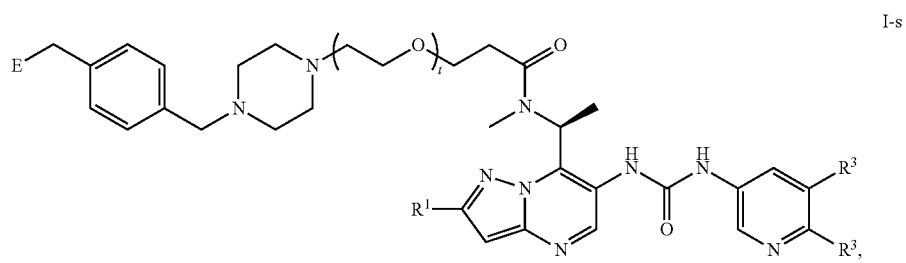
I-s or a pharmaceutically acceptable salt thereof, wherein t is 0, 1, 2, 3, 4, 5, or 6;
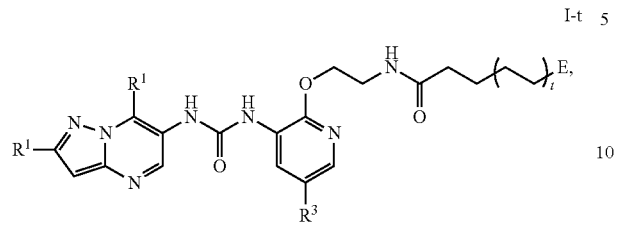
I-t
or a pharmaceutically acceptable salt thereof, wherein t is 0, 1, 2, 3, 4, 5, or 6;
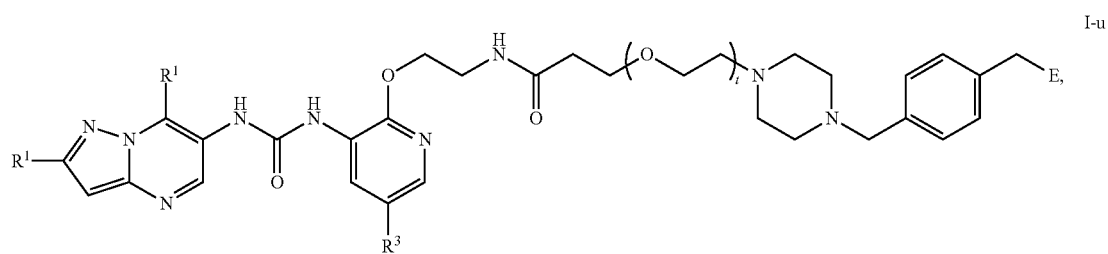
I-u
or a pharmaceutically acceptable salt thereof, wherein t is 0, 1, 2, 3, 4, 5, or 6;
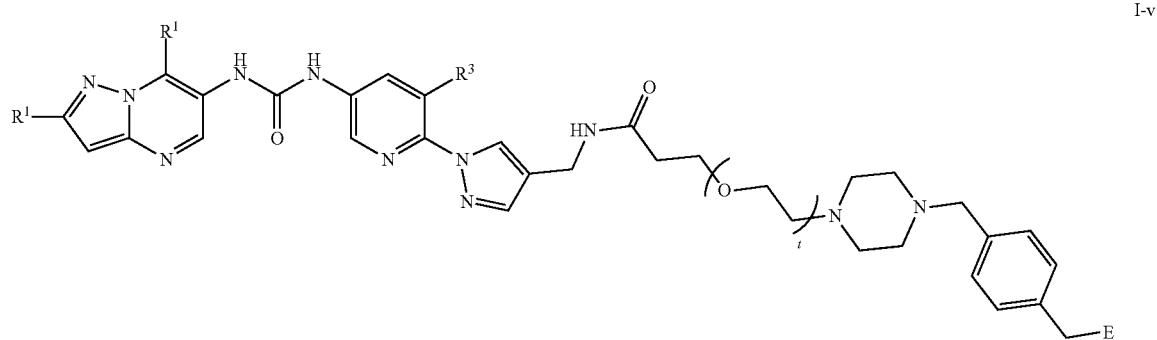
I-v
or a pharmaceutically acceptable salt thereof, wherein t is 0, 1, 2, 3, 4, 5, or 6.
14. The compound of claim 1, wherein the compound is
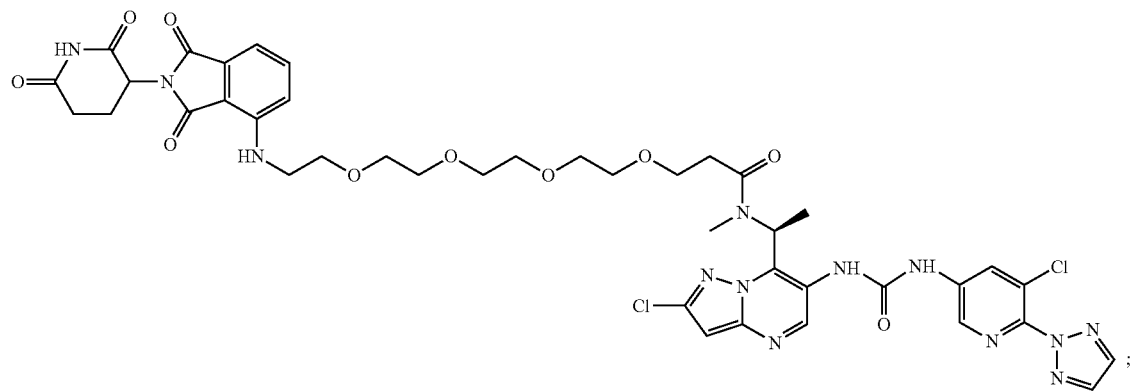

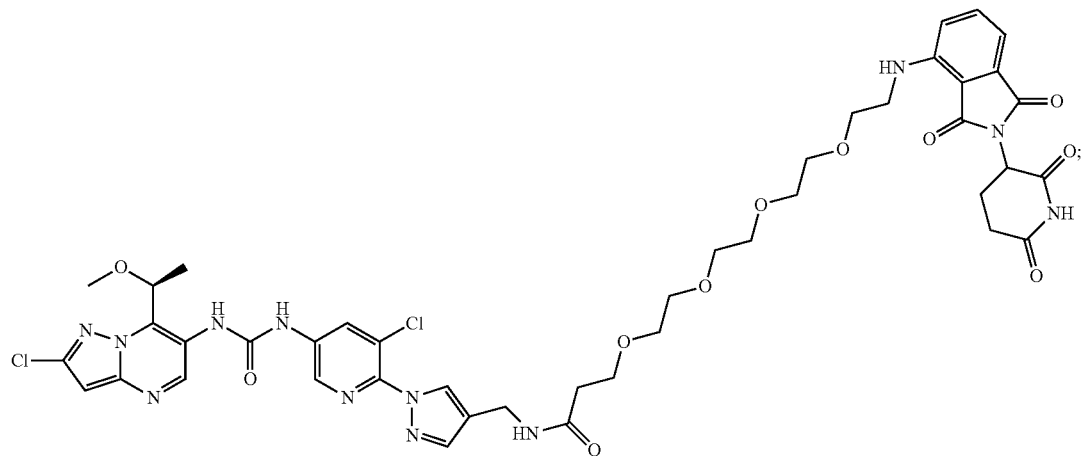
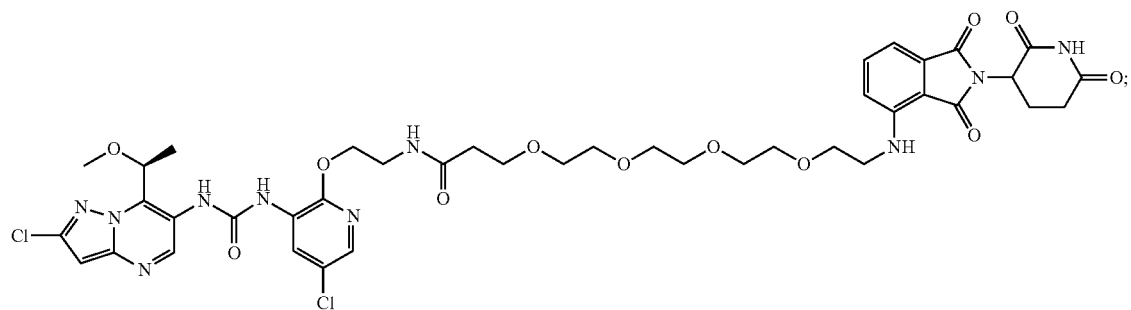
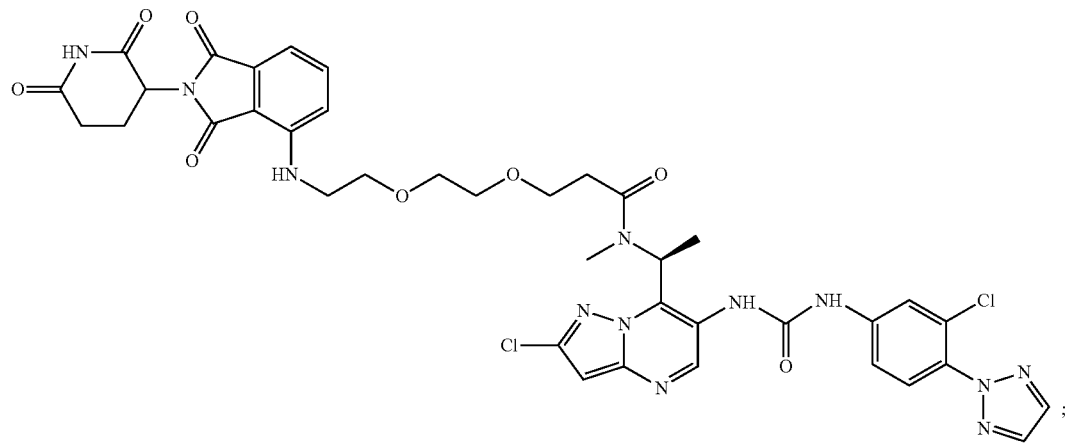
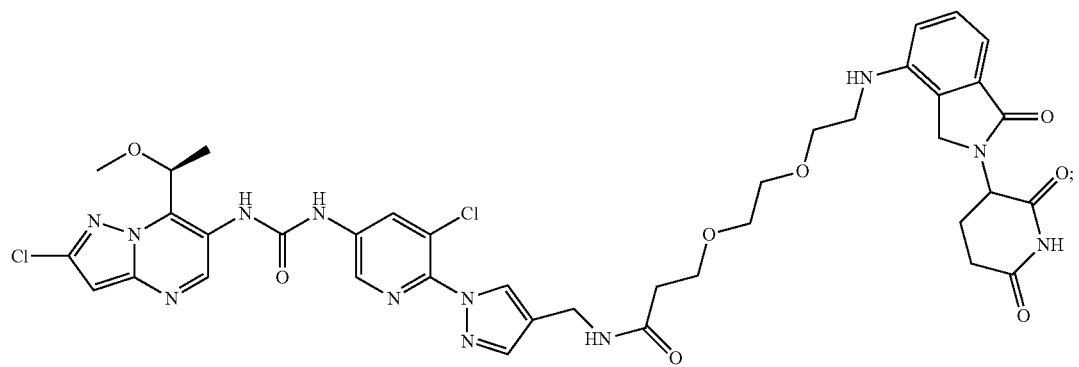

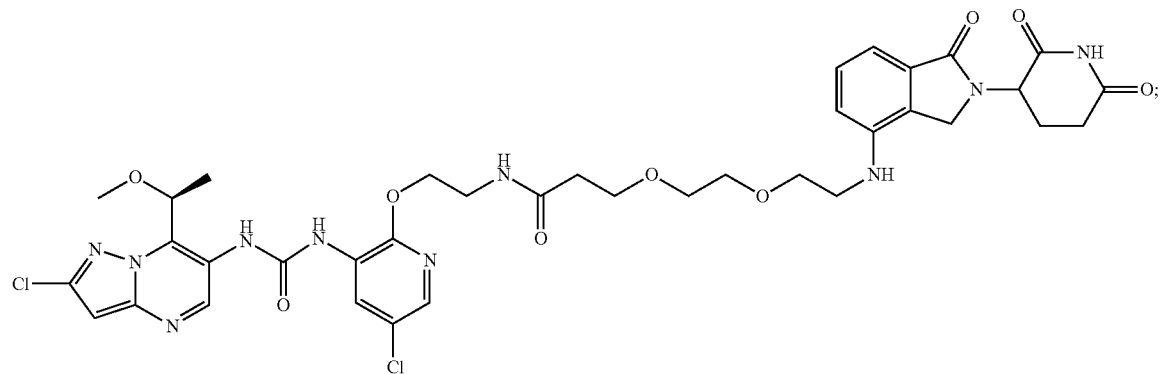
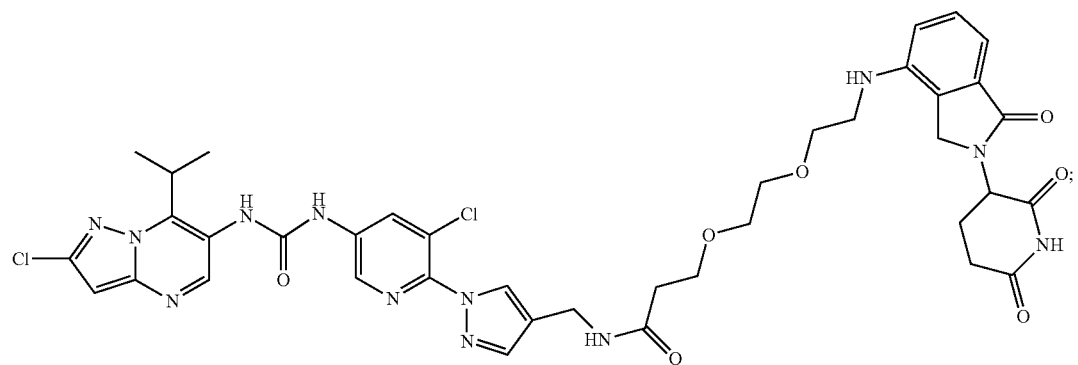
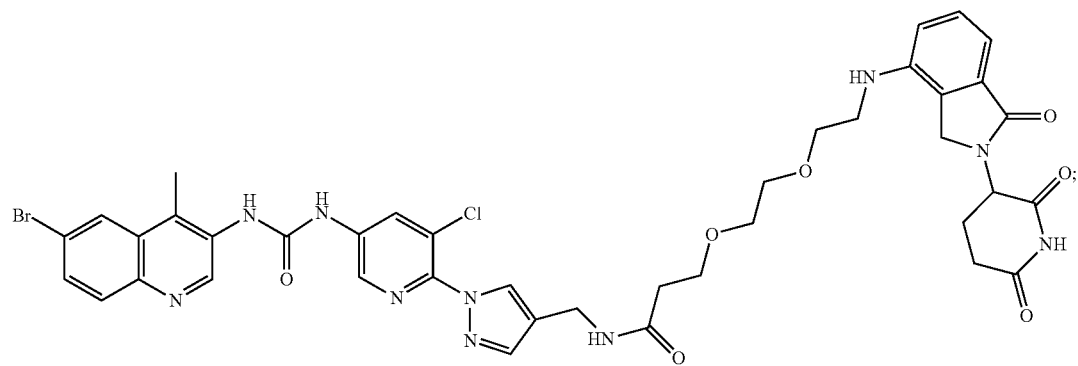
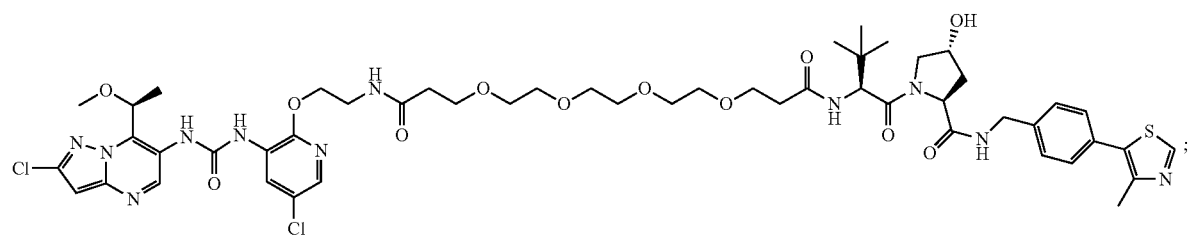

-continued
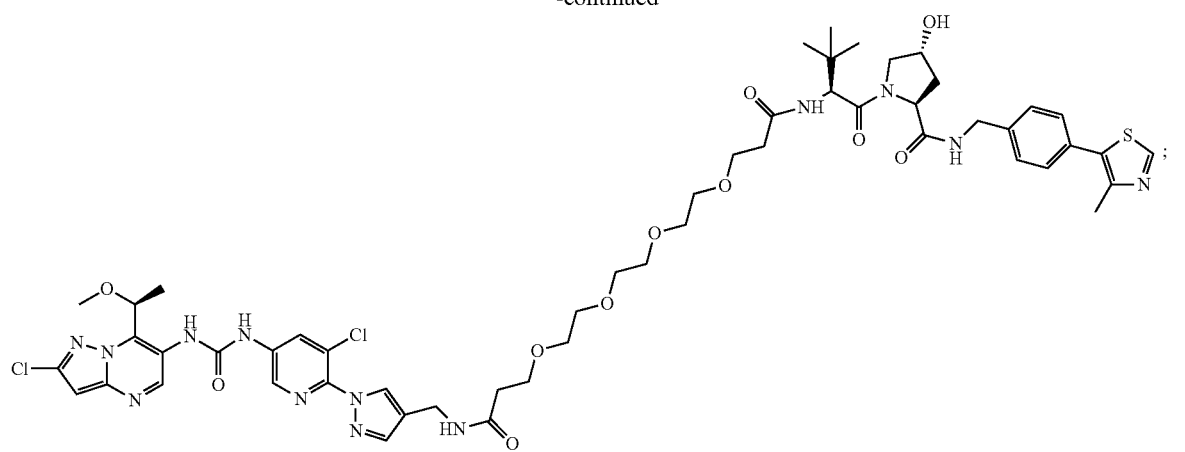
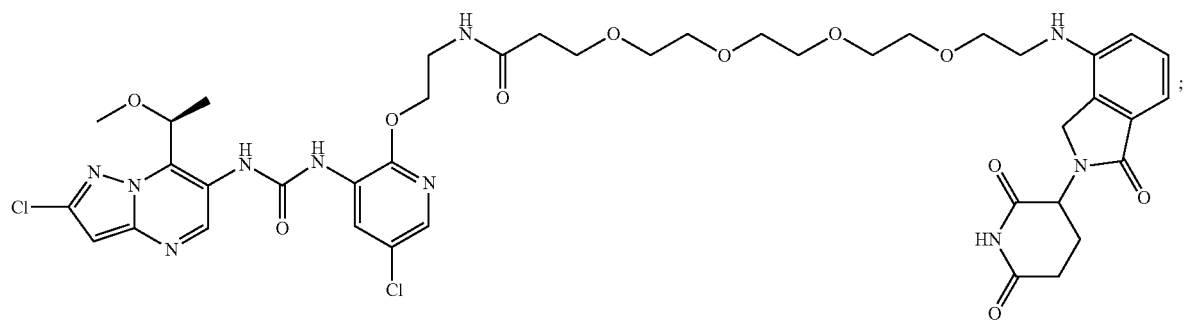
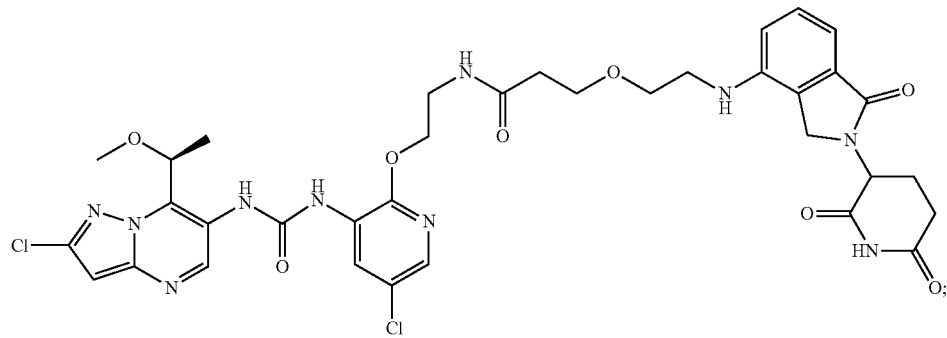
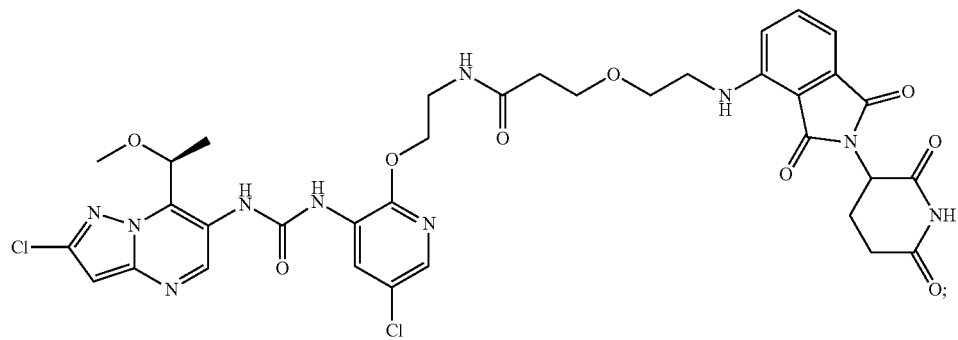

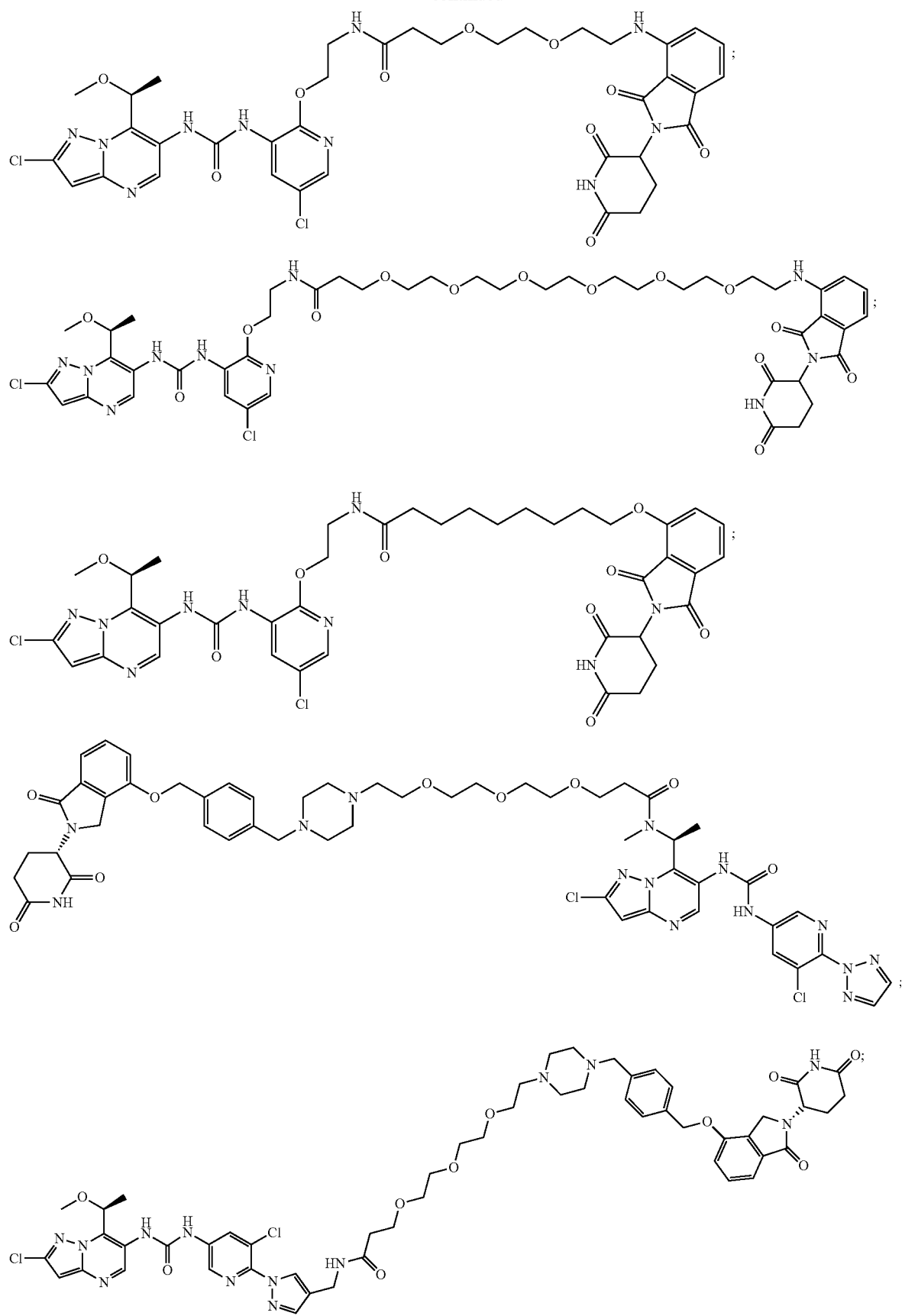

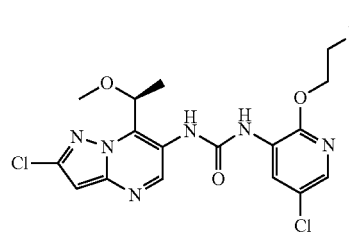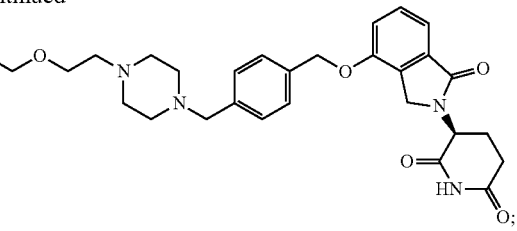

or a pharmaceutically acceptable salt thereof.

15. A pharmaceutical composition comprising a compound of claim 1, or a pharmaceutically acceptable salt thereof, and a pharmaceutically acceptable excipient.

16. A method of treating cancer in a subject in need thereof, the method comprising administering a compound of claim 1, or a pharmaceutically acceptable salt thereof.

17. A method of promoting the degradation of MALT1 in a subject in need thereof, the method comprising administering a compound of claim 1, or a pharmaceutically acceptable salt thereof.

18. A method of promoting the degradation of MALT1 and binding an E3 ubiquitin ligase in a subject in need thereof, the method comprising administering a compound of claim 1, or a pharmaceutically acceptable salt thereof.

19. A kit comprising a compound of claim 1, or a pharmaceutically acceptable salt thereof; and instructions for administering the compound, the pharmaceutically acceptable salt thereof.

* * * * *

UNITED STATES PATENT AND TRADEMARK OFFICE
CERTIFICATE OF CORRECTION

PATENT NO. : 10,689,366 B2
APPLICATION NO. : 16/346483
DATED : June 23, 2020
INVENTOR(S) : Ari M. Melnick et al.

It is certified that error appears in the above-identified patent and that said Letters Patent is hereby corrected as shown below:

On the Title Page

In item (54), and in the Specification, Column 1, Line 1, the Title is hereby corrected as shown below:
COMPOUNDS FOR MALT1 DEGRADATION

In the Claims

In Claim 14, in Columns 185 and 186, the formula:

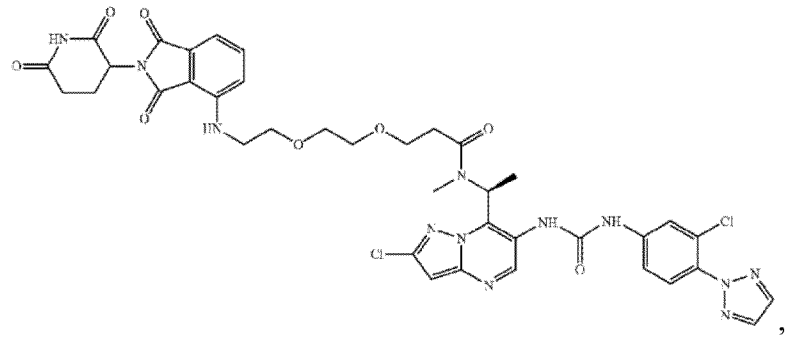

Should be replaced with the formula:

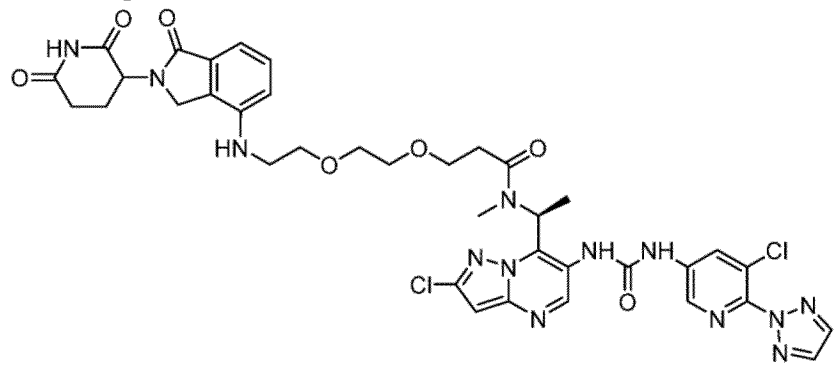

Signed and Sealed this
Twenty-fifth Day of January, 2022

Drew Hirshfeld
*Performing the Functions and Duties of the
Under Secretary of Commerce for Intellectual Property and
Director of the United States Patent and Trademark Office*